ized with US012121515B2

United States Patent
Khanna et al.

(10) Patent No.: US 12,121,515 B2
(45) Date of Patent: *Oct. 22, 2024

(54) PIPERIDINE UREA DERIVATIVES AS SOLUBLE EPOXIDE HYDROLASE INHIBITORS

(71) Applicant: NeuroPn Therapeutics, Inc., Peachtree Corners, GA (US)

(72) Inventors: Ish Khanna, Alpharetta, GA (US); Sivaram Pillarisetti, Peachtree Corners, GA (US)

(73) Assignee: NeuroPn Therapeutics, Inc., Peachtree Corners, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/366,113

(22) Filed: Aug. 7, 2023

(65) Prior Publication Data

US 2024/0075023 A1 Mar. 7, 2024

Related U.S. Application Data

(63) Continuation of application No. 17/720,450, filed on Apr. 14, 2022, now Pat. No. 11,998,538.

(60) Provisional application No. 63/174,665, filed on Apr. 14, 2021.

(51) Int. Cl.
| | |
|---|---|
| *A61K 31/4545* | (2006.01) |
| *A61K 31/445* | (2006.01) |
| *A61K 31/454* | (2006.01) |
| *A61K 31/497* | (2006.01) |
| *A61K 31/506* | (2006.01) |
| *A61K 31/5377* | (2006.01) |
| *A61P 25/02* | (2006.01) |
| *A61P 25/16* | (2006.01) |

(52) U.S. Cl.
CPC ........ *A61K 31/4545* (2013.01); *A61K 31/445* (2013.01); *A61K 31/454* (2013.01); *A61K 31/497* (2013.01); *A61K 31/506* (2013.01); *A61K 31/5377* (2013.01); *A61P 25/02* (2018.01); *A61P 25/16* (2018.01)

(58) Field of Classification Search
CPC .............. A61K 31/4545; A61K 31/445; A61K 31/454; A61K 31/497; A61K 31/506; A61K 31/5377; A61P 25/02; A61P 25/16
See application file for complete search history.

(56) References Cited

U.S. PATENT DOCUMENTS

| | | | |
|---|---|---|---|
| 8,399,425 B2 | 3/2013 | Hammock et al. | |
| 2011/0144159 A1* | 6/2011 | Fay | A61P 21/00 546/196 |
| 2019/0077785 A1* | 3/2019 | Hammock | C07C 275/36 |
| 2021/0155601 A1 | 5/2021 | Hammock et al. | |

FOREIGN PATENT DOCUMENTS

| | | |
|---|---|---|
| WO | WO 2011021645 | 2/2011 |
| WO | WO 2017160861 | 9/2017 |
| WO | WO 2020010244 | 1/2020 |

OTHER PUBLICATIONS

K. Takai et al. (Bioorganic & Medicinal Chemistry, vol. 22, Issue 5, 2014, pp. 1548-1557. (Year: 2014).*
S. Kodani et al. (Design and Potency of Dual Soluble Epoxide Hydrolase/Fatty Acid Amide Hydrolase Inhibitors, ACS Omega, 2018, VL-3, IS-10, pp. 14076-14086, doi: 10.1021/acsomega. 8b01625. (Year: 2018).*
Brunst, Steffen, et al., Systemic Assessment of Fragment Identification for Multitarget Drug Design, ChemMedChem Communications, vol. 16, No. 7, Feb. 4, 2021.
Shen, Hong C., et al., Discovery of Spirocyclic Secondary Amine-derived Tertiary Ureas as Highly Potent, Selective and Bioavailable Soluble Epoxide Hydrolase Inhibitors, Bioorganic & Medicinal Chemistry Letters, vol. 19, No. 13, Elsevier, Amsterdam, NL, Jul. 1, 2009.
Takai, Kentaro, et al., Structure-based Optimization of Cyclopropyl Urea Derivatives as Potent Soluble Epoxide Hydrolase Inhibitors for Potential Decrease of Renal Injury Without Hypotensive Action, Bioorganic & Medicinal Chemistry, vol. 22, No. 5, Elsevier, Amsterdam NL, Jan. 31, 2014.
Takai, Kentaro, et al., Three-dimensional Rational Approach to the Discovery of potent Substituted Cyclopropyl Urea Soluble Epoxide Hydrolase Inhibitors Bioorganic & Medicinal Chemistry Letters, vol. 25, No. 8, Elsevier, Amsterdam NL, Mar. 7, 2015.
Kodani, Sean D., et al., Design and Potency of Dual Soluble Epoxide Hydrolase/Fatty Acid Amide Hydrolase Inhibitors, ACS Omega, vol. 3, pp. 14076-14086, Oct. 25, 2018.

* cited by examiner

*Primary Examiner* — Bahar Craigo
*Assistant Examiner* — Manahil Mirghani Ali Abdalhameed
(74) *Attorney, Agent, or Firm* — Offit Kurman; Douglas L. Lineberry

(57) ABSTRACT

Described herein are novel piperidine urea derived compounds and their pharmaceutical compositions for the treatment of conditions and diseases mediated by soluble epoxide hydrolase.

24 Claims, 7 Drawing Sheets

TABLE -1

| Example | Compound | Human sEH (IC$_{50}$) |
|---|---|---|
| 1 | 4-(3-methoxy-benzylidene)-piperidine-1-carboxylic acid (2-phenyl-cyclopropyl)-amide | 12.1 nM |
| 2 | 4-[3-(pyridin-2-yloxy)-benzylidene]-piperidine-1-carboxylic acid (2-phenyl-cyclopropyl)-amide | 15.0 nM |
| 3 | 4-[3-(5-trifluoromethyl-pyridin-2-yloxy)-benzylidene]-piperidine-1-carboxylic acid (2-phenyl-cyclopropyl)-amide | 12.1 nM |
| 4 | 4-[3-(pyridin-2-yloxy)-benzyl]-piperidine-1-carboxylic acid (2-phenyl-cyclopropyl)-amide | 60 nM |
| 5A | 4-[3-(pyridin-2-yloxy)-benzylidene]-piperidine-1-carboxylic acid {(1S,2R)-2-phenyl-cyclopropyl)}-amide | 6.3 nM |
| 5B | 4-[3-(pyridin-2-yloxy)-benzylidene]-piperidine-1-carboxylic acid {(1R,2S)-2-phenyl-cyclopropyl)}-amide | 9.4 nM |
| 6 | 4-[3-(pyrimidin-2-yloxy)-benzylidene]-piperidine-1-carboxylic acid (2-phenyl-cyclopropyl)-amide | 9.1 nM |
| 7 | 4-{3-[1-(2-phenyl-cyclopropylcarbamoyl)-piperidin-4-ylidenemethyl]-phenoxy}-benzoic acid methyl ester | < 1uM |
| 8 | 4-{3-[1-(2-phenyl-cyclopropylcarbamoyl)-piperidin-4-ylidenemethyl]-phenoxy}-benzoic acid | 5.0 nM |
| 9 | 4-(3-pyrrolidin-1-yl-benzyl)-piperidine-1-carboxylic acid-(2-phenyl-cyclopropyl)-amide | 14.4 nM |
| 10 | 4-(3-morpholin-4-yl-benzyl)-piperidine-1-carboxylic acid (2-phenyl-cyclopropyl)-amide | < 15 nM |
| 11 | 4-[3-(pyridin-2-yloxy)-phenoxy]-piperidine-1-carboxylic acid (2-phenyl-cyclopropyl)-amide | 12.8 nM |
| 12 | 4-[3-(1H-pyrazol-4-yl)-benzyl]-piperidine-1-carboxylic acid (-2-phenyl-cyclopropyl)-amide | 13.5 nM |
| 13 | 4-[3-(1-methyl-1H-pyrazol-4-yl)-benzyl]-piperidine-1-carboxylic acid (2-phenyl-cyclopropyl)-amide | 12.4 nM |
| 14 | 4-(3-benzoimidazol-1-yl-benzyl)-piperidine-1-carboxylic acid (2-phenyl-cyclopropyl)-amide | 9.4 nM |
| 15 | 4-(3-pyrrolidin-1-yl-benzylidene)-piperidine-1-carboxylic acid (2-phenyl-cyclopropyl)-amide | 12.0 nM |
| 17 | 4-[3-(5-trifluoromethyl-pyridin-2-yloxy)-benzylidene]-piperidine-1-carboxylic acid {(1S,2R)-2-phenyl-cyclopropyl)]-amide | 13.6 nM |
| 18 | 4-[3-(5-trifluoromethyl-pyridin-2-yloxy)-benzylidene]-piperidine-1-carboxylic acid {(1R,2S)-2-phenyl-cyclopropyl)]-amide | 4.7 nM |
| 19 | 4-({3-[(5-methylpyridin-2-yl)oxy]phenyl} methylidene)-N-[2-phenylcyclopropyl]piperidine-1-carboxamide | 6.6 nM |
| 20 | 4-[3-(pyridin-2-yloxy)-benzylidene]-piperidine-1-carboxylic acid [2-(4-methyl)phenyl-cyclopropyl]-amide | 6.9 nM |
| 21 | 4-[3-(pyrimidin-2-yloxy)-benzylidene]-piperidine-1-carboxylic acid [(1R, 2S)-2-phenyl-cyclopropyl]-amide | 3.1 nM |
| 22 | 4-[3-(5-methyl-pyridin-2-yloxy)-benzylidene]-piperidine-1-carboxylic acid ((1R,2S)-2-phenyl-cyclopropyl)-amide | 3.2 nM |
| 23 | 4-[3-(pyrimidin-2-yloxy)-benzylidene]-piperidine-1-carboxylic acid methyl-((1R,2S)-2-phenyl-cyclopropyl)-amide | 1.2 uM |
| 24 | 4-[3-(5-methyl-pyrazin-2-yloxy)-benzylidene]-piperidine-1-carboxylic acid ((1R,2S)-2-phenyl-cyclopropyl)-amide | 4.2 nM |

FIG. 1

| 25 | 4-[3-(5-chloro-pyridin-2-yloxy)-benzylidene]-piperidine-1-carboxylic acid ((1R,2S)-2-phenyl-cyclopropyl)-amide | 3.3 nM |
| 26 | 4-[3-(5-fluoro-pyridin-2-yloxy)-benzylidene]-piperidine-1-carboxylic acid ((1R,2S)-2-phenyl-cyclopropyl)-amide | 7.6 nM |
| 27 | 6-{3-[1-((1R,2S)-2-Phenyl-cyclopropylcarbamoyl)-piperidin-4-ylidenemethyl]-phenoxy}-nicotinic acid methyl ester | |
| 28 | 6-{3-[1-((1R,2S)-2-Phenyl-cyclopropylcarbamoyl)-piperidin-4-ylidenemethyl]-phenoxy}-nicotinic acid | 6.6 nM |
| 29 | 4-[3-(5-Hydroxymethyl-pyridin-2-yloxy)-benzylidene]-piperidine-1-carboxylic acid ((1R,2S)-2-phenyl-cyclopropyl)-amide | 2.3 nM |
| 30 | 4-[3-(5-Methoxymethyl-pyridin-2-yloxy)-benzylidene]-piperidine-1-carboxylic acid ((1R,2S)-2-phenyl-cyclopropyl)-amide | 2.1 nM |

**FIG. 1
(CONT.)**

PIPERIDINE UREA DERIVATIVES AS SOLUBLE EPOXIDE HYDROLASE INHIBITORS

TECHNICAL FIELD

The subject matter disclosed herein is generally directed to methods and compositions for the treatment of pain and neurodegenerative disease, specifically, select piperidine urea-derived compounds for the treatment of neuropathic pain and neurodegenerative disease as well as to methods of treatment of conditions and diseases mediated by soluble epoxide hydrolase.

BACKGROUND

Epoxidation of arachidonic acid by cytochrome P450 enzymes during inflammation and injury yields epoxyeicosatrienoic acids (EETs). The EETs have a variety of biological effects including modulation of inflammation, endothelial function and neuronal cell survival. EETs levels are regulated by soluble epoxide hydrolase (sEH), the major enzyme responsible for their degradation and conversion to inactive dihydroxyeicosatrienoic acids (DHETs). sEH, thereby, limits many of the biological actions of EETs. EETs produce important biological effects, particularly in the vascular and nervous systems. Inhibiting sEH increases the half-life of EETs which in turn translates into beneficial therapeutic effects.

sEH inhibitors may have utility in treatment of neuropathic and inflammatory pain, neurodegenerative diseases, acute respiratory distress syndrome (ARDS), rheumatoid arthritis (RA), inflammatory bowel disease (IBD), and Crohn's disease [Biomolecules (2020), 10, 703-724; Proc. Natl. Acad. Sciences. (2018), 115, E5815-E5823, Neurotherapeutics. (2020), 17(3), 900-916; Proc. Natl. Acad. Sciences. (2008), 105 (48), 18901-18906; Pharmacology & Therapeutics 180 (2017) 62-76; *Nat. Rev. Drug. Discov.* (2009), 8(10), 794-805; *Cardiovasc. Hematol. Agents Med. Chem.* (2012), September, 10(3), 212-22; *Prostaglandins and Other Lipid Mediators* 140 (2019) 31-39, *Progress in Neurobiology*, (2019), 172, 23-39, *Inflamm. Allergy Drug Targets* (2012) April, 11(2), 143-58; *Mol. Pain* (2011), 4, 7-78; *Drug Discov Today.* 2015 November; 20(11):1382-90, *Biomolecules.* 2020 May 1; 10(5):703, *Prostaglandins Other Lipid Mediat*. (2011), 96, 76-83, *Pharmacology & Therapeutics* 180 (2017) 62-76; *Pharmacol Ther.* 2017 Jun. 19, S0163-7258 (17)30154-7]; Biochimie 159 (2019) 59-65. The sEH inhibitors reduce expression of inflammatory genes and show potential utility in inflammatory diseases (*Inflamm. Allergy Drug Targets* (2012) April, 11(2):143-58). The 14,15-EET is about 35-fold more potent than morphine and stimulates met-enkaphline in brain suggesting potential utility for analgesia (*J Pharmacol Exp. Ther*. (2008), August, 326(2), 614-22).

Several studies validate that EETs and sEH inhibition carry neuroprotective properties. sEH is highly expressed in brain and EETs production and metabolism in the brain spans many regions and extends to peripheral and central neurons, astroglia and oligodendrocytes, vascular endothelial and smooth muscle cells [*J Histochem Cytochem.* 2008 June; 56(6):551-9, *Am J Physiol* 263: H519-25 1992, *J Neurochem* 61: 150-9 1993 *Prostaglandins Other Lipid Mediat.* 91: 68-84 2010]. Studies showed that EETs or sEH inhibition—i) prevent cytokine and oxidant mediated injury in neuronal cells; ii) prevent endoplasmic reticulum (ER) stress, a key contributor to loss of dopaminergic neurons; iii) augment astrocyte release of vascular endothelial growth factor and neuronal recovery after oxygen-glucose deprivation; and iv) promote axonal growth [*Am J Physiol Heart Circ Physiol* 296: H1352-63, 2009, *Expert Rev Mol Med* 13: 7-12 2011, *Expert Rev Mol Med* 13: 7-12, 1998, *Expert Rev Mol Med* 13: 7-12, 2014, *Neuropathol Appl Neurobiol.* 42:607-620, 2016, *Proc Natl Acad Sci USA*. 112: 9082-9087 2015, *J Neurosci* 27: 4642-9 2007, *J Neurochem.* 117: 632-42 2011 and *Neuroscience* 223: 68-76 2012]. sEH deficiency attenuates dopaminergic neuronal cell loss in a paraquat-induced mouse model of Parkinson's disease [*Mol Neurobiol.* 52(1):187-95 2015]. In multiple animal models, inhibition of sEH alleviates neuropathy and neuropathic pain including diabetic neuropathic pain [*Proc Natl Acad Sci USA*. 2008 Dec. 2; 105(48):18901-6, *Eur J Pharmacol.* 2013 Jan. 30; 700 (1-3):93-101, *J Pain.* 2014 September; 15(9): 907-14, *Proc Natl Acad Sci USA.* 2015 Jul. 21; 112(29): 9082-7, *Behav Brain Res.* 2017 May 30; 326:69-76]. sEH levels are elevated in cortical brain tissue from subjects with cognitive impairment and sEH inhibition prevents $H_2O_2$-induced hyperphosphorylation of tau protein, a key factor in the pathogenesis of Alzheimer's disease [*Prostaglandins Other Lipid Mediat.* 2014 October; 113-115:30-7, *J Huazhong Univ Sci Technolog Med Sci.* 2016 December; 36(6):785-790]. sEH inhibition is protective in rodent models of ischemic and diabetic stroke [*Future Neurol.* 2009 Mar. 1; 4(2):179-199, *Am J Pathol.* 2009 June; 174(6):2086-95, *PLoS One.* 2014 May 13; 9 (5):e97529, *Am J Physiol Heart Circ Physiol.* 2013 Dec. 1; 305 (11):H1605-13].

Accordingly, it is an object of the present disclosure to provide methods and novel compositions for the treatment of pain and neurodegenerative disease, specifically, select piperidine urea-derived compounds for the treatment of neuropathic pain and Parkinson's disease as well as methods of treatment of conditions and diseases mediated by soluble epoxide hydrolase.

Citation or identification of any document in this application is not an admission that such a document is available as prior art to the present disclosure.

SUMMARY

The above objectives are accomplished according to the present disclosure by providing in a first embodiment, a composition that may comprise at least one compound of Formula I:

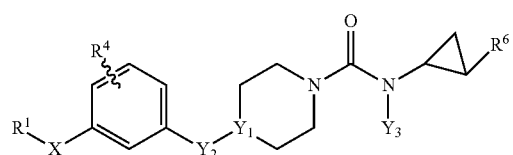

Formula I its stereoisomers or pharmaceutically acceptable salts thereof;
wherein
$R^1$ is selected from a group consisting of alkyl, hydrogen, haloalkyl, cycloalkyl, heterocycloalkyl, aryl, or heteroaryl and wherein $R^1$ may optionally be substituted one or more times with groups or substituents such as alkyl, hydroxy, halogen, haloalkyl, hydroxyalkyl, alkoxyalkyl, alkoxy, amine, $SO_2NHR^2$, $COR^3$ R² is selected from a group consisting of hydrogen, alkyl, haloalkyl, or cycloalkyl R³ is selected from a group consisting of alkyl, cycloalkyl, hydroxy, amine, alkyamine or alkoxy R⁴ is selected from a group consisting of hydrogen, alkyl, halogen, haloalkyl, hydroxy, amine, alkoxy, SO₂R⁵, COR³

R⁵ is selected from a group consisting of alkyl, haloalkyl, cycloalkyl, aryl or amine R⁶ is selected from a group consisting of alkyl, cycloalkyl, aryl or heteroaryl. Aryl or heteroaryl may optionally be substituted one or more times with groups or substituents such as alkyl, hydroxy, halogen, haloalkyl X is selected from O, (CH₂)p, NH; wherein p is selected from 0-2 and Y₁-Y₂ are selected from CH₂—CH₂, CH₂—O or CH=CH; however, when Y₁-Y₂ is CH₂—O, X is selected from O or NH; or R¹ is not hydrogen Y₃ is selected from H or Me In a further embodiment, a composition may be provided according to Formula II:

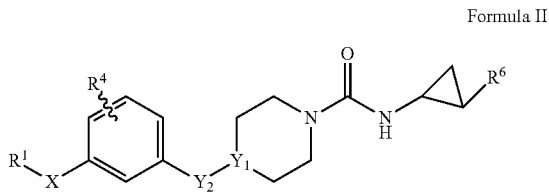

Formula II its stereoisomers or pharmaceutically acceptable salts thereof;
wherein R¹ is selected from a group consisting of alkyl, hydrogen, haloalkyl, cycloalkyl, heterocycloalkyl, aryl, or heteroaryl and wherein R¹ may optionally be substituted one or more times with groups or substituents such as alkyl, hydroxy, halogen, haloalkyl, hydroxyalkyl, alkoxyalkyl, alkoxy, amine, SO₂NHR², COR³

R² is selected from a group consisting of hydrogen, alkyl, haloalkyl, or cycloalkyl R³ is selected from a group consisting of alkyl, cycloalkyl, hydroxy, amine, alkylamine or alkoxy R⁴ is selected from a group consisting of hydrogen, alkyl, halogen, haloalkyl, hydroxy, amine, alkoxy, SO₂R⁵, COR³

R⁵ is selected from a group consisting of alkyl, haloalkyl, cycloalkyl, aryl or amine R⁶ is selected from a group consisting of alkyl, cycloalkyl, aryl or heteroaryl. Aryl or heteroaryl may optionally be substituted one or more times with groups or substituents such as alkyl, hydroxy, halogen, haloalkyl X is selected from O, (CH₂)p, NH; wherein p is selected from 0-2 and Y₁-Y₂ are selected from CH₂—CH₂, CH₂—O or CH=CH; however, when Y₁-Y₂ is CH₂—O, X is selected from O or NH or R¹ is not hydrogen In a still further embodiment, a composition may be provided according to Formula III:

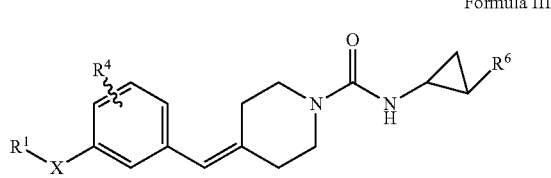

Formula III its stereoisomers or pharmaceutically acceptable salts thereof;
wherein R¹ is selected from a group consisting of alkyl, hydrogen, haloalkyl, cycloalkyl, heterocycloalkyl, aryl, or heteroaryl and wherein R¹ may optionally be substituted one or more times with groups or substituents such as alkyl, hydroxy, halogen, haloalkyl, hydroxyalkyl, alkoxyalkyl, alkoxy, amine, SO₂R⁵, SO₂NHR², COR³

R² is selected from a group consisting of hydrogen, alkyl, haloalkyl, or cycloalkyl R³ is selected from a group consisting of alkyl, cycloalkyl, hydroxy, amine, alkyamine or alkoxy R⁴ is selected from a group consisting of hydrogen, alkyl, halogen, haloalkyl, hydroxy, amine, alkoxy, SO₂R⁵, COR³

R⁵ is selected from a group consisting of alkyl, haloalkyl, cycloalkyl, aryl or amine R⁶ is selected from a group consisting of alkyl, cycloalkyl, aryl or heteroaryl. Aryl or heteroaryl may optionally be substituted one or more times with groups or substituents such as alkyl, hydroxy, halogen, haloalkyl X is selected from O, (CH₂)p, NH; wherein p is selected from 0-2

In an even further embodiment, a composition may be provided having a composition according to Formula IV:

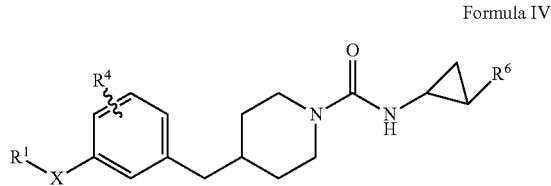

Formula IV its stereoisomers or pharmaceutically acceptable salts thereof;
wherein R¹ is selected from a group consisting of alkyl, hydrogen, haloalkyl, cycloalkyl, heterocycloalkyl, aryl, or heteroaryl and wherein R¹ may optionally be substituted one or more times with groups or substituents such as alkyl, hydroxy, halogen, haloalkyl, hydroxyalkyl, alkoxyalkyl, alkoxy, amine, SO₂R⁵, SO₂NHR², COR³

R² is selected from a group consisting of hydrogen, alkyl, haloalkyl, or cycloalkyl R³ is selected from a group consisting of alkyl, cycloalkyl, hydroxy, amine, alkylamine or alkoxy R⁴ is selected from a group consisting of hydrogen, alkyl, halogen, haloalkyl, hydroxy, amine, alkoxy, SO₂R⁵, COR³

R⁵ is selected from a group consisting of alkyl, haloalkyl, cycloalkyl, aryl or amine R⁶ is selected from a group consisting of alkyl, cycloalkyl, aryl or heteroaryl. Aryl or heteroaryl may optionally be substituted one or more times with groups or substituents such as alkyl, hydroxy, halogen, haloalkyl
X is selected from O, (CH$_2$)p, NH; wherein p is selected from 0-2
Further, the composition may comprise one or more of the following compounds, its stereoisomers or pharmaceutically acceptable salts thereof;
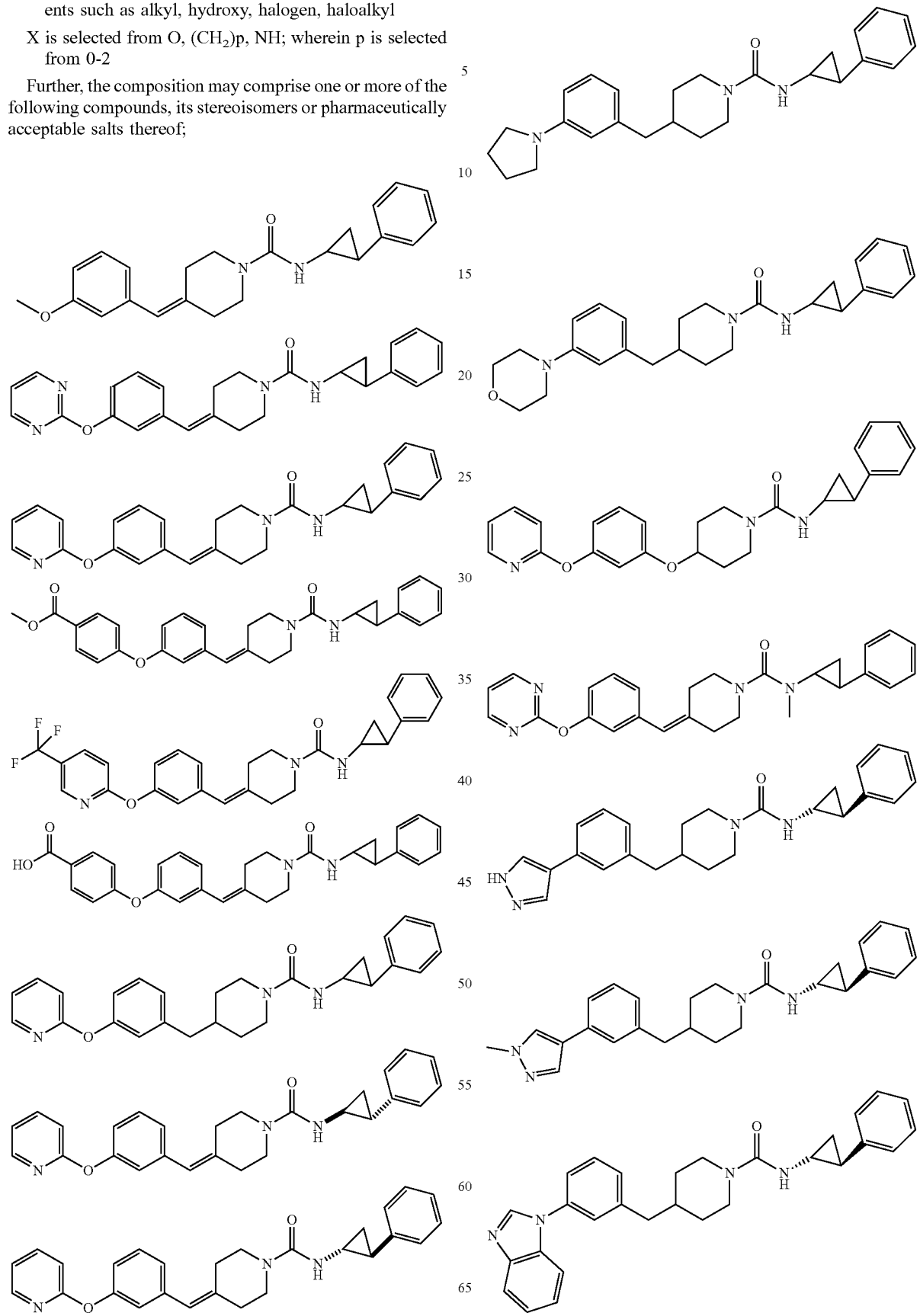

-continued

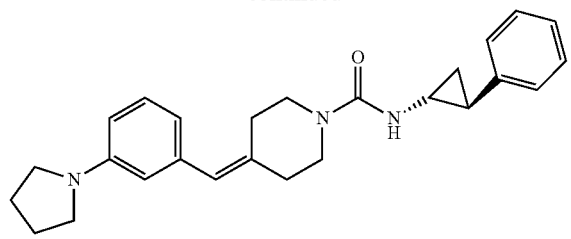
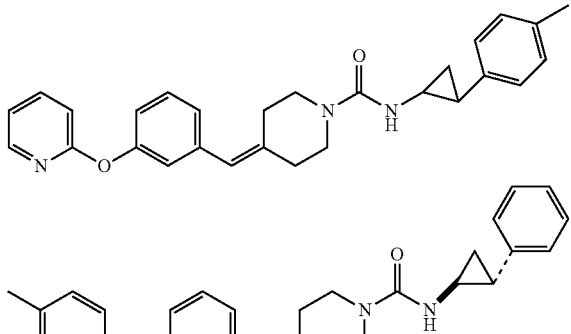
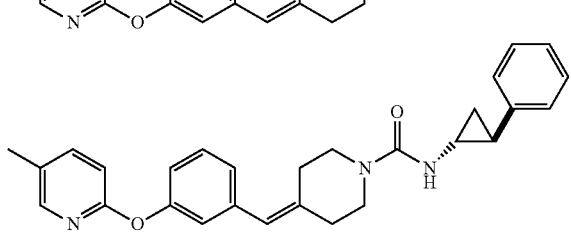
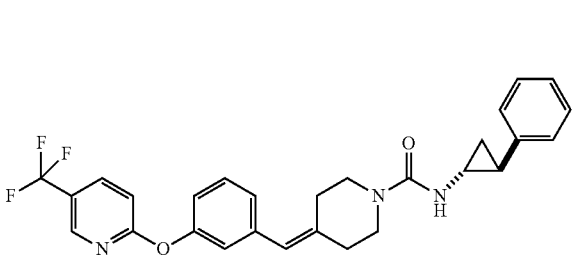
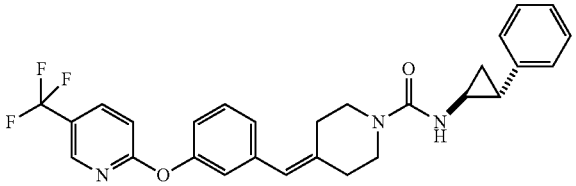
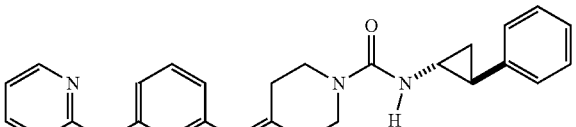
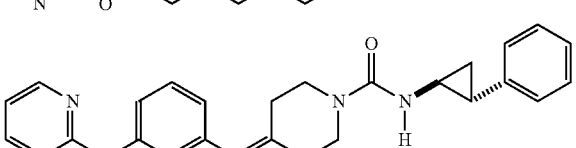
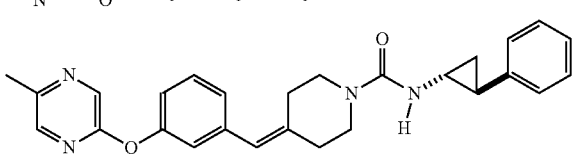

-continued

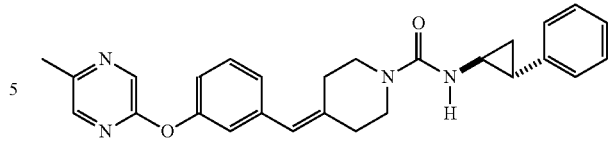
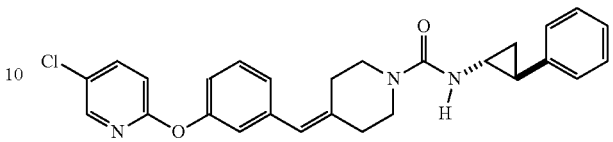
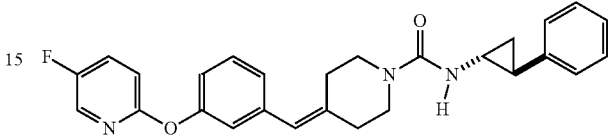
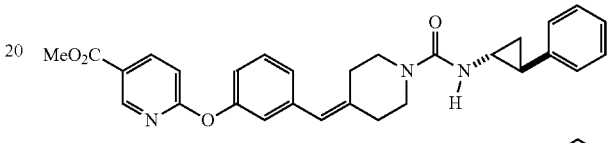
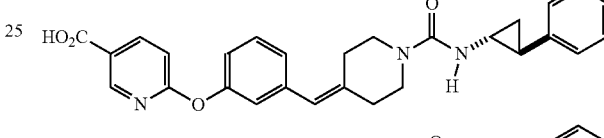
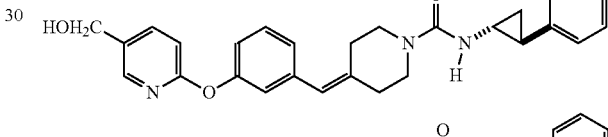
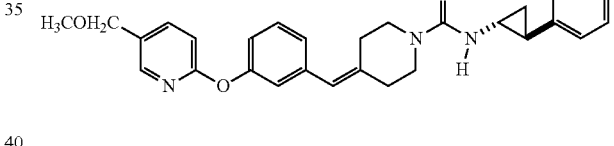

Further, the disclosure may provide a pharmaceutical composition comprising pharmaceutically acceptor carrier and at least one compound as shown herein.

In a still further embodiment, a method may be provided for the treatment of pain or neurodegenerative disease or other inflammatory disease in a subject in need of such treatment, the method comprising administering to the subject a therapeutically effective amount of at least one compound of Formula I:

Formula I

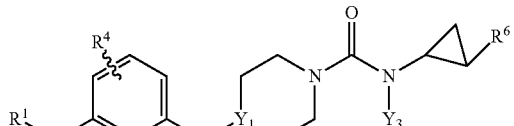

its stereoisomers or pharmaceutically acceptable salts thereof;

Still further, the method may include administrating to the subject a therapeutically effective amount of at least one compound according to Formula II for treatment of pain or neurodegenerative disease:

Formula II

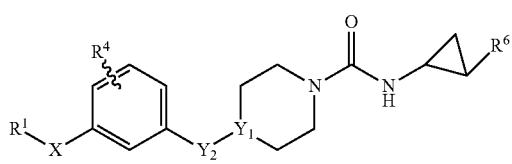

its stereoisomers or pharmaceutically acceptable salts thereof;

Yet further, the method may include administrating to the subject a therapeutically effective amount of at least one compound according to Formula III for treatment of pain or neurodegenerative disease:

Formula III

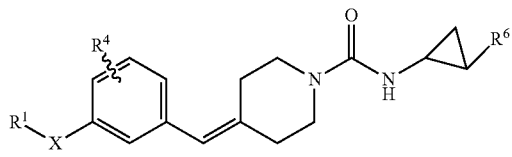

its stereoisomers or pharmaceutically acceptable salts thereof.

Further still, the method may include administrating to the subject a therapeutically effective amount of at least one compound according to Formula IV for treatment of pain or neurodegenerative disease:

Formula IV

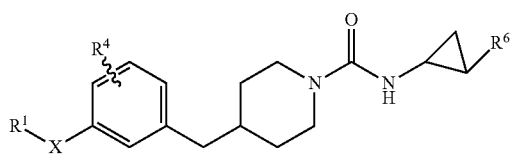

its stereoisomers or pharmaceutically acceptable salts thereof.

Still further, the method may include administrating to the subject a therapeutically effective amount of at least one compound for treatment of pain or neurodegenerative disease selected from one or more of:

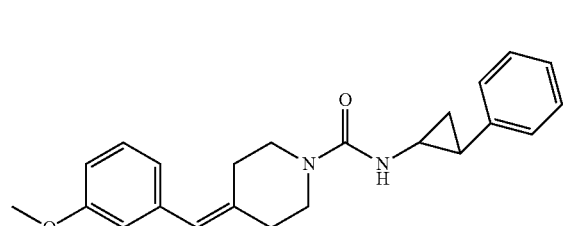

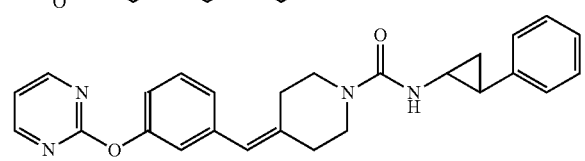

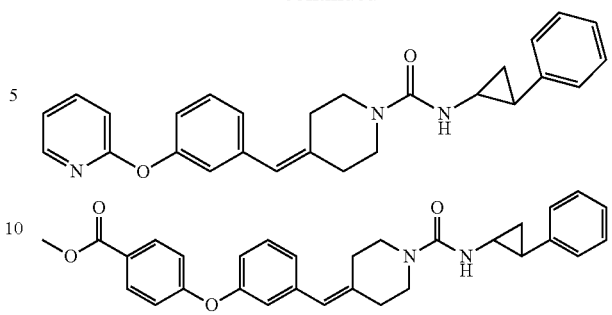

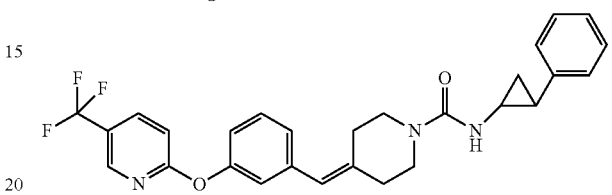

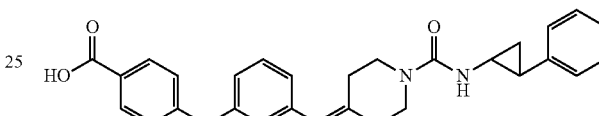

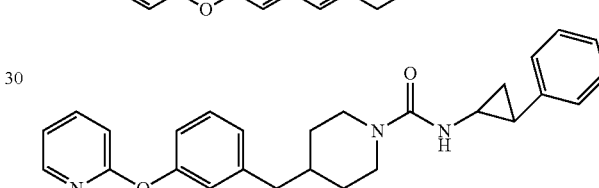

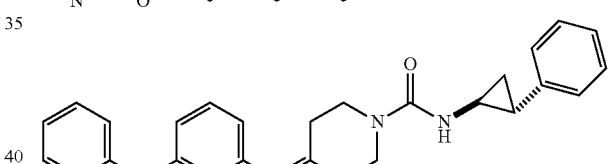

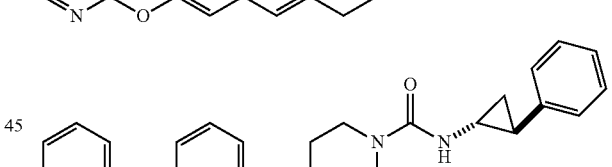

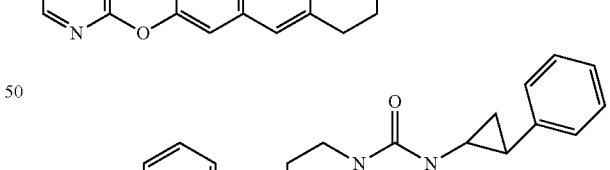

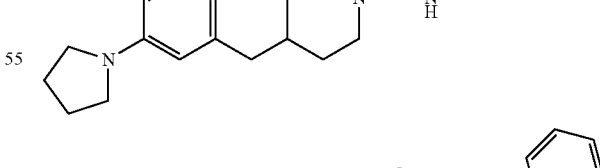

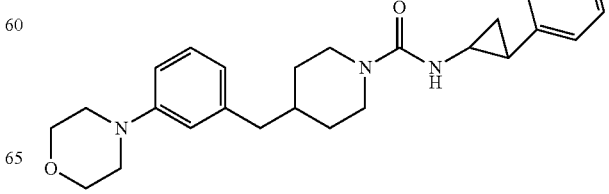

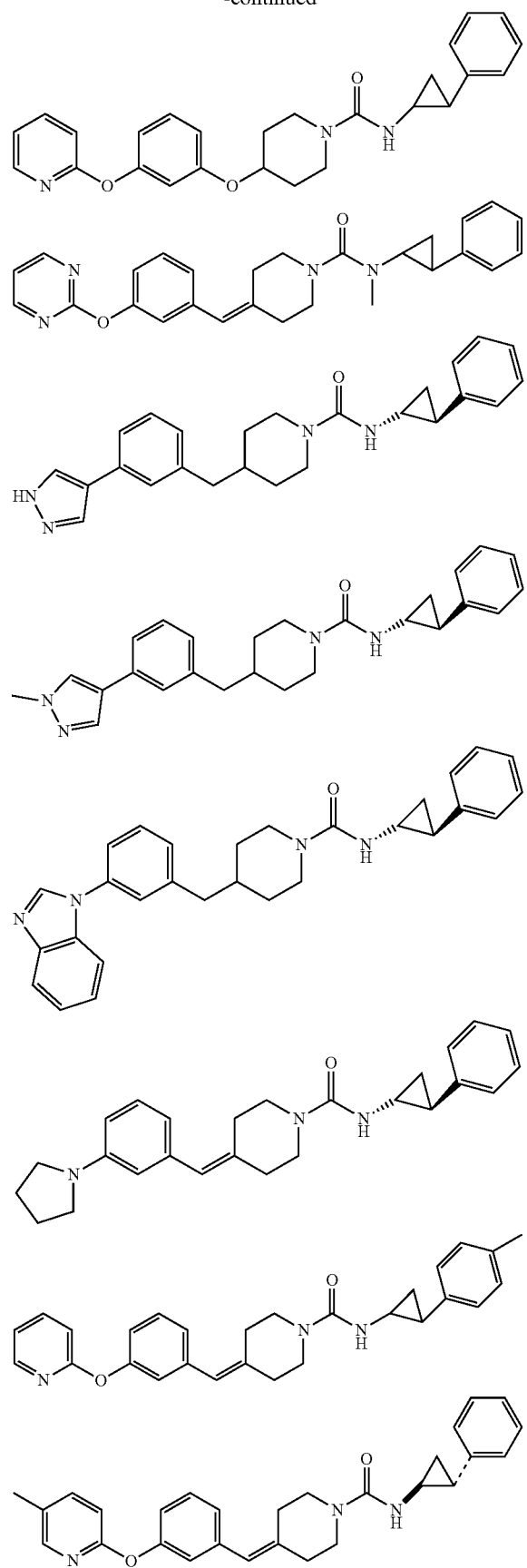
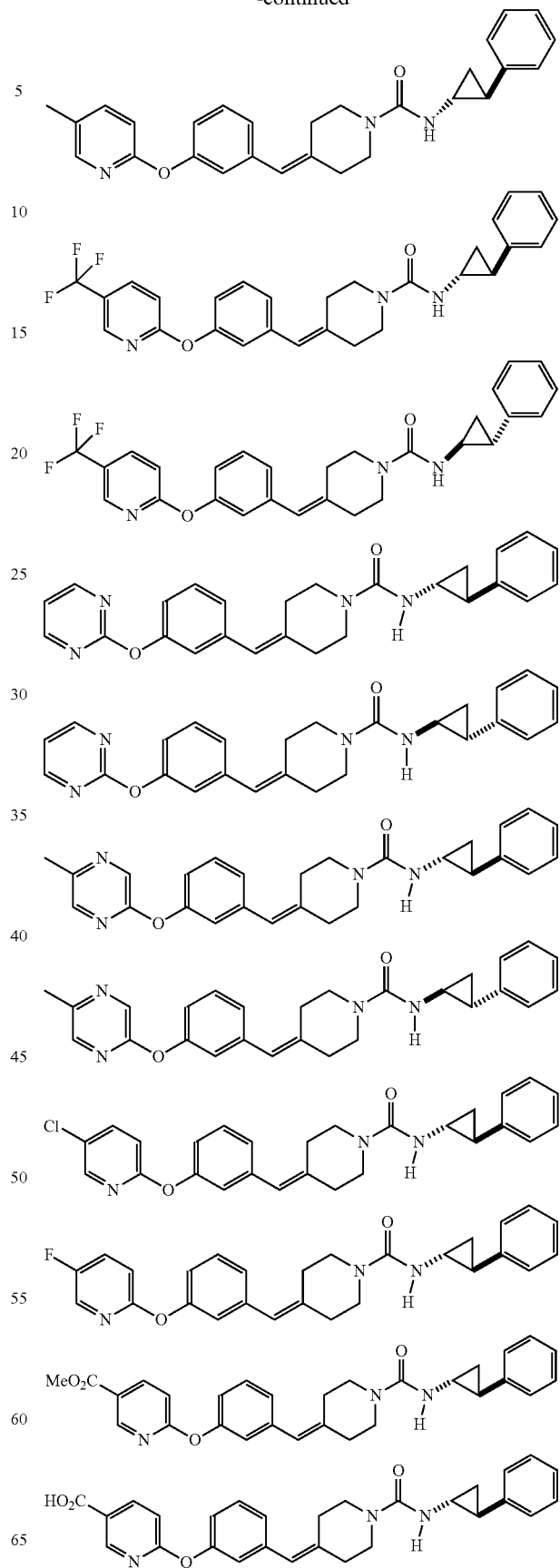

-continued

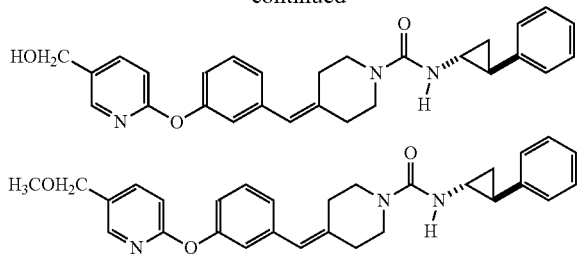

Even further, the disclosure may provide a method for the treatment of neuropathic or inflammatory pain in a subject in need of such treatment, the method comprising administering to the subject a therapeutically effective amount of a composition described herein.

Further yet, a method may be provided for the treatment of Parkinson's disease in a subject in need of such treatment, the method comprising administering to the subject a therapeutically effective amount of a composition described herein.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present disclosure will be obtained by reference to the following detailed description that sets forth illustrative embodiments, in which the principles of the disclosure may be utilized, and the accompanying drawings of which:

FIG. 1 shows Table 1, soluble epoxide hydrolase inhibitory potency of compounds of Formula I.

Figure 2:
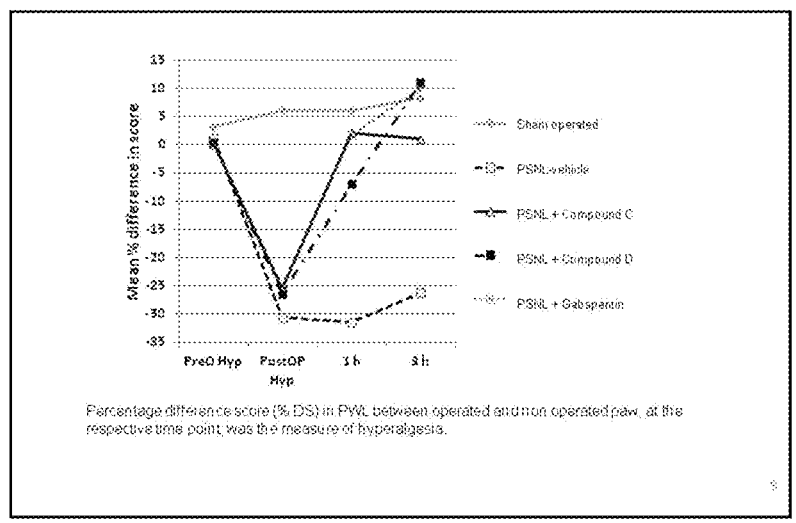
FIG. 2 shows efficacy of compounds of Formula I in a neuropathic pain model.

The figures herein are for illustrative purposes only and are not necessarily drawn to scale.

DETAILED DESCRIPTION OF THE EXAMPLE EMBODIMENTS

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by reference as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further embodiment includes from the one particular value and/or to the other particular value. The recitation of numerical ranges by endpoints includes all numbers and fractions subsumed within the respective ranges, as well as the recited endpoints. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +1-5% or less, +/−1% or less, and +/−0.1% or less of and from the specified value, insofar such variations are appropriate to perform in the disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, a "biological sample" may contain whole cells and/or live cells and/or cell debris. The biological sample may contain (or be derived from) a "bodily fluid". The present disclosure encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, and cell cultures from bodily fluids. Bodily fluids may be obtained from a mammal organism, for example by puncture, or other collecting or sampling procedures.

As used herein, "agent" refers to any substance, compound, molecule, and the like, which can be administered to a subject on a subject to which it is administered to. An agent can be inert. An agent can be an active agent. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein, "active agent" or "active ingredient" refers to a substance, compound, or molecule, which is biologically active or otherwise that induces a biological or physiological effect on a subject to which it is administered to. In other words, "active agent" or "active ingredient" refers to a component or components of a composition to which the whole or part of the effect of the composition is attributed.

As used herein, "administering" refers to any suitable administration for the agent(s) being delivered and/or subject receiving said agent(s) and can be oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition to the perivascular space and adventitia. For example, a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration routes can be, for instance, auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratym panic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/ or vaginal administration, and/or any combination of the above administration routes, which typically depends on the disease to be treated, subject being treated, and/or agent(s) being administered.

As used herein, "control" can refer to an alternative subject or sample used in an experiment for comparison purpose and included to minimize or distinguish the effect of variables other than an independent variable.

The term "optional" or "optionally" means that the subsequent described event, circumstance or substituent may or may not occur, and that the description includes instances where the event or circumstance occurs and instances where it does not.

As used herein, "dose," "unit dose," or "dosage" can refer to physically discrete units suitable for use in a subject, each unit containing a predetermined quantity of a pharmaceutical formulation calculated to produce the desired response or responses in association with its administration.

The term "molecular weight", as used herein, can generally refer to the mass or average mass of a material.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed by the term "subject".

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," can refer to an amount (e.g. mass, volume, dosage, concentration, and/or time period) needed to achieve one or more desired and/or stated result(s). For example, a therapeutically effective amount refers to an amount needed to achieve one or more therapeutic effects.

As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory or CD-ROM or on a server that can be accessed by a user via, e.g. a web interface.

As used herein, the terms "treating" and "treatment" can refer generally to obtaining a desired pharmacological and/ or physiological effect. The effect can be, but does not necessarily have to be, prophylactic in terms of preventing or partially preventing a disease, symptom or condition thereof, such as cancer and/or indirect radiation damage. The effect can be therapeutic in terms of a partial or complete cure of a disease, condition, symptom or adverse effect attributed to the disease, disorder, or condition. The term "treatment" as used herein covers any treatment of cancer and/or indirect radiation damage, in a subject, particularly a human and/or companion animal, and can include any one or more of the following: (a) preventing the disease or damage from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

"Halogen or Halo" means fluorine, chlorine, bromine or iodine.

"Alkyl" group means linear or branched alkyl groups. Exemplary alkyl groups include methyl, ethyl, n-propyl, iso-propyl, n-butyl, iso-butyl, t-butyl, n-pentyl, iso-pentyl, hexyl, heptyl, octyl and the like. Unless otherwise specified, an alkyl group typically has from about 1 to about 10 carbon atoms.

"Cycloalkyl" group means a cyclic alkyl group which may be mono or bicyclic. Exemplary cycloalkyl groups include cyclopropyl, cyclobutyl, cyclopentyl, cyclohexyl, cycloheptyl, cyclooctyl and the like. Unless otherwise specified, a cycloalkyl group typically has from about 3 to about 10 carbon atoms.

"Hlaloalkyl" group means linear or branched alkyl groups wherein at least one hydrogen is replaced by halogen or halo groups. Exemplary haloalkyl groups include trifluromethyl, chloroethyl, difluoromethyl, difluoroethyl, and the like.

Hydroxyalkyl" group means a linear monovalent hydrocarbon radical of one to three carbon atoms or a branched monovalent hydrocarbon radical of three to five carbons substituted with one or two hydroxy groups, provided that if two hydroxy groups are present they are not both on the same carbon atom. Representative examples include hydroxymethyl, 2-hydroxyethyl, 2-hydroxypropyl, 3-hydroxypropyl.

"Alkoxyalkyl" means a linear monovalent hydrocarbon radical of one to six carbon atoms or a branched monovalent hydrocarbon radical of three to six carbons substituted with an alkoxy group, as defined above, e.g., methoxymethyl, 2-methoxyethyl, 1-, 2-, or 3-methoxypropyl.

"Heterocycloalkyl" means a non-aromatic monocyclic or polycyclic ring comprising carbon and hydrogen atoms and at least one heteroatom, preferably, 1 to 4 heteroatoms selected from nitrogen, oxygen, and sulfur. A heterocycloalkyl group can have one or more carbon-carbon double bonds or carbon-heteroatoms double bonds in the ring as long as the ring is not rendered aromatic by their presence. Examples of heterocycloalkyl groups include pyrrolidinyl pyrrolidino, piperidinyl, piperidino, piperazinyl, piperazino, morpholinyl, morpholino, tetrahydrofuranyl, tetrahydropyranyl, and pyranyl.

"Alkoxy" means an —O (alkyl) group, where alkyl is as defined above. Exemplary alkoxyl groups include methoxy, ethoxy, propoxy, butoxy, iso-propoxy, iso-butoxy, and the like. Unless otherwise specified, an alkoxy group typically has from 1 to about 10 carbon atoms.

"Amine" refers to a primary, secondary, or tertiary amino group. The secondary and tertiary amine may contain alkyl, cycloalkyl or aryl substitutions. Some examples of amines include $NH_2$, NHMe, $NMe_2$ NH (cyclopropyl). Unless otherwise specified, the alkyl or cycloalkyl group on an amine typically has from 1 to about 8 carbon atoms.

"Aryl" means an optionally substituted monocyclic or polycyclic aromatic ring system of about 6 to about 14 carbon atoms. Exemplary aryl groups include phenyl, naphthyl, and the like. Unless otherwise specified, an aryl group typically has from 6 to about 14 carbon atoms.

"Heteroaryl" means an aromatic monocyclic or polycyclic ring system of about 4 to about 12 carbon atoms, having at least one heteroatom or hetero group selected from —O—, —N—, —S—, —$SO_2$, or —CO. Exemplary heteroaryl groups include one or more of pyrazinyl, isothiazolyl, oxazolyl, pyrazolyl, pyrrolyl, tetrazolyl, imidazolyl, triazolyl, pyridazinyl, thienopyrimidyl, furanyl, indolyl, isoindolyl, benzo[1,3]dioxolyl, benzimidazolyl, 1,3-benzoxathiolyl, pyrrolidine 2,4-dionyl, quinazolinyl, pyridyl, pyrimidinyl, thiophenyl and the like. Unless otherwise specified, a heteroaryl group typically has from 4 to about 10 carbon atoms.

"5- to 6-member heteroaryl" is an aromatic monocyclic ring system of 5 or 6 ring atoms, having at least one heteroatom or hetero group selected from —O—, —N—, —S—, —$SO_2$, or —CO. Exemplary "5- to 6-member heteroaryl" groups include one or more of pyrazinyl, isothiazolyl, oxazolyl, pyrazolyl, pyrrolyl, pyridazinyl, pyridyl, thienopyrimidyl, tetrazolyl, imidazolyl, triazolyl, furanyl and the like.

"Optionally substituted" means that substitution is optional and, therefore, it is possible for the designated atom or molecule to be unsubstituted. In the event a substitution is desired, then such substitution means that any number of hydrogens on the designated atom is replaced with a selection from the indicated group, provided that the normal valence of the designated atom is not exceeded, and that the substitution results in a sufficiently stable compound for use.

"Salts" refers to any acid or base salt, pharmaceutically acceptable solvates, or any complex of the compound that, when administered to a recipient, is capable of providing (directly or indirectly) a compound as described herein. It should be appreciated, however, that salts that are not pharmaceutically acceptable also lie within the scope of the disclosure. The preparation of salts can be carried out using known methods. For example, pharmaceutically acceptable salts of compounds contemplated herein as being useful may be synthesized by conventional chemical methods using a parent compound containing a base or an acid functionality. Generally, such salts may be prepared, for example, by making free acid or base forms of the compounds and reacting with a stoichiometric quantity of the appropriate base or acid in water or in an organic solvent, or in a mixture of the two. Generally, non-aqueous media such as one or more of solvents such as ether, ethyl acetate, ethanol, isopropanol or acetonitrile may be utilized. Examples of acid addition salts include one or more of mineral acid addition salts such as hydrochloride, hydrobromide, hydroiodide, sulphate, phosphate, and organic acid addition salts such as one or more of acetate, maleate, fumarate, citrate, oxalate, succinate, tartrate, malate, mandelate, methanesulphonate and p-toluenesulphonate. Examples of base addition salts include one or more of inorganic salts such as sodium, potassium, calcium, ammonium, magnesium, and lithium salts, and organic base salts such as one or more of ethylenediamine, ethanolamine, N,N-dialkyl-ethanolamine, triethanolamine, and basic amino acid salts.

The phrase "therapeutically-effective" indicates the capability of an agent or combination to prevent, or improve on the severity of, the disorder, while generally avoiding adverse side effects that would discourage the patient from taking the administered agent. The therapeutically effective compositions of the present disclosure may include compounds of the present disclosure at doses of from about 10 to about 3000 mg. The exact dosage amount can be determined based on a number of factors, including the patient's characteristics and the degree of treatment required.

As used herein, "therapeutically effective amount" means the dose or amount of a compound of the present disclosure administered to a subject and the frequency of administration to result in some therapeutic response. The dose or effective amount to be administered to a subject and the frequency of administration to the subject can be readily determined by one of ordinary skill in the art by the use of known techniques and by observing results obtained under analogous circumstances. In determining the effective amount or dose, a number of factors may be considered by the attending diagnostician, including, but not limited to, the potency and duration of action of the compounds used; the nature and severity of the illness to be treated as well as the sex, age, weight, general health and individual responsiveness of the subject to be treated, and other relevant circumstances.

The compounds described herein may be administered in admixture with one or more pharmaceutically acceptable excipients or carriers in the form of a pharmaceutical composition. A "composition" may contain one compound or a mixture of compounds. A "pharmaceutical composition" is any composition useful or potentially useful in producing physiological response in a subject to which such pharmaceutical composition is administered.

The term "pharmaceutically acceptable," with respect to an excipient, is used to define non-toxic substances generally suitable for use in human or animal pharmaceutical products. The pharmaceutical composition may be in the forms normally employed, such as tablets, capsules, powders, syrups, solutions, suspensions, and the like. The pharmaceutical composition may contain flavorants, sweeteners, etc., in suitable solid or liquid carriers or diluents, or in suitable sterile media to form injectable solutions or suspensions. Such compositions typically contain from about 0.1 to about 50%, and in some embodiments, from about 1 to about 20%, by weight of active compound, the remainder of the composition being pharmaceutically acceptable carriers, diluents or solvents.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the disclosure. For example, in the appended claims, any of the claimed embodiments can be used in any combination.

All patents, patent applications, published applications, and publications, databases, websites and other published materials cited herein are hereby incorporated by reference to the same extent as though each individual publication, published patent document, or patent application was specifically and individually indicated as being incorporated by reference.

Kits

Any of the compounds and/or formulations described herein can be presented as a combination kit. As used herein, the terms "combination kit" or "kit of parts" refers to the compounds, compositions, formulations, particles, cells and any additional components that are used to package, sell, market, deliver, and/or administer the combination of elements or a single element, such as the active ingredient, contained therein. Such additional components include, but are not limited to, packaging, syringes, blister packages, bottles, and the like. When one or more of the compounds, compositions, particles, cells, described herein or a combination thereof (e.g., agent(s)) contained in the kit are administered simultaneously, the combination kit can contain the active agent(s) in a single formulation, such as a pharmaceutical formulation, (e.g., a tablet, liquid preparation, dehydrated preparation, etc.) or in separate formulations. When the compounds, compositions, formulations, particles, and cells described herein or a combination thereof and/or kit components are not administered simultaneously, the combination kit can contain each agent or other component in separate pharmaceutical formulations. The separate kit components can be contained in a single package or in separate packages within the kit.

In some embodiments, the combination kit also includes instructions printed on or otherwise contained in a tangible medium of expression. The instructions can provide information regarding the content of the compounds and/or formulations, safety information regarding the content of the compounds and formulations (e.g., pharmaceutical formulations), information regarding the dosages, indications for use, and/or recommended treatment regimen(s) for the compound(s) and/or pharmaceutical formulations contained therein. In some embodiments, the instructions can provide directions and protocols for administering the compounds and/or formulations described herein to a subject in need thereof. In some embodiments, the instructions can provide one or more embodiments of the methods for administration of the pharmaceutical formulation thereof such as any of the methods described in greater detail elsewhere herein.

DETAILED DESCRIPTION OF THE DISCLOSURE

Reference will now be made in detail to the embodiments of the disclosure, one or more examples of which are set forth below. Each example is provided by way of explanation of the disclosure, not a limitation of the disclosure. In fact, it will be apparent to those skilled in the art that various modifications can be made in the present disclosure without departing from the scope or spirit of the disclosure. For instance, features illustrated or described as part of one embodiment can be used on another embodiment to yield a still further embodiment. Thus it is intended that the present disclosure cover such modifications and variations as come within the scope of the appended claims and their equivalents. Other objects, features, and aspects of the present disclosure are disclosed in, or are obvious from, the following detailed description.

For ease of reference, the present disclosure will be described in terms of administration to human subjects. It will be understood, however, that such descriptions are not limited to administration to humans, but will also include administration to other animals unless explicitly stated otherwise.

Contemplated derivatives are those that may improve dissolution or increase the bioavailability of the compounds of this disclosure when such compounds are administered to a subject (e.g., by making an orally administered compound more easily absorbed). Compounds of Formula I may be amorphous, semi-crystalline, or crystalline and may either be given as parent compounds, its salts, and/or in solvated form. The solvate may be part of crystalline lattice or superficially associated. It is intended that all of these forms should be within the scope of the present disclosure. Methods of solvation are generally known within the art. Suitable solvates are pharmaceutically acceptable solvates. In one embodiment, the solvate is a hydrate.

In one aspect, the present disclosure is directed to novel compounds of Formula I:

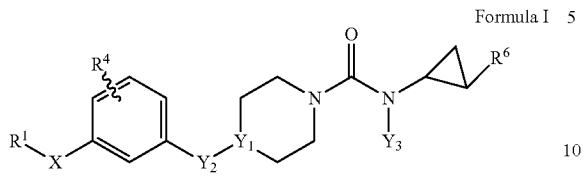

Formula I its stereoisomers or pharmaceutically acceptable salts thereof;

Wherein $R^1$ is selected from a group consisting of alkyl, hydrogen, haloalkyl, cycloalkyl, heterocycloalkyl, aryl, or heteroaryl and wherein $R^1$ may optionally be substituted one or more times with groups or substituents such as alkyl, hydroxy, halogen, haloalkyl, hydroxyalkyl, alkoxyalkyl, alkoxy, amine, $SO_2NHR^2$, $COR^3$ $R^2$ is selected from a group consisting of hydrogen, alkyl, haloalkyl, or cycloalkyl $R^3$ is selected from a group consisting of alkyl, cycloalkyl, hydroxy, amine, alkyamine or alkoxy $R^4$ is selected from a group consisting of hydrogen, alkyl, halogen, haloalkyl, hydroxy, amine, alkoxy, $SO_2R^5$, $COR^3$ $R^5$ is selected from a group consisting of alkyl, haloalkyl, cycloalkyl, aryl or amine $R^6$ is selected from a group consisting of alkyl, cycloalkyl, aryl or heteroaryl. Aryl or heteroaryl may optionally be substituted one or more times with groups or substituents such as alkyl, hydroxy, halogen, haloalkyl X is selected from O, $(CH_2)p$, NH; wherein p is selected from 0-2 and $Y_1$-$Y_2$ are selected from $CH_2$—$CH_2$, $CH_2$—O, or CH=CH; however, when $Y_1$-$Y_2$ is $CH_2$—O, X is selected from O or NH and $R^1$ is not hydrogen $Y_3$ is selected from H or Me In another aspect, the present disclosure is directed to novel compounds of Formula II:

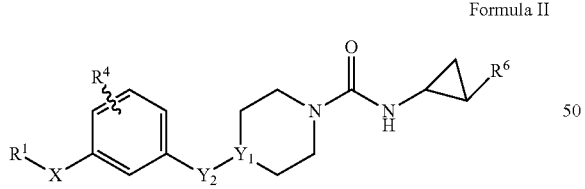

Formula II its stereoisomers or pharmaceutically acceptable salts thereof;

wherein $R^1$ is selected from a group consisting of alkyl, hydrogen, haloalkyl, cycloalkyl, heterocycloalkyl, aryl, or heteroaryl and wherein $R^1$ may optionally be substituted one or more times with groups or substituents such as alkyl, hydroxy, halogen, haloalkyl, hydroxyalkyl, alkoxyalkyl, alkoxy, amine, $SO_2NHR^2$, $COR^3$ $R^2$ is selected from a group consisting of hydrogen, alkyl, haloalkyl, or cycloalkyl $R^3$ is selected from a group consisting of alkyl, cycloalkyl, hydroxy, amine, alkyamine or alkoxy $R^4$ is selected from a group consisting of hydrogen, alkyl, halogen, haloalkyl, hydroxy, amine, alkoxy, $SO_2R^5$, $COR^3$ $R^5$ is selected from a group consisting of alkyl, haloalkyl, cycloalkyl, aryl or amine $R^6$ is selected from a group consisting of alkyl, cycloalkyl, aryl or heteroaryl. Aryl or heteroaryl may optionally be substituted one or more times with groups or substituents such as alkyl, hydroxy, halogen, haloalkyl X is selected from O, $(CH_2)p$, NH; wherein p is selected from 0-2 and $Y_1$-$Y_2$ are selected from $CH_2$—$CH_2$, $CH_2$—O, or CH=CH; however, when $Y_1$-$Y_2$ is $CH_2$—O, X is selected from O or NH and $R^1$ is not hydrogen.

In another aspect, the present disclosure is directed to novel compounds of Formula III:

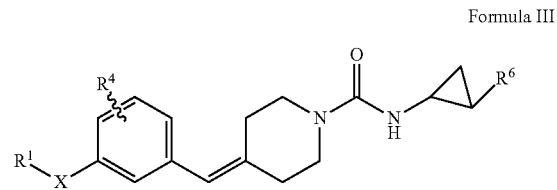

Formula III its stereoisomers or pharmaceutically acceptable salts thereof;

wherein $R^1$ is selected from a group consisting of alkyl, hydrogen, haloalkyl, cycloalkyl, heterocycloalkyl, aryl, or heteroaryl and wherein $R^1$ may optionally be substituted one or more times with groups or substituents such as alkyl, hydroxy, halogen, haloalkyl, hydroxyalkyl, alkoxyalkyl, alkoxy, amine, $SO_2R^5$, $SO_2NHR^2$, $COR^3$ $R^2$ is selected from a group consisting of hydrogen, alkyl, haloalkyl, or cycloalkyl $R^3$ is selected from a group consisting of alkyl, cycloalkyl, hydroxy, amine, alkyamine or alkoxy $R^4$ is selected from a group consisting of hydrogen, alkyl, halogen, haloalkyl, hydroxy, amine, alkoxy, $SO_2R^5$, $COR^3$ $R^5$ is selected from a group consisting of alkyl, haloalkyl, cycloalkyl, aryl or amine $R^6$ is selected from a group consisting of alkyl, cycloalkyl, aryl or heteroaryl. Aryl or heteroaryl may optionally be substituted one or more times with groups or substituents such as alkyl, hydroxy, halogen, haloalkyl X is selected from O, $(CH_2)p$, NH; wherein p is selected from 0-2

In another aspect, the present invention is directed to novel compounds of Formula IV:

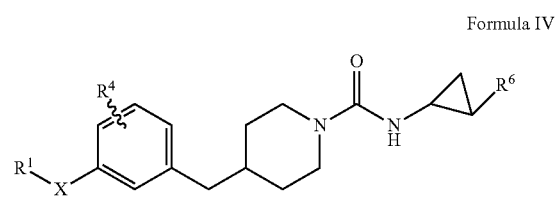

Formula IV its stereoisomers or pharmaceutically acceptable salts thereof;
wherein
R¹ is selected from a group consisting of alkyl, hydrogen, haloalkyl, cycloalkyl, heterocycloalkyl, aryl, or heteroaryl and wherein R¹ may optionally be substituted one or more times with groups or substituents such as alkyl, hydroxy, halogen, haloalkyl, hydroxyalkyl, alkoxyalkyl, alkoxy, amine, $SO_2R^5$, $SO_2NHR^2$, $COR^3$
R² is selected from a group consisting of hydrogen, alkyl, haloalkyl, or cycloalkyl
R³ is selected from a group consisting of alkyl, cycloalkyl, hydroxy, amine, alkyamine or alkoxy
R⁴ is selected from a group consisting of hydrogen, alkyl, halogen, haloalkyl, hydroxy, amine, alkoxy, $SO_2R^5$, $COR^3$
R⁵ is selected from a group consisting of alkyl, haloalkyl, cycloalkyl, aryl or amine
R⁶ is selected from a group consisting of alkyl, cycloalkyl, aryl or heteroaryl. Aryl or heteroaryl may optionally be substituted one or more times with groups or substituents such as alkyl, hydroxy, halogen, haloalkyl
X is selected from O, $(CH_2)p$, NH; wherein p is selected from 0-2

Further, the composition may comprise one or more of the following compounds, its stereoisomers or pharmaceutically acceptable salts thereof;

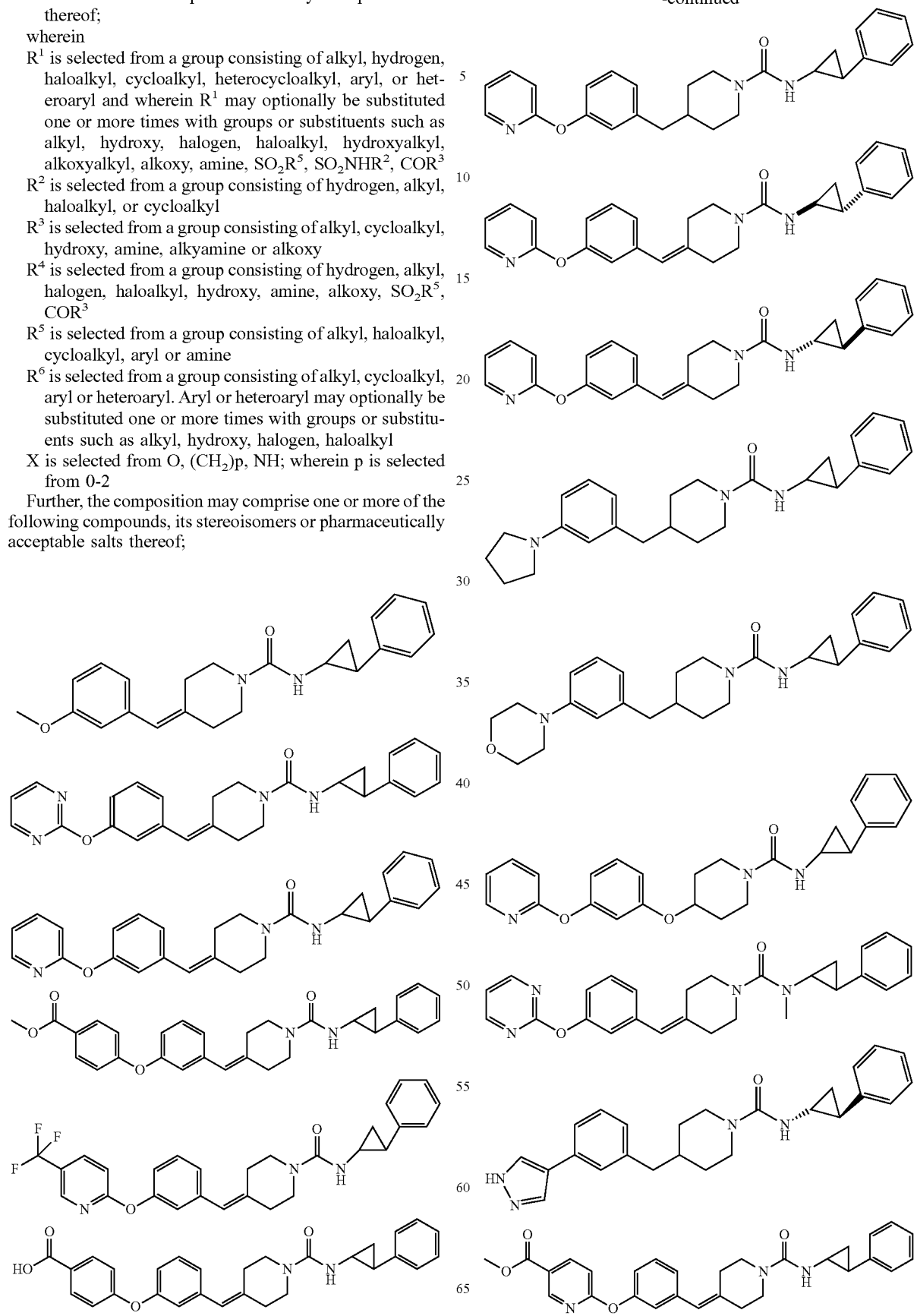

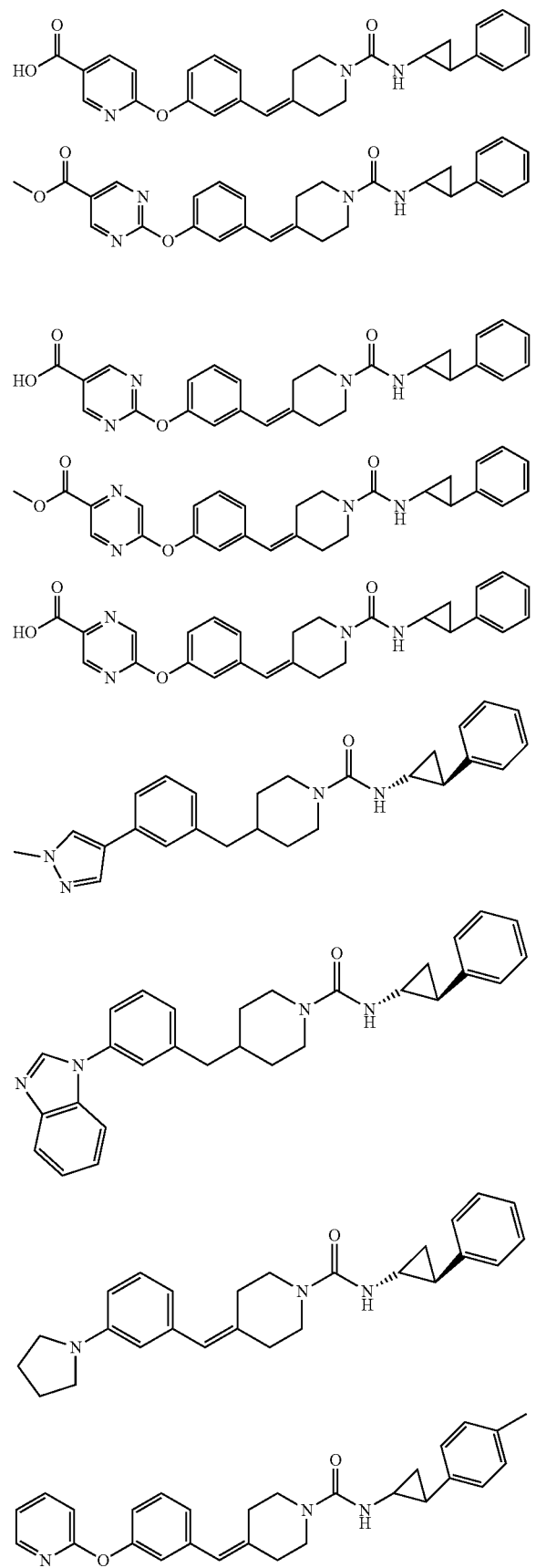
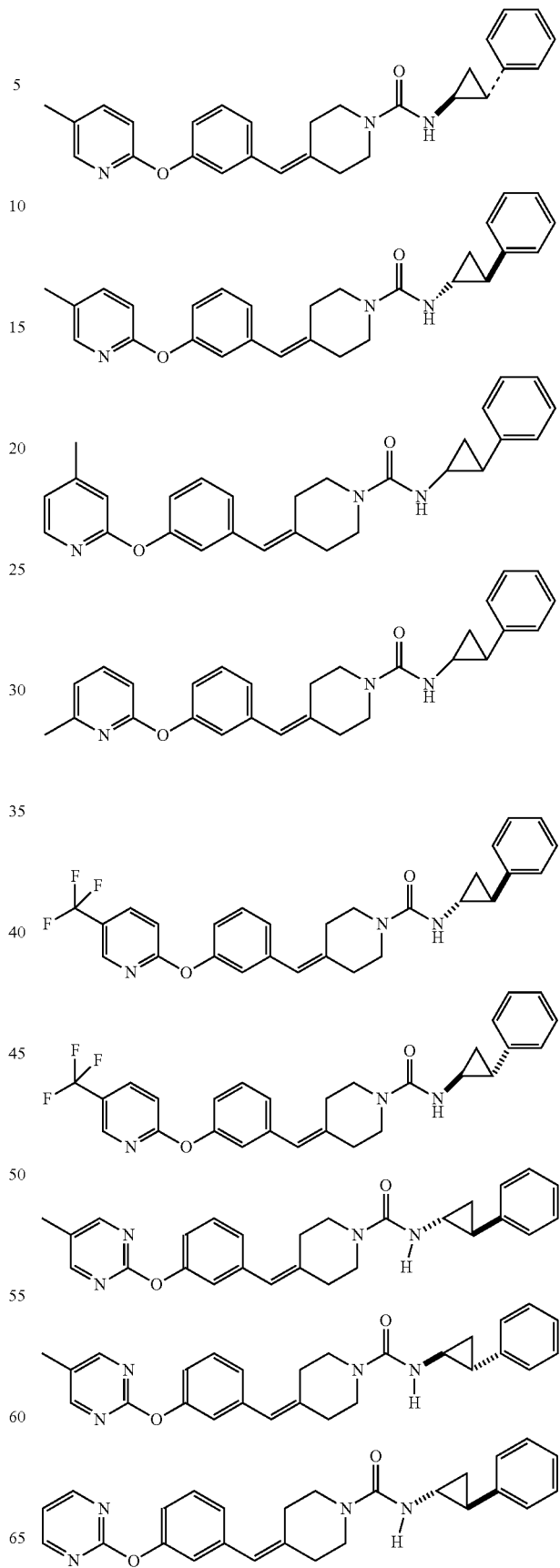

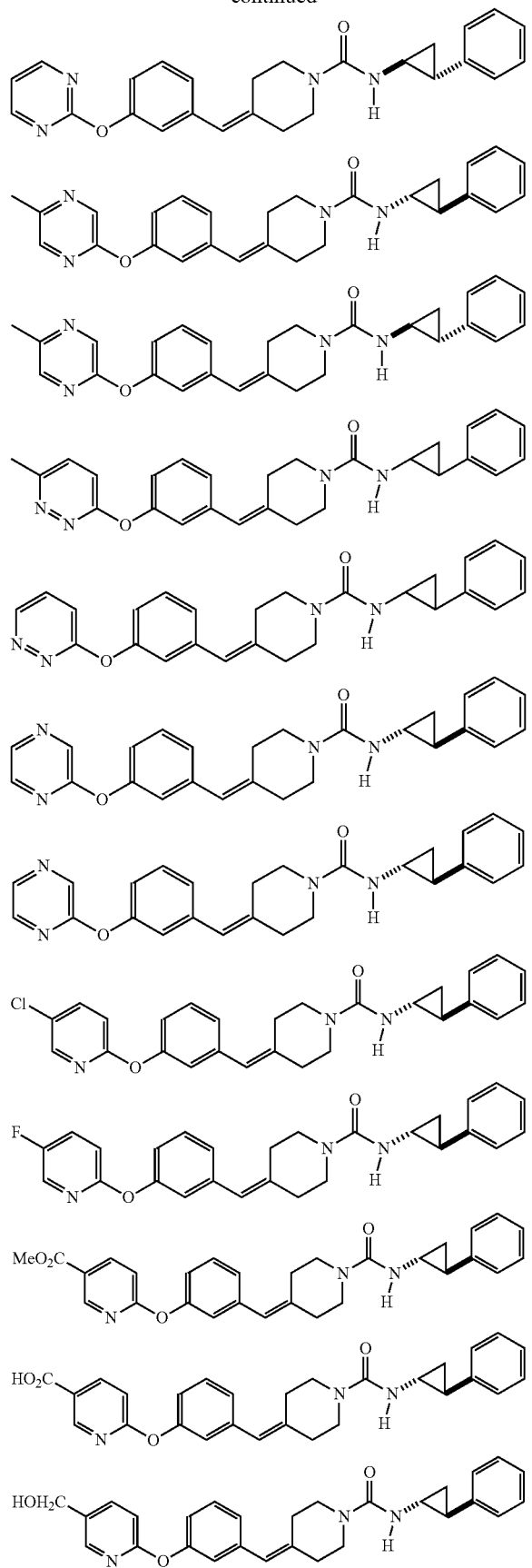

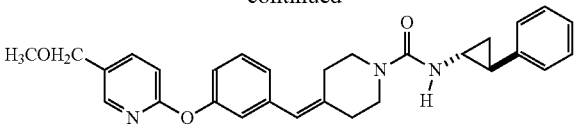

In yet another aspect, the disclosure is directed to novel compounds of Formula I, its stereoisomers, tautomers and/or its pharmaceutically acceptable salts thereof which can be used as inhibitors of soluble epoxide hydrolase (sEH).

In another aspect, the disclosure is directed to a method for the prevention and/or treatment of pain, neurodegenerative diseases and inflammatory disorders in a subject in need of such treatment, the method comprising administering to the subject a therapeutically effective amount of a compound of Formula I, its stereoisomers and/or its pharmaceutically acceptable salts thereof. Still, the compounds of Formula I, its stereoisomers and/or pharmaceutically acceptable salts may be used for the prevention or treatment of diabetic peripheral neuropathy, chemotherapy-induced neuropathy, post-herpetic neuralgia, trigeminal neuralgia, fibromyalgia, and other neuropathic or inflammatory pain conditions.

Further still, the compounds of Formula I may optionally be combined with one or more anti-inflammatory or analgesic drugs such as cox-2 inhibitors, NSAIDs, pregabalin, gabapentin or opioids and then administered to a subject for the treatment of inflammatory and/or pain conditions.

In another embodiment, the stereoisomers and/or pharmaceutically acceptable salts of Formula I may be used for the treatment of neurodegenerative diseases such as Parkinson's disease.

For ease of reference, the present disclosure will be described in terms of administration to human subjects. It will be understood, however, that such descriptions are not limited to administration to humans, but will also include administration to other animals unless explicitly stated otherwise.

Contemplated derivatives are those that may improve dissolution or increase the bioavailability of the compounds of this disclosure when such compounds are administered to a subject (e.g., by making an orally administered compound more easily absorbed). Compounds of Formula I may be amorphous, semi-crystalline, or crystalline and may either be given as parent compounds, its salts, and/or in solvated form. The solvate may be part of crystalline lattice or superficially associated. It is intended that all of these forms should be within the scope of the present disclosure. Methods of solvation are generally known within the art. Suitable solvates are pharmaceutically acceptable solvates. In one embodiment, the solvate is a hydrate.

In one embodiment, compounds of the present disclosure (those of Formula I) are useful for the treatment of inflammatory pain, neuropathic pain, rheumatoid arthritis, osteoarthritis, diabetic nephropathy, hypertension, diabetes, and/or metabolic syndrome. The compounds of Formula I may be useful in elevating epoxyeicosatrienoic acids (EETs) levels in a subject to prevent and treat inflammatory and/or pain conditions.

Compounds of Formula I, their pharmaceutically acceptable salts, and/or solvates thereof can, therefore, be used in the prevention and/or treatment of a disease or condition discussed herein. Pharmaceutical compositions containing a therapeutically effective quantity of a compound of Formula I, its pharmaceutically acceptable salts, and/or solvates thereof, possibly together with pharmaceutically acceptable excipients, are additional aspects of the present disclosure.

The therapeutically effective quantity of compounds of Formula I, their pharmaceutically acceptable salts and/or solvates that must be administered, and the dosage for treating a pathological state with said compounds, will depend on numerous factors, including age, the state of the patient, the severity of the disease, the route and frequency of administration, the modulator compound to be used, etc.

Suitable pharmaceutically acceptable carriers may include solid fillers or diluents and sterile aqueous or organic solutions. The active ingredient may be present in such pharmaceutical compositions in the amounts sufficient to provide the desired dosage in the range as described above. Thus, for oral administration, the active ingredient may be combined with a suitable solid or liquid carrier or diluent to form capsules, tablets, powders, syrups, solutions, suspensions and the like. For parenteral administration, the active ingredient can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. Aqueous solutions with the active ingredient dissolved in pharmaceutically acceptable solvents such as polyhydroxylated castor oil may also be used for injectable solutions. The injectable solutions prepared in this manner can then be administered intravenously, intraperitoneally, subcutaneously, or intramuscularly, with intramuscular administration being generally preferred for humans.

The following examples describe exemplary embodiments of the disclosure. Other embodiments within the scope of the claims herein will be apparent to one skilled in the art from consideration of the specification or practice of the disclosure as disclosed herein. It is intended that the specification, together with the examples, be considered to be exemplary only, with the scope and spirit of the disclosure being indicated by the claims which follow the examples.

General Synthetic Procedures

Compounds of present disclosure can be synthesized by following the procedures outlined in Schemes I-VIII. The suggested methodologies are not intended to be limiting. Variations of these synthetic methodologies or the methodologies reported in literature can be adopted to synthesize compounds within the scope of disclosure.

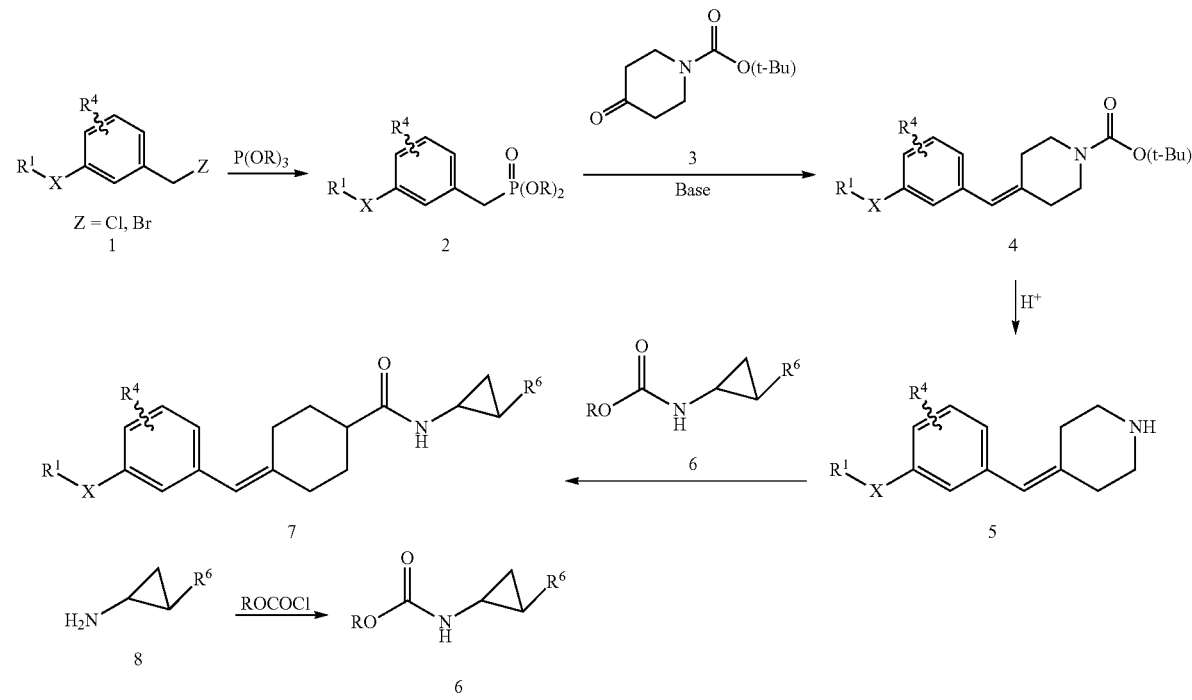

Scheme I $R^1$ = alkyl, haloalkyl, aryl, heteroaryl, cycloalkyl, or heterocycloalkyl
$R^4$ = alkyl, halogen, haloalkyl, alkoxy, $SO_2R_5$, $COR_3$
$R^6$ = alkyl, cycloalkyl, aryl or heteroaryl
$X = O, (CH_2)_p, p = 0.-2$ Scheme I shows method of synthesis of compounds 7 of Formula I of the present disclosure. In the first step, substituted benzyl halide 1 (Z=Cl, Br) is reacted with trialkyl phosphate to yield substituted benzyl phosphonate 2. This reaction may be carried out by heating 1 with trialkyl phosphate at 120-150° C. with or without solvent such as dimethylacetamide for 10-20 h. The substituted alkene 4 is synthesized by generating ylid from the intermediate 2 and reacting with substituted piperidone 3. The formation of ylid from 2 may be carried using a base such as sodium hydride or potassium hydride in presence of a crown ether in a solvent such as THF, dimethoxyethane, or diethyl ether. This reaction may be initiated at low temperature (0±5° C.), followed by warming of reaction mixture to approximately 20° C. and stirring for additional 20-60 minutes. The reaction between ylid generated from 2 with 3 may be carried out in a solvent such as THF, dimethoxyethane, diethyl ether or toluene and initiating the reaction at low temperature (0±5° C.), followed by warming of reaction mixture to approximately 20-40° C. and stirring for 8-20 h. Deprotection of carbamate from 4 in presence of acid yields piperidine intermediate 5. This reaction may be carried out in a solvent such dichloromethane or dichloroethane and using acid such as trifluoroacetic acid by stirring reaction mixture at temperature of 0-25° C. for 20-90 minutes. Reaction of 5 with substituted cyclopropane carbamate intermediate 6 gives the target compound 7. This reaction may be carried out using a solvent such as dimethyl sulfoxide or dimethylacetamide and a base such as triethylamine, diisopropylethylamine by heating the reaction components at 40-60° C. over a period of 3-6 h.

The substituted cyclopropane carbamate 6 may be synthesized from corresponding cyclopropylamine 8 by reacting with aryl chloroformate (R=Ph, or Ar) using solvent such as dichloromethane and a base such as diisopropylethylamine. The reaction may be initiated at low temperature (0±5° C.), followed by warming of reaction mixture to approximately 20-30° C. and stirring for 20-40 minutes. The substituted benzyl halide 1 and the substituted piperidone 3 used in Scheme I may be purchased commercially or synthesized from easily accessible reagents.

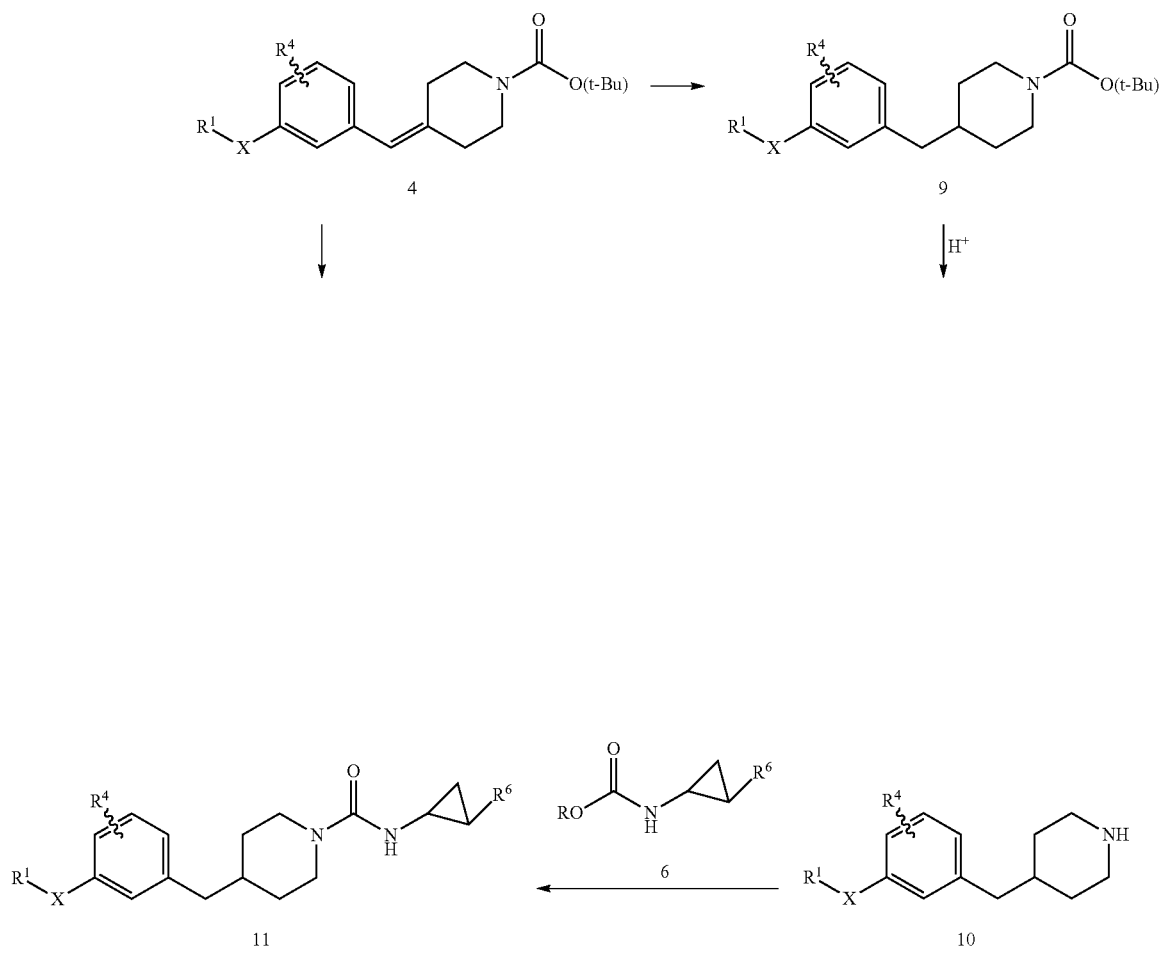

Scheme II $R^1$ = alkyl, haloalkyl, aryl, heteroaryl, cycloalkyl, or heterocycloalkyl
$R^4$ = alkyl, halogen, haloalkyl, alkoxy, $SO_2R_5$, $COR_3$
$R^6$ = alkyl, cycloalkyl, aryl or heteroaryl
$X = O, (CH_2)_p, p = 0.-2$ Scheme II shows a method of synthesis of compounds 11 of Formula I of the present disclosure. In the first step, compound 4 is synthesized using methodology described in Scheme I is hydrogenated to yield saturated compound 9. This reaction may be carried out using catalytic hydrogenation (using e.g.; Pd/C or Pt/C) in solvents such as methanol or ethanol in a Parr hydrogenation apparatus. Deprotection of the carbamate 9 in presence of an acid yields piperidine intermediate 10. This reaction may be carried out in a solvent such dichloromethane or dichloroethane and using acid such as trifluoroacetic acid by stirring reaction mixture at temperature of 0-25° C. for 20-90 minutes. Reaction of 10 with substituted cyclopropane carbamate intermediate 6 gives the target compound 11. This reaction may be carried out using a solvent such as dimethyl sulfoxide or dimethylacetamide and a base such as triethylamine, diisopropylethylamine by heating the reaction components at 40-60° C. over a period of 3-6 h.

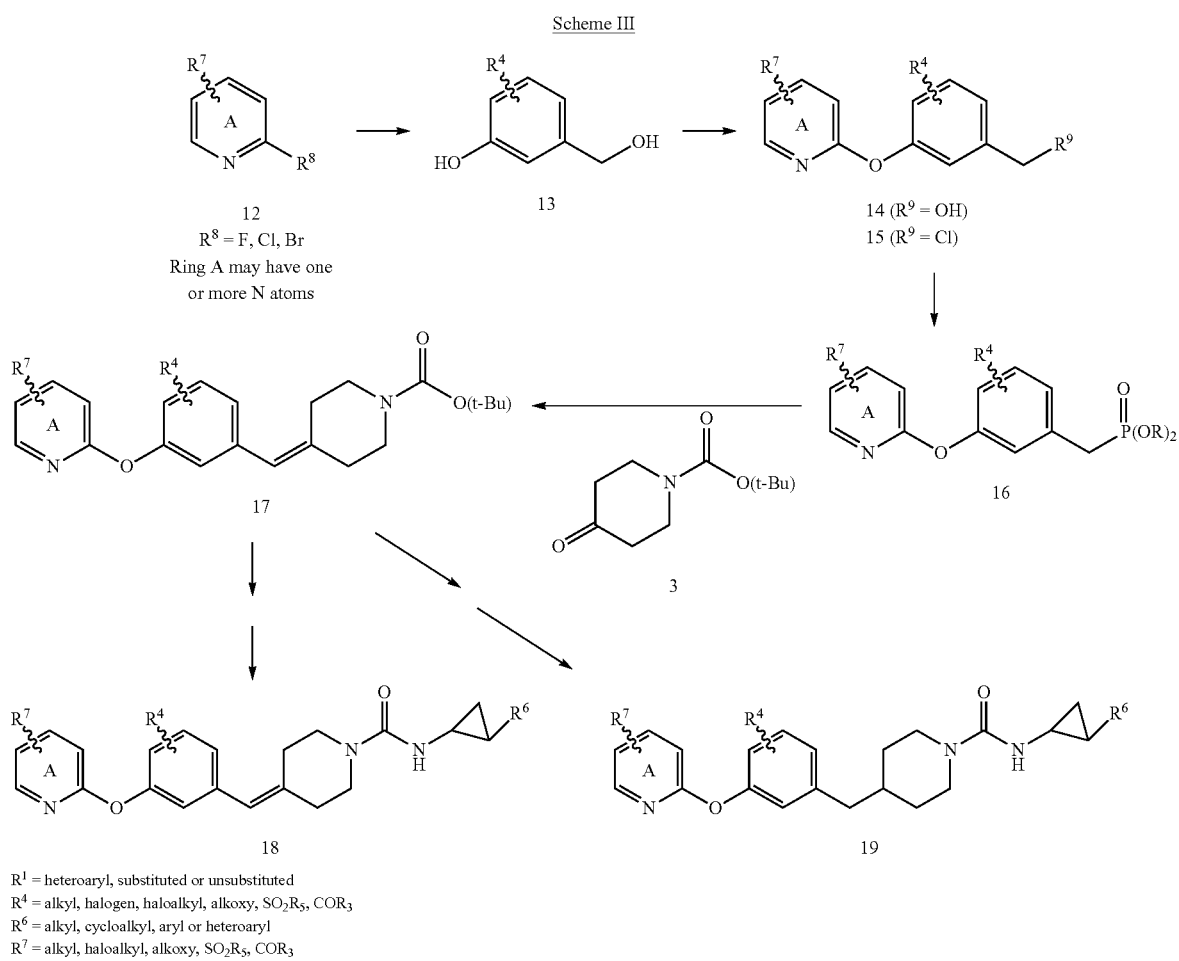

Scheme III $R^1$ = heteroaryl, substituted or unsubstituted
$R^4$ = alkyl, halogen, haloalkyl, alkoxy, $SO_2R_5$, $COR_3$
$R^6$ = alkyl, cycloalkyl, aryl or heteroaryl
$R^7$ = alkyl, haloalkyl, alkoxy, $SO_2R_5$, $COR_3$ Scheme III shows method of synthesis of compounds 18 and 19 of the present disclosure. In the first step, compound 12 containing heteroaryl ring A (such as pyridine, pyrimidine, pyrazine) reacts with substituted phenol 13 to yield 14. This reaction may be carried out in a solvent such as dimethylacetamide, or dimethylformamide using a base such as potassium carbonate, sodium carbonate, or cesium carbonate and by heating the reaction mixture at 80-120° C. for 3-6 h. The resulting substituted benzyl alcohol is converted to corresponding benzyl halide 15 by reaction with thionyl chloride. This reaction may be carried out using solvent such as dichloromethane and treating with thionyl chloride at 0-25° C. for 1-3 h. Substituted benzyl halide 15 is reacted with trialkyl phosphate to yield substituted benzyl phosphonate 16. This reaction may be carried out by heating 15 with trialkyl phosphate at 120-150° C. with or without solvent such as dimethylacetamide for 10-20 h. The substituted alkene 17 is synthesized by generating ylid from the intermediate 16 and reacting with substituted piperidone 3. The formation of ylid from 16 may be carried using a base such as sodium hydride or potassium hydride in presence of a crown ether in a solvent such as THF, dimethoxyethane, or diethyl ether. The reaction may be initiated at low temperature (0±5° C.), followed by warming of reaction mixture to approximately 20° C. and stirring for additional 20-60 minutes. The reaction between ylid generated from 16 with 3 may be carried out in a solvent such as THF, dimethoxyethane, diethyl ether or toluene and initiating the reaction at low temperature (0±5° C.), followed by warming of reaction mixture to approximately 20-40° C. and stirring for 8-20 h. Conversion of 17 to 18 may be carried out following steps of deprotection of carbamate in presence of acid and reaction with substituted cyclopropane carbamate intermediate 6 as described in Scheme I. Conversion of 17 to 19 may be accomplished using sequential steps involving hydrogenation, deprotection of carbamate and reaction with substituted cyclopropane carbamate intermediate 6 as described in Scheme II.

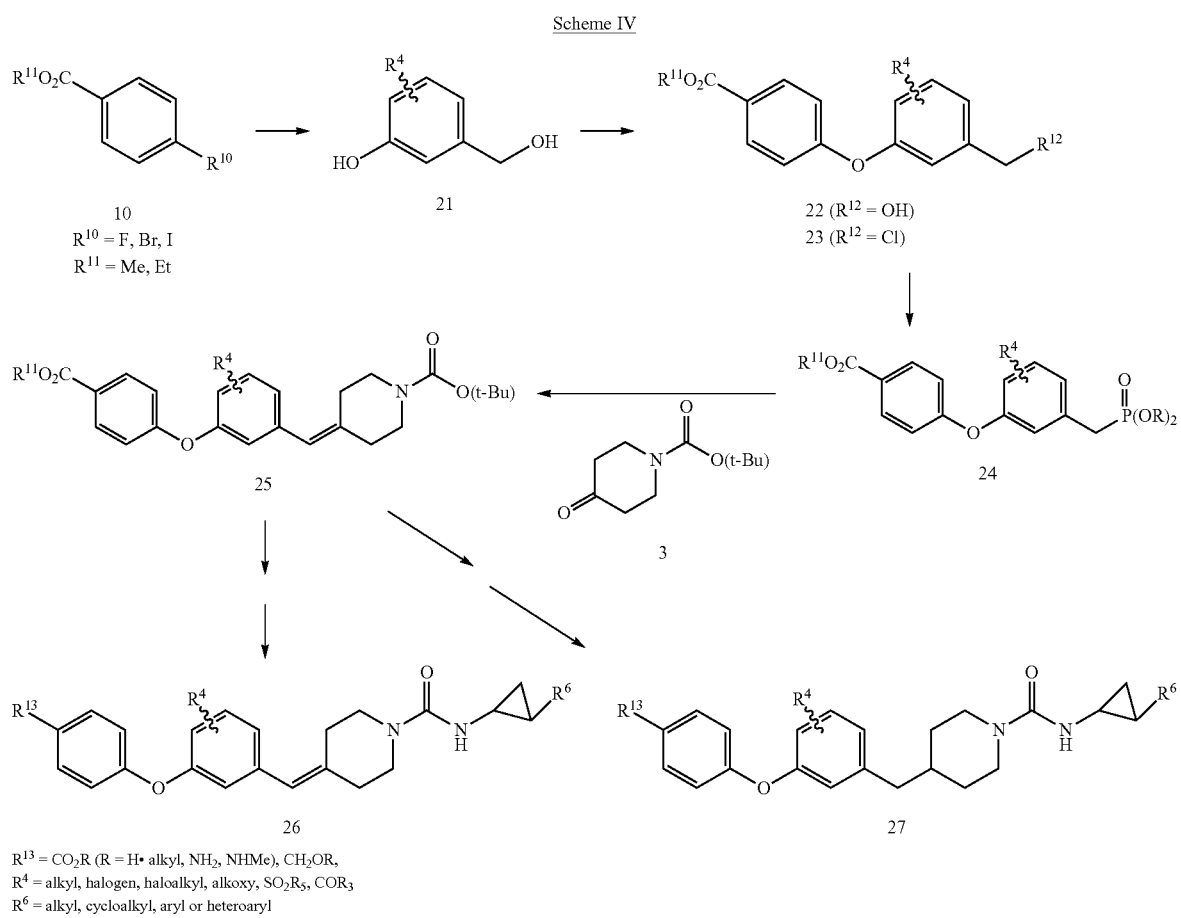

Scheme IV

Scheme IV shows method of synthesis of compounds 26 and 27 of the present disclosure. In the first step, compound 20 reacts with substituted phenol 21 to yield 22. This reaction may be carried out in a solvent such as dimethylacetamide or dimethylformamide using a base such as cesium carbonate by heating the reaction mixture at 80-120° C. for 3-8 h. The resulting substituted benzyl alcohol is converted to corresponding benzyl halide 23 by reaction with thionyl chloride. This reaction may be carried out using solvent such as dichloromethane and treating with thionyl chloride at 0-25° C. for 1-3 h. Substituted benzyl halide 23 is reacted with trialkyl phosphate to yield substituted benzyl phosphonate 24. This reaction may be carried out by heating 23 with trialkyl phosphate at 120-150° C. with or without solvent such as dimethylacetamide for 10-20 h. The substituted alkene 25 is synthesized by generating ylid from the intermediate 24 and reacting with substituted piperidone 3. The formation of ylid from 24 may be carried using a base such as sodium hydride or potassium hydride in presence of a crown ether in a solvent such as THF, dimethoxyethane, or diethyl ether. The reaction may be initiated at low temperature (0±5° C.), followed by warming of reaction mixture to approximately 20° C. and stirring for additional 20-60 minutes. The reaction between ylid generated from 24 with 3 may be carried out in a solvent such as THF, dimethoxyethane, diethyl ether or toluene and initiating the reaction at low temperature (0±5° C.), followed by warming of reaction mixture to approximately 20-40° C. and stirring for 8-20 h. Conversion of 25 to 26 may be carried out following steps of deprotection of carbamate in presence of acid and reaction with substituted cyclopropane carbamate intermediate 6 as described in Scheme I. Conversion of 25 to 27 may be accomplished using sequential steps involving hydrogenation, deprotection of carbamate and reaction with substituted cyclopropane carbamate intermediate 6 as described in Scheme II.

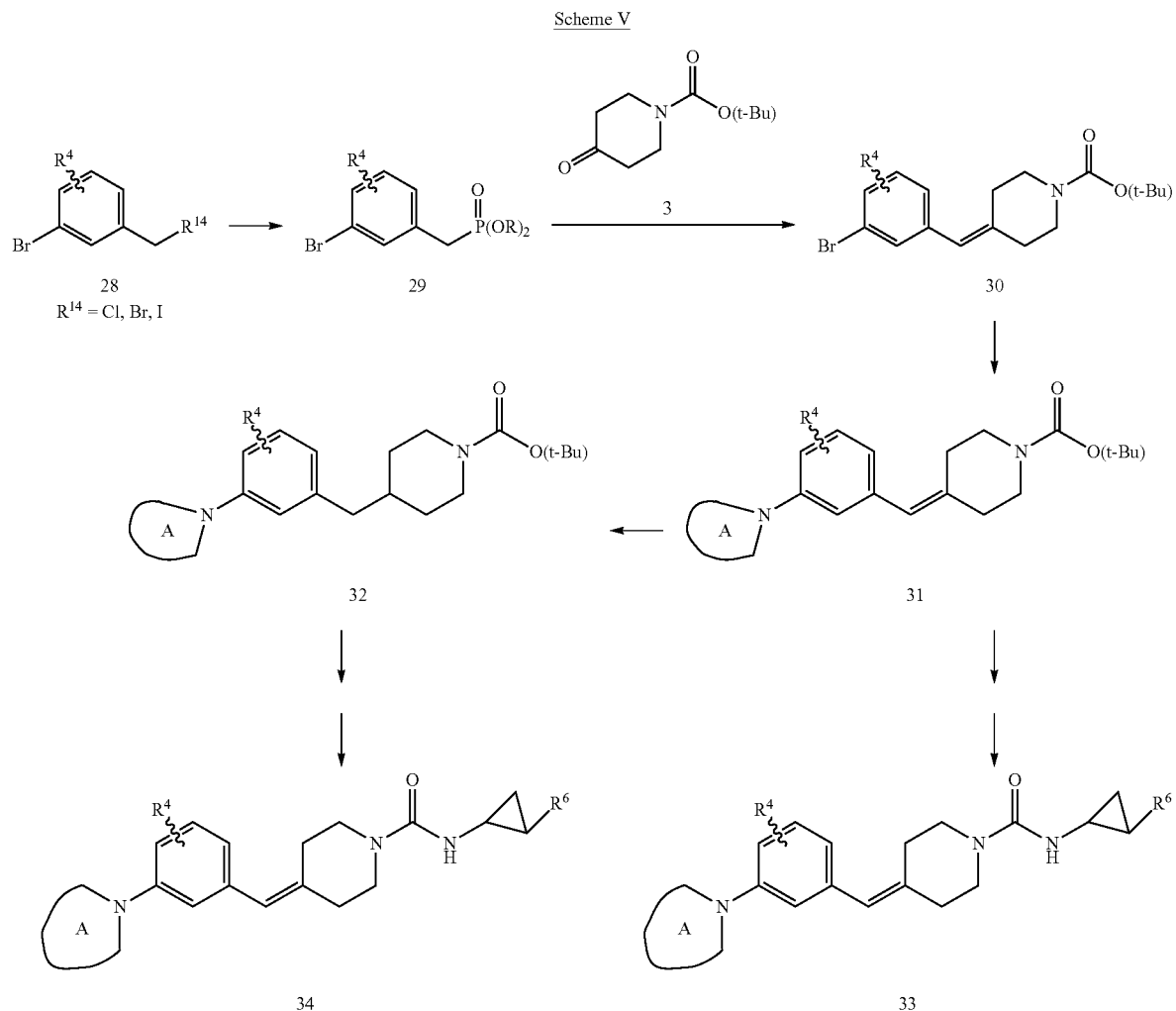

Scheme V shows method of synthesis of compounds 33 and 34 of the present disclosure. In the first step, substituted benzyl halide 28 is reacted with trialkyl phosphate to yield substituted benzyl phosphonate 29. This reaction may be carried out by heating 28 with trialkyl phosphate at 120-150° C. with or without solvent such as dimethylacetamide for 10-20 h. The substituted alkene 30 is synthesized by generating ylid from the intermediate 29 and reacting with substituted piperidone 3. The formation of ylid from 29 may be carried using a base such as sodium hydride or potassium hydride in presence of a crown ether in a solvent such as THF, dimethoxyethane, or diethyl ether. The reaction may be initiated at low temperature (0±5° C.), followed by warming of reaction mixture to approximately 20° C. and stirring for additional 20-60 minutes. The reaction between ylid generated from 29 with 3 may be carried out in a solvent such as THF, dimethoxyethane, diethyl ether or toluene and initiating the reaction at low temperature (0±5° C.), followed by warming of reaction mixture to approximately 20-40° C. and stirring for 8-20 h. The intermediate 31 containing heterocyclyl ring A is synthesized from 30 by reacting with corresponding heterocycle such as pyrrolidine, morpholine, piperidine. This reaction may be carried out by treating 30 with ring A heterocycle using cesium carbonate and catalysts such as palladium acetate and 2,2'-bis(diphenylphosphino)-1,1'-binaphthy (BINAP). The reaction may be carried out using solvents such as 1,4-dioxane by treating the reaction mixture at 20-100° C. for 5-20 h. Conversion of 31 to 33 may be carried out following steps of deprotection of carbamate in presence of acid and reaction with substituted cyclopropane carbamate intermediate 6 as described in Scheme I.

Conversion of 31 to 32 may be accomplished using catalytic hydrogenation (Pd/C, $H_2$) as described in Scheme II. Similarly, conversion of 32 to 34 may be carried out following methodology involving deprotection of carbamate and reaction with substituted cyclopropane carbamate intermediate 6 as described in Scheme II.

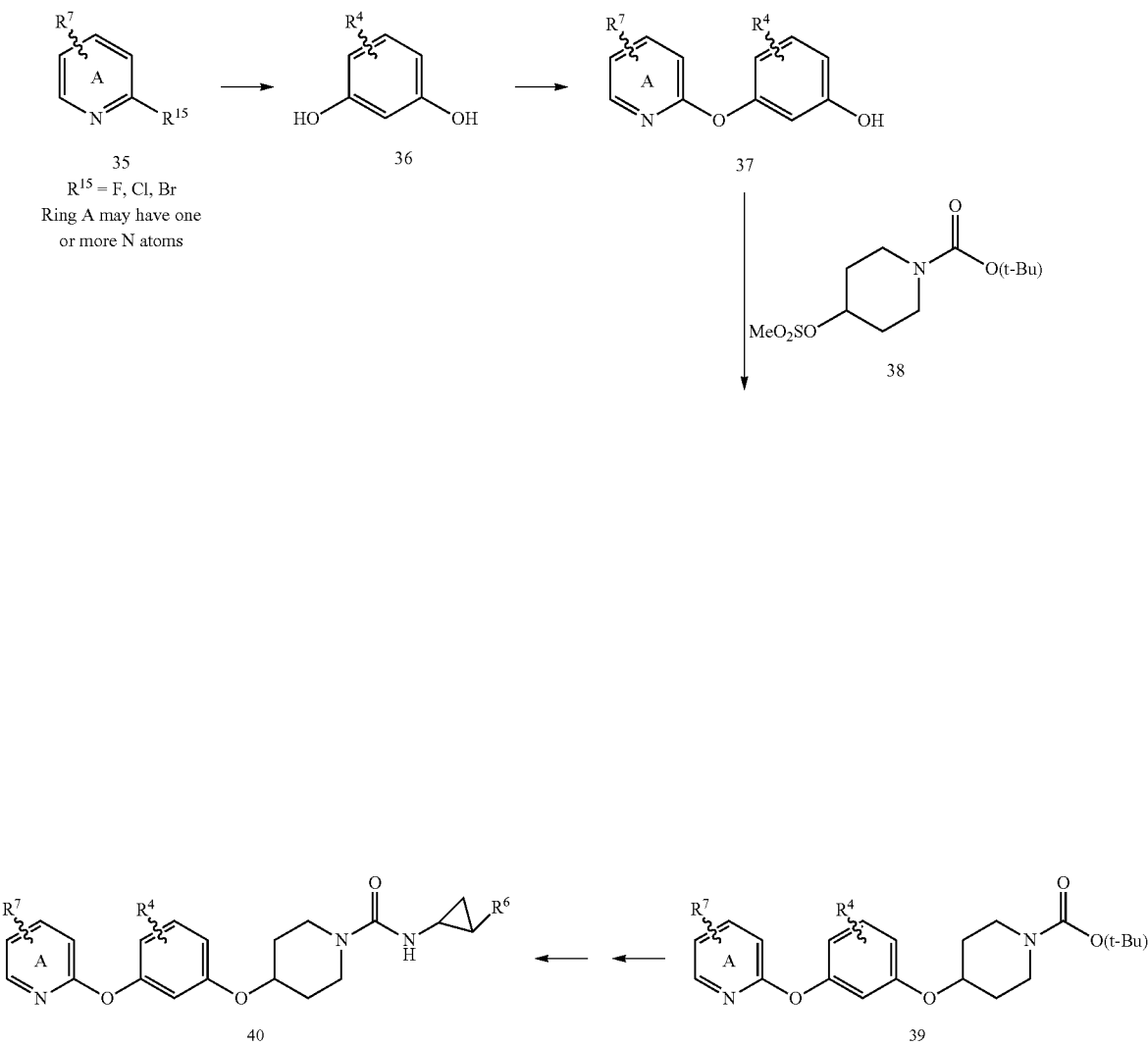

Scheme VI

Scheme VI shows a method of synthesis of compounds 40 of the present disclosure. In the first step, compound 35 containing heteroaryl ring A (such as pyridine, pyrimidine, pyrazine) reacts with substituted phenol 36 to yield 37. This reaction may be carried out in a solvent such as dimethylacetamide or dimethylformamide using a base such as potassium carbonate, sodium carbonate, or cesium carbonate by heating the reaction mixture at 80-120° C. for 3-8 h. Substituted phenol 37 is reacted with piperidine mesylate 38 to yield 39. This reaction may be carried out in a solvent such as dimethylacetamide, or dimethylformamide using a base such as potassium carbonate, sodium carbonate, cesium carbonate and heating the reaction mixture at 60-80° C. for 6-8 h. Conversion of 39 to 40 may be carried out following steps of deprotection of carbamate in presence of acid and reaction with substituted cyclopropane carbamate intermediate 6 as described in Scheme I.

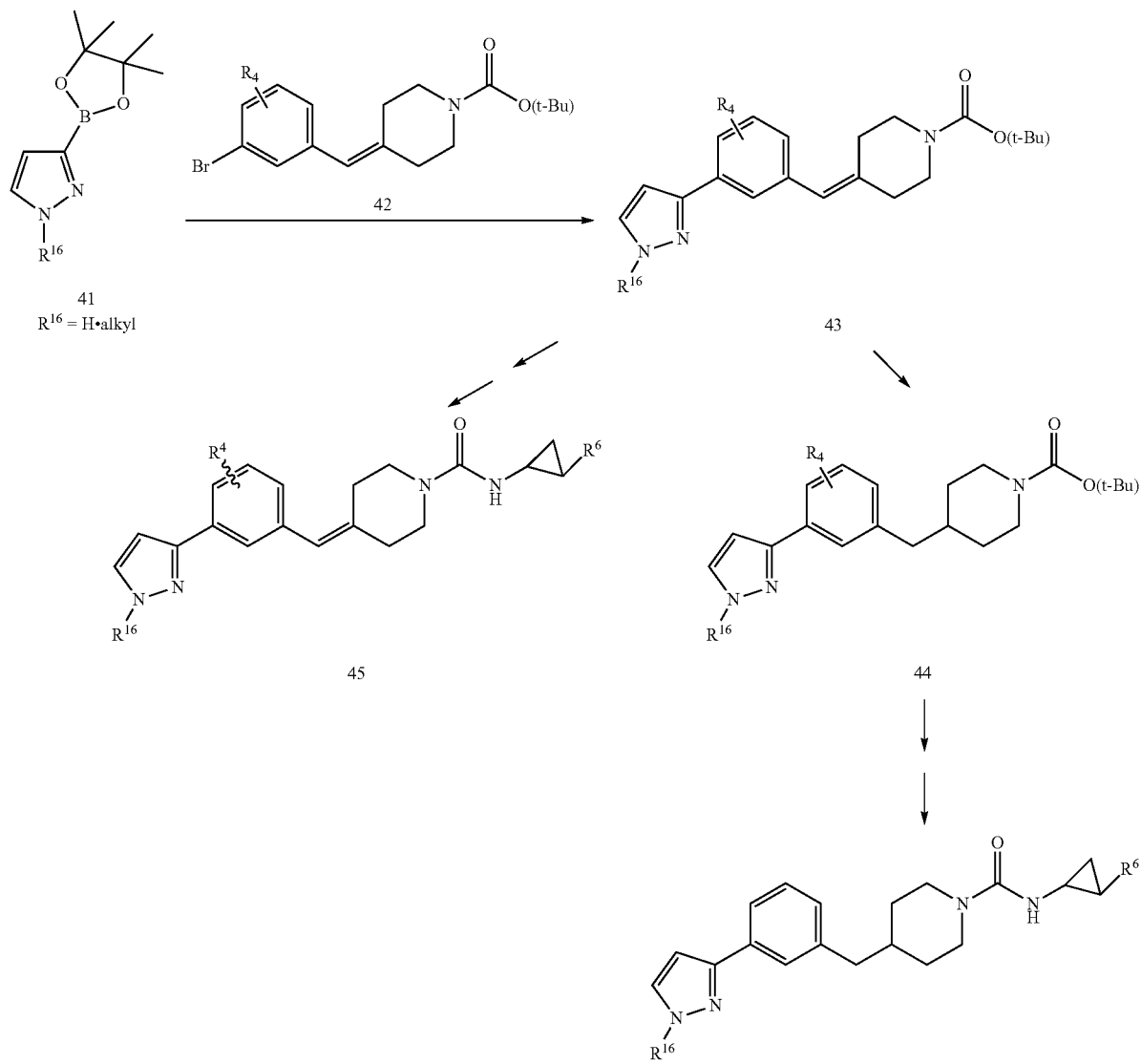

Scheme VII $R^4$ = alkyl, halogen, haloalkyl, alkoxy, $SO_2R_5$, $COR_3$
$R^6$ = alkyl, cycloalkyl, aryl or heteroaryl Scheme VII shows method of synthesis of compounds of formula 45 and 46 of the present disclosure. In the first step, compound 41 containing heteroaryl boronate reacts with aryl halide 42 to yield 43. This reaction may be carried out by treating 41 and 42 in a solvent such as dimethylacetamide, dimethylformamide using 2N sodium carbonate solution and tetrakis(triphenylphosphine)palladium(0) at ambient temperature 20-25° C. for 12-18 h. Conversion of 43 to 45 may be carried out following steps of deprotection of carbamate in presence of acid and reaction with substituted cyclopropane carbamate intermediate 6 as described in Scheme I.

Conversion of 43 to 44 may be accomplished using catalytic hydrogenation (Pd/C, H$_2$) as described in Scheme II. Similarly, conversion of 44 to 46 may be carried out following methodology involving deprotection of carbamate and reaction with substituted cyclopropane carbamate intermediate 6 as described in Scheme II.

Scheme VIII

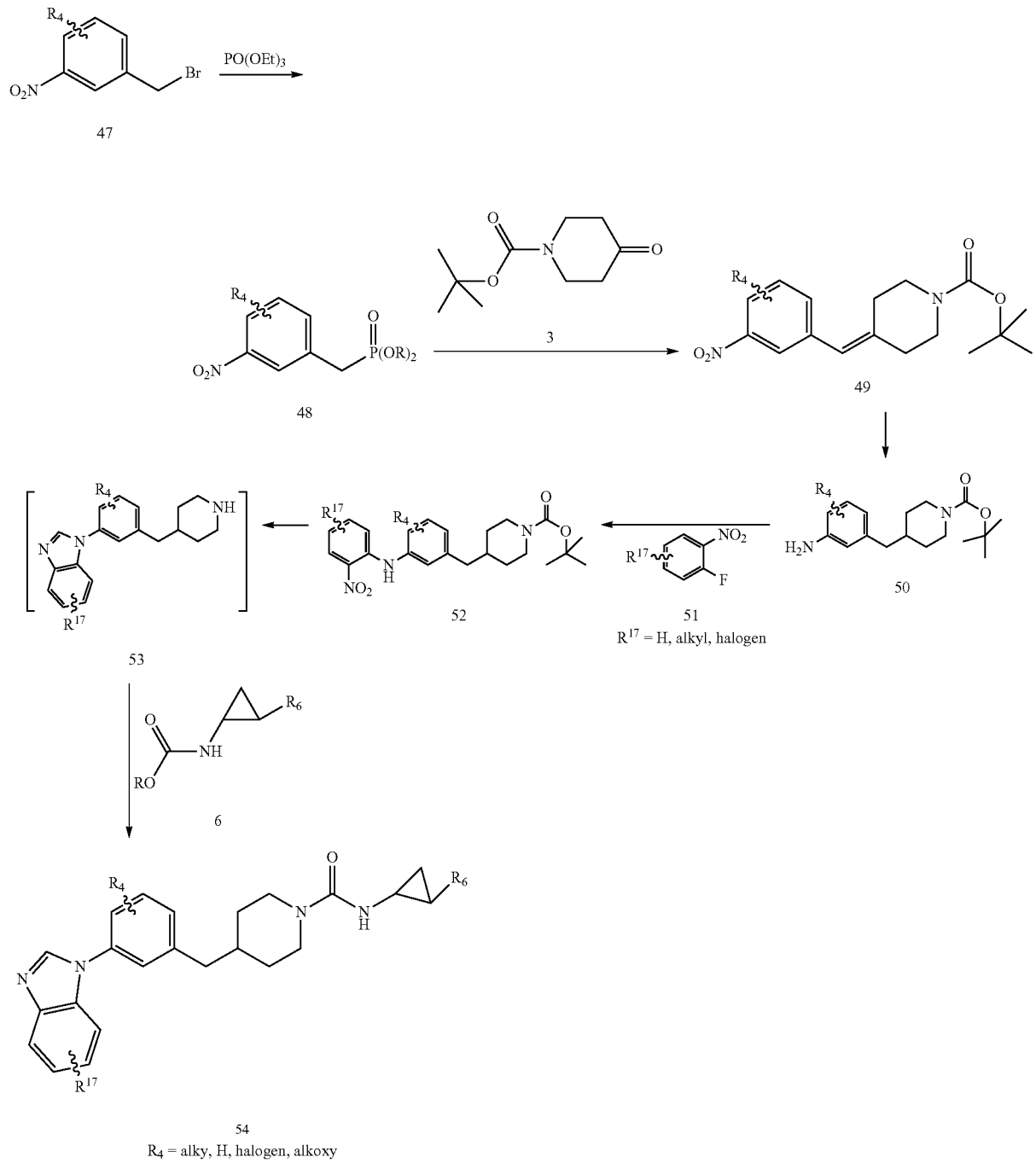

Scheme VIII shows method of synthesis of compounds of formula 54 of the present disclosure. In the first step, substituted benzyl halide 47 is reacted with trialkyl phosphate to yield substituted benzyl phosphonate 48. This reaction may be carried out by heating 47 with trialkyl phosphate at 120-150° C. for 10-20 h. The substituted alkene 49 is synthesized by generating ylid from the intermediate 48 and reacting with substituted piperidone 3. The formation of ylid from 48 may be carried using a base such as sodium hydride or potassium hydride in presence of a crown ether in a solvent such as THF, dimethoxyethane, or diethyl ether. The reaction may be initiated at low temperature (0±5° C.), followed by warming of reaction mixture to approximately 20° C. and stirring for additional 20-60 minutes. The reaction between ylid generated from 48 with 3 may be carried out in a solvent such as THF, dimethoxyethane, diethyl ether or toluene and initiating the reaction at low temperature (0±5° C.), followed by warming of reaction mixture to approximately 20-40° C. and stirring for 8-20 h. Conversion of 49 to 50 may be accomplished using catalytic hydrogenation (Pd/C, H$_2$). This reaction may be carried out using catalytic hydrogenation (using e.g.; Pd/C or Pt/C) in solvents such as methanol or ethanol in a Parr hydrogenation apparatus. In the next step, synthesis of 52 is accomplished by reacting 50 with substituted 1-fluoro-2-nitrobenzene 51 in a displacement reaction. This reaction may be carried out by treating 50 with 51 in solvent such as dimethylformamide and heating the reaction mixture in presence of cesium carbonate at 80-120° C. for 10-20 h. Synthesis of benzimidazole compound 53 may be accomplished by treating 52 with formic acid and sodium formate in presence of Pd/C at around 25° C. and heating the mixture around 100-120° C. for 12-20 h. Conversion of 53 to 54 may be carried out by treatment with substituted cyclopropane carbamate intermediate 6 as described in Scheme II.

EXAMPLES

An embodiment of the present disclosure provides for preparation of the novel compounds of Formula I using the procedures set forth in the following examples. Those skilled in the art will understand that known variations of the conditions and processes of the following preparative procedures can be used to prepare these compounds. Moreover, by utilizing the procedures described herein, one of ordinary skill in the art can prepare additional compounds of the present disclosure claimed herein.

Example 1—Synthesis of 4-(3-methoxy-benzylidene)-piperidine-1-carboxylic acid (2-phenylcyclopropyl)-amide

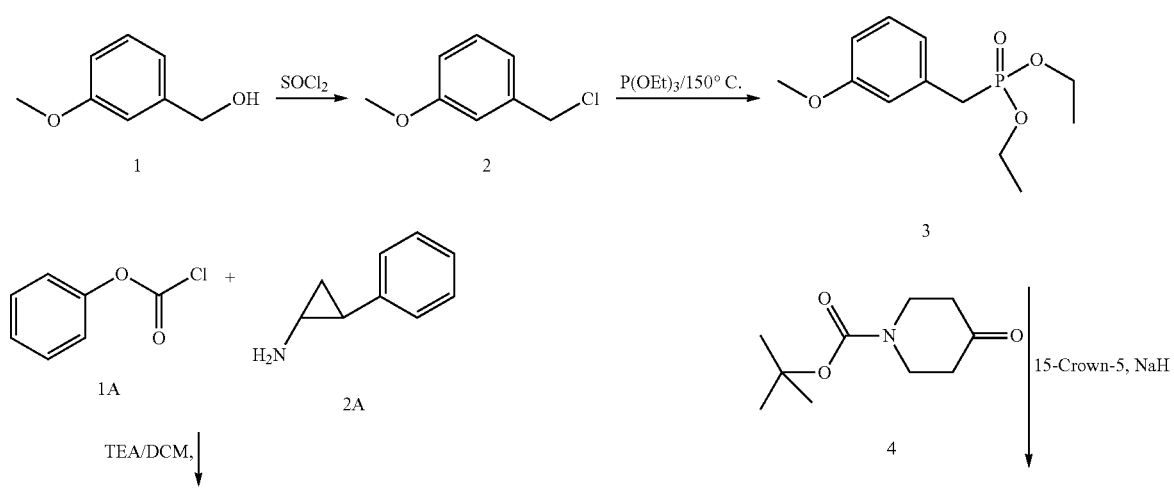

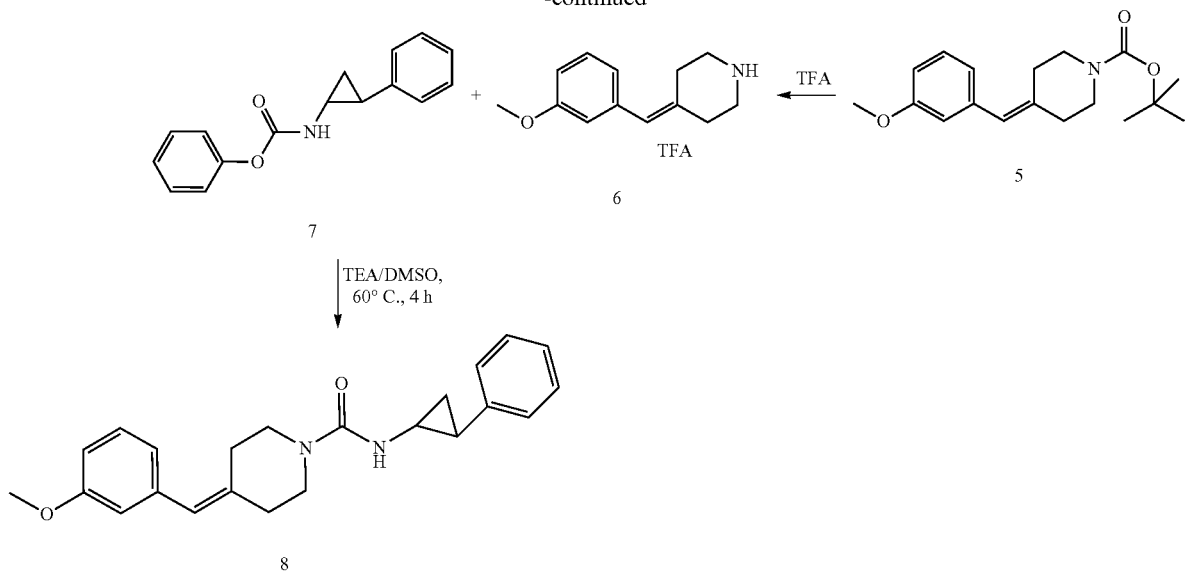

Step 1—To a mixture of (3-methoxy-phenyl)-methanol (20.0 g, 0.14 mol) and pyridine (5.8 mL, 0.72 mol) in benzene (120 mL) was added thionyl chloride (74 mL, 1.01 mol) dropwise while stirring reaction in an ice bath. After removal of ice both, the reaction mixture was allowed to stir at room temperature over a period of 2 h. The resulting reaction mixture was quenched with saturated sodium bicarbonate solution (100 mL), extracted with ethyl acetate (2×300 mL) and dried over sodium sulphate. The crude product obtained upon evaporation of the volatiles was purified through silica gel (230-400) column (5% ethyl acetate in petroleum ether) to give product 2 as a yellow oil 20.01 g (88%). $^1$H NMR (300 MHz, CDCl3) δ (ppm): 3.84 (s, 3H), 4.58 (s, 2H), 6.86-6.90 (m, 1H), 6.95-7.00 (m, 2H), 7.26-7.32 (m, 1H).

Step 2—A solution of 2 (20 g, 0.12 mol) in triethyl phosphate (29.0 mL, 0.16 mol) was heated at 150° C. over a period of 17 h. The reaction mixture was allowed to cool to room temperature and the crude product obtained upon evaporation of volatiles was purified through silica gel (230-400) column (20% ethyl acetate in petroleum ether) to give product 3 as a colorless oil 27.0 g (81%). $^1$H NMR (300 MHz, CDCl3) δ (ppm): 1.26 (t, J=7.2 Hz, 6H), 3.11 (s, 1H), 3.18 (s, 1H), 3.81 (s, 3H), 4.01-4.03 (m, 4H), 6.79-6.91 (m, 3H), 7.21-7.28 (m, 1H).

Step 3—To a solution of 3 (11.0 g, 43.0 mmol) in THF (44 mL) was added 15-crown ether (0.2 mL, 0.9 mmol). The reaction was cooled (ice bath) and NaH (580 mg, 24.2 mmol) added portion wise. The reaction mixture was allowed to stir at room temperature for 30 min and re-cooled using an ice bath. To the above reaction mixture a solution of 4-oxo-piperidine-1-carboxylic acid tert-butyl ester 4 (8.5 g, 43.0 mmol) in THF (44 mL) was added at ice temperature and allowed to stir at room temperature over a period 16 h. The resulting reaction mixture was diluted with water (100 mL), extracted with ethyl acetate and dried over sodium sulphate. The crude product obtained upon evaporation of volatiles was purified through silica gel (230-400) column (25% ethyl acetate in petroleum ether) to give product 5 as a yellow color oil 7.0 g (54%). $^1$H NMR (300 MHz, CDCl3) δ (ppm): 1.49 (s, 9H), 2.32-2.36 (m, 2H), 2.44-2.50 (m, 2H), 3.42 (t, J=5.7 Hz, 2H), 3.52 (t, J=5.7 Hz, 2H), 3.84 (s, 3H), 6.35 (s, 1H), 6.75-6.81 (m, 3H), 7.25-7.25 (m, 1H).

Step 4—To a solution of 5 (1.0 g, 3.2 mmol) in dichloromethane (8.0 mL) was added trifluoroacetic acid (4.25 mL, 4.25 vol) at ice temperature and the reaction mixture stirred at room temperature over a period of 1 h. The crude product obtained upon evaporation of volatiles was washed with diethyl ether to yield 6 as a white solid (600 mg, 89%). $^1$H NMR (300 MHz, DMSO-d6) δ (ppm): 2.54-2.62 (m, 4H), 3.07-3.17 (m, 4H), 3.75 (s, 3H), 6.44 (s, 1H), 6.77-6.84 (m, 3H), 7.27 (t, J=7.8 Hz, 1H), 8.79 (bs, 2H).

Step 5—To a suspension of trans-2-phenylcyclopropylamine 2A (3.5 g, 0.02 mol) in dichloromethane (35 mL) was added triethylamine (0.06 mol), phenyl chloroformate 1A (4.8 g, 0.03 mol) at ice bath temperature. Then ice bath was removed and reaction mixture allowed to stir at room temperature over a period of 30 min. The resulting reaction mixture was diluted with ethyl acetate (200 mL), washed with water (2×100 mL) and dried over sodium sulphate. The crude product obtained upon evaporation of volatiles was purified through silica gel (230-400) column (10% ethyl acetate in petroleum ether) to give product 7 as a white solid 2.6 g (50%). mp: 113.6-115.3° C. $^1$H NMR (300 MHz, DMSO-d6) δ (ppm): 1.14-1.26 (m, 2H), 2.03-2.09 (m, 1H), 2.72-2.75 (m, 1H), 7.10-7.40 (m, 10H), 8.18 (bs, 1H). MS: 254 (M+H).

Step 6: To a solution of amine 6 (300 mg, 0.94 mmol) in dimethyl sulfoxide (6 mL) was added diisopropylethylamine (0.5 mL, 2.82 mmol) and carbamate 7 (238 mg, 0.94 mmol) at 25° C. The reaction mixture was allowed to stir at 55° C. over a period of 4 h. The resulting reaction mixture was diluted with ethyl acetate (250 mL), washed with water (4×75 mL) and dried over sodium sulphate. The crude product obtained upon evaporation of volatiles was purified through silica gel (230-400) column (50% ethyl acetate in petroleum ether) to give product 8 as a white solid 226 mg (65%). mp: 104.7-106.4° C. $^1$H NMR (300 MHz, CDCl3) δ (ppm): 1.15-1.27 (m, 2H), 2.02-2.09 (m, 1H), 2.40 (t, J=5.7 Hz, 2H), 2.54 (t, J=5.7 Hz, 2H), 2.87 (bs, 1H), 3.39 (t, J=5.7 Hz, 2H), 3.49 (t, J=5.7 Hz, 2H), 3.82 (s, 3H), 4.87 (s, 1H, —CONH—, exchangeable $^1$H), 6.37 (s, 1H), 6.75-6.81 (m, 3H), 7.18-7.30 (m, 6H). $^{13}$C NMR (75 MHz, CDCl3) δ

(ppm): 16.44, 25.10, 29.14, 33.19, 35.72, 44.60, 45.60, 55.18, 111.88, 114.60, 121.36, 124.76, 125.95, 126.65, 128.28, 129.16, 137.90, 138.70, 140.88, 157.95, and 159.53. MS: 363 (M+H)

Example 2—Synthesis of 4-[3-(pyridin-2-yloxy)-benzylidene]-piperidine-1-carboxylic acid (2-phenyl-cyclopropyl)-amide

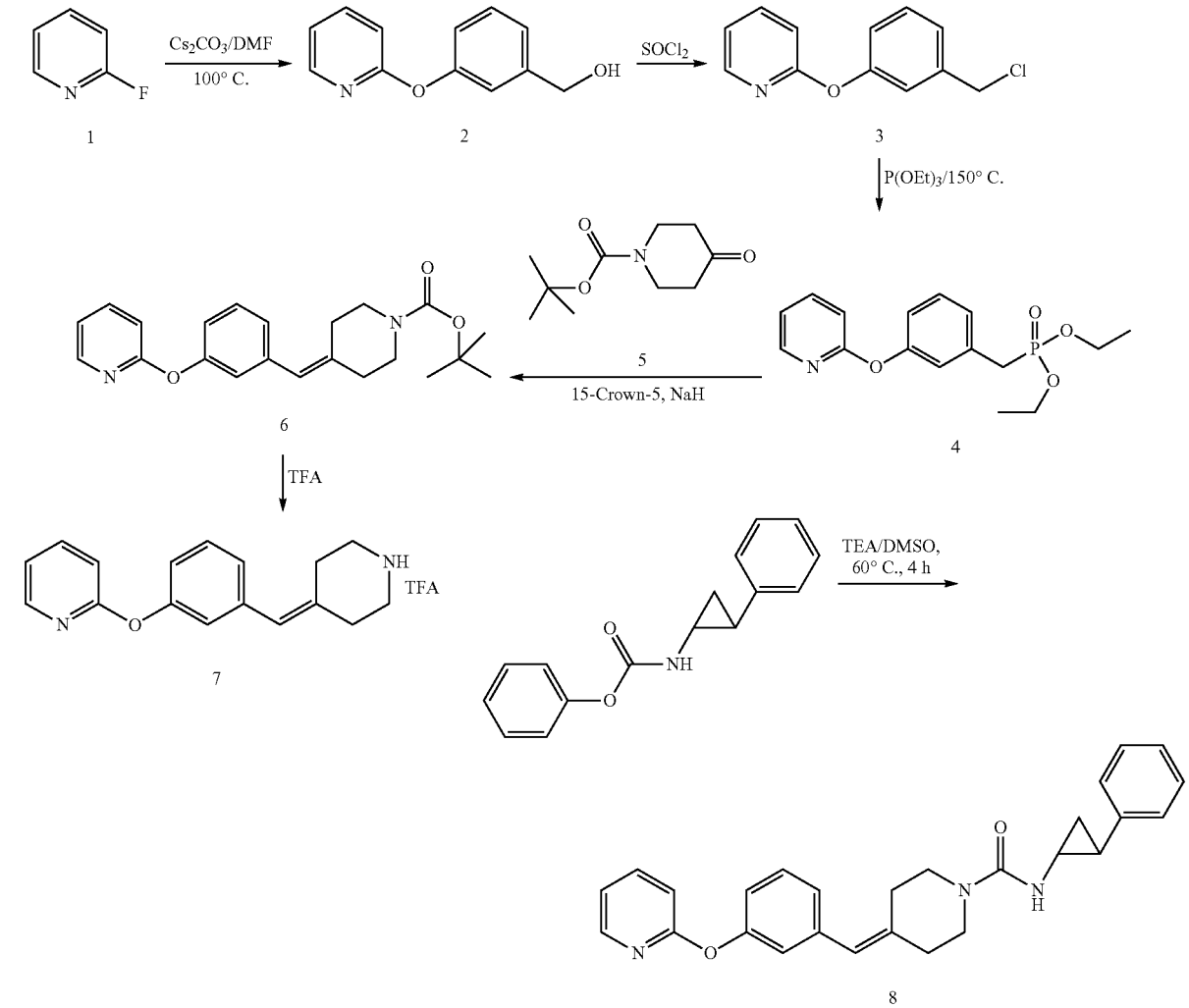

Step 1—To a solution of 2-fluoro-pyridine (25.8 g, 0.27 mol) in DMF (300 mL) was added 3-hydroxyphenyl-methanol (30.0 g, 0.24 mol) and cesium carbonate (117.3 g, 0.36 mol) at room temperature. The reaction mixture was stirred at 100° C. over a period of 5 h. Then the resulting mixture was allowed to reach room temperature, diluted with water (250 mL), extracted with ethyl acetate (3×500 mL) and the organic layer was dried over sodium sulphate. The crude product obtained upon evaporation of volatiles was purified through silica gel (230-400) column (30% ethyl acetate in petroleum ether) to give product 2 as a pale yellow oil 34.5 g (71%). $^1$H NMR (300 MHz, DMSO-d6) δ (ppm): 4.49-4.51 (m, 2H), 5.24-5.30 (m, 1H), 6.98-7.15 (m, 5H), 7.33-7.40 (m, 1H), 7.82-7.89 (m, 1H), 8.14-8.16 (m, 1H).

Step 2—To a solution of 2 (34.5 g, 0.17 mol) in dichloromethane (345 mL) was added thionyl chloride (13.9 mL, 0.18 mol) dropwise while stirring reaction in an ice bath. After removal of ice-bath, the reaction mixture was allowed to stir at room temperature over a period of 1 h. Then volatiles were evaporated under reduced pressure and diluted with toluene (25 mL) and toluene was evaporated under reduced pressure. This azeotropic process was repeated 3 times to obtain product 3 as brown color oil (36.8 g, 98%). $^1$H NMR (300 MHz, DMSO-d6) δ (ppm): 4.77 (s, 2H), 7.04-7.20 (m, 4H), 7.27-7.29 (m, 1H), 7.42 (t, J=8.4 Hz, 1H), 7.84-7.90 (m, 1H), 8.14-8.16 (m, 1H).

Step 3—A solution of 3 (36.7 g, 0.16 mol) in triethyl phosphate (41.6 mL, 0.26 mol) was heated at 150° C. over a period of 6 h. The reaction mixture was allowed to reach room temperature and the crude product obtained upon evaporation of volatiles was purified through silica gel (230-400) column (60% ethyl acetate in petroleum ether) to give product 4 as colorless oil 41.33 g. The product contained unused triethyl phosphate and was used in next step without additional purification.

Step 4—To a solution of [3-(pyridin-2-yloxy)-benzyl]-phosphonic acid diethyl ester 4 (30.0 g, 93.0 mmol) in THF (120 mL) was added 15-crown ether (0.41 g, 1.8 mmol). The reaction was cooled (ice bath) and NaH (3.35 g, 0.14 mol) was added portion wise. The reaction mixture was allowed to stir at room temperature for 30 min and again cooled to ice temperature. To the above reaction mixture, a solution of 4-oxo-piperidine-1-carboxylic acid tert-butyl ester 5 (18.6 g, 93.0 mmol) in THF (120 mL) was added at ice temperature and allowed to stir at room temperature over a period of 16 h. The resulting reaction mixture was diluted with water (500 mL), extracted with ethyl acetate (3×500 mL) and dried over sodium sulphate. The crude product obtained upon evaporation of volatiles was purified through silica gel (230-400) column (3% ethyl acetate in petroleum ether) to give product 6 as a yellow color oil 24.3 g (71%). $^1$H NMR (300 MHz, CDCl3) δ (ppm): 1.41 (s, 9H), 2.27 (t, J=5.4 Hz, 2H), 2.40 (t, J=5.4 Hz, 2H), 3.33 (bs, 2H), 3.40 (t, J=5.4 Hz, 2H), 6.37 (s, 1H), 6.95-7.15 (m, 4H), 7.37 (t, J=7.8 Hz, 2H), 7.83-7.88 (m, 1H), 8.14-8.16 (m, 1H).

Step 5—To a solution of 4-[3-(pyridin-2-yloxy)-benzylidene]-piperidine-1-carboxylic acid tert-butyl ester 6 (12.0 g, 33.0 mmol) in dichloromethane (120.0 mL) was added trifluoroacetic acid (51 mL) at ice temperature and the reaction mixture was stirred at room temperature over a period of 1 h. The brown color oil 7 (13.7 g, 85%) obtained upon evaporation of volatiles was used to next step (13.7 g, 85%) without additional purification. $^1$H NMR (300 MHz, DMSO-d6) δ (ppm): 2.56-2.63 (m, 4H), 3.10-3.16 (m, 4H), 6.46 (s, 1H), 6.99-7.15 (m, 5H), 7.39 (t, J=7.5 Hz, 1H), 7.83-7.88 (m, 1H), 8.14-8.16 (m, 1H).

Step 6—To a solution of amine 7 (15.0 g, 26.0 mmol) in dimethyl sulfoxide (150 mL) was added diisopropylethylamine (13.6 mL, 78.0 mmol) and product of Step 5, Example 1 (6.7 g, 26.0 mmol) at 25° C. The reaction mixture was allowed to stir at 60° C. over a period of 5 h. The resulting reaction mixture was diluted with ethyl acetate (1.2 L), washed with water (3×150 mL) and dried over sodium sulphate. The crude product obtained upon evaporation of volatiles was purified through silica gel (230-400) column (50% ethyl acetate in petroleum ether) to give product 8 as a pale yellow solid 9.1 g (81%). mp: 52.3-54.1° C. $^1$H NMR (300 MHz, DMSO-d6) δ (ppm): 1.06-1.18 (m, 2H), 1.88 (bs, 1H), 2.26 (m, 2H), 2.28 (m, 2H), 2.69-2.72 (m, 1H), 3.29-3.38 (m, 4H), 6.36 (s, 1H), 6.85-6.86 (bs, 1H, —CONH—, Exchangeable $^1$H), 6.95-7.40 (m, 10H), 7.86 (t, J=6.3 Hz, 1H), 8.14-8.16 (m, 2H). $^{13}$C NMR (75 MHz, DMSO-d6) δ (ppm): 15.99, 27.74, 29.40, 34.42, 36.08, 44.41, 45.47, 112.09, 119.31, 119.52, 121.60, 123.58, 125.24, 125.80, 126.41, 128.52, 129.88, 139.19, 140.09, 140.56, 142.42, 147.91, 154.42, 158.09 and 163.45. MS: 426 (M+H)

Example 3—Synthesis of 4-[3-(5-trifluoromethyl-pyridin-2-yloxy)-benzylidene]-piperidine-1-carboxylic acid (2-phenyl-cyclopropyl)-amide

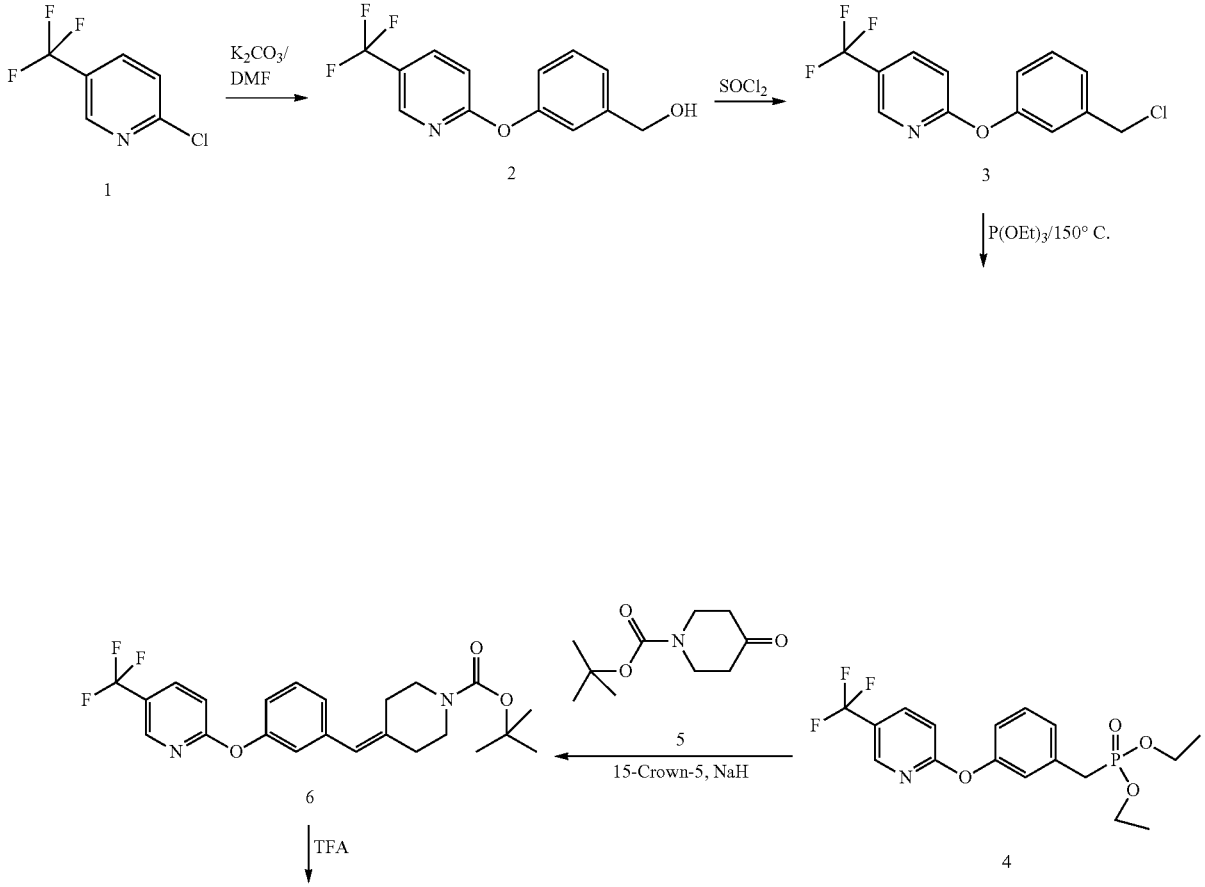

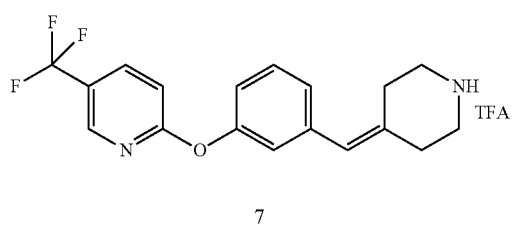

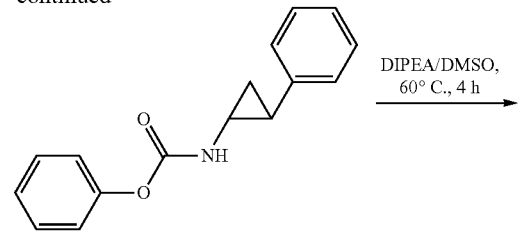

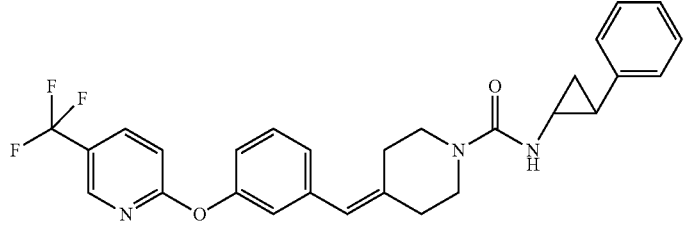

Step 1—To a solution of 5-trifluoromethyl-2-chloro-pyridine (23.0 g, 0.12 mol) in DMF (230 mL) was added 3-hydroxyphenyl-methanol (17.4 g, 0.13 mol) and potassium carbonate (26.3 g, 0.19 mol) at room temperature. The reaction mixture was stirred at 100° C. over a period of 5 h. Then the resulting mixture was allowed to reach room temperature, diluted with water (200 mL), extracted with ethyl acetate (3×400 mL) and the organic layer was dried over sodium sulphate. The crude product obtained upon evaporation of volatiles was purified through silica gel (230-400) column (12% ethyl acetate in petroleum ether) to give product 2 as a pale yellow oil 28.1 g (82%). $^1$H NMR (300 MHz, CDCl$_3$) δ (ppm): 4.75 (s, 2H), 7.03-7.10 (m, 2H), 7.19 (s, 1H), 7.26-7.28 (m, 1H), 7.44 (t, J=7.8 Hz, 1H), 7.90-7.94 (m, 1H), 8.45 (s, 1H).

Step 2—To a solution of 2 (28.0 g, 0.10 mol) in dichloromethane (280 mL) was added thionyl chloride (8.5 mL, 0.11 mol) drop wise while stirring reaction in an ice bath. After removal of ice-bath, the reaction mixture was allowed to stir at room temperature over a period of 1 h. Then volatiles were evaporated under reduced pressure, diluted with toluene (15 mL) and toluene was evaporated under reduced pressure. This azeotropic process was repeated 3 times to obtain product 3 as red color oil (29.6 g, 99%). $^1$H NMR (300 MHz, CDCl$_3$) δ (ppm): 4.62 (s, 2H), 7.05 (d, J=8.7 Hz, 1H), 7.12-7.13 (m, 1H), 7.23-7.32 (m, 2H), 7.42-7.47 (m, 1H), 7.92-7.95 (m, 1H), 8.46 (s, 1H).

Step 3—A solution of 3 (29.0 g, 0.10 mol) in triethyl phosphate (26.2 mL, 0.15 mol) was heated at 150° C. over a period of 6 h. The reaction mixture was allowed to reach room temperature and the mixture was added to n-heptane (150 mL) to obtain light orange color precipitate. The precipitate obtained was filtered and dried under vacuum to give product 4 as white solid (30.8 g, 94%) and it was used in next step without further purification. $^1$H NMR (300 MHz, DMSO-d6) δ (ppm): 1.16 (t, J=6.9 Hz, 6H), 3.24 and 3.31 (2s, 2H), 3.90-4.00 (m, 4H), 7.07-7.10 (m, 2H), 7.17-7.25 (m, 2H), 7.39 (d, J=8.7 Hz, 1H), 8.23-8.26 (m, 1H), 8.55 (s, 1H).

Step 4—To a solution of ester 4 (25.0 g, 64.0 mmol) in THF (100 mL) was added 15-crown ether (0.28 g, 1.3 mmol). The reaction was cooled (ice bath) and NaH (2.3 g, 96.0 mmol) was added portion wise over a period of 5 min. The reaction mixture was allowed to stir at room temperature for 30 min and again cooled to ice temperature. To the above reaction mixture, a solution of 4-oxo-piperidine-1-carboxylic acid tert-butyl ester 5 (12.81 g, 64.0 mmol) in THF (100 mL) was added at ice temperature and allowed to stir at room temperature over a period 16 h. The resulting reaction mixture was diluted with water to obtain white precipitate. The precipitate was filtered and dried to give product 6 as a white solid (24.4 g, 87%). $^1$H NMR (300 MHz, CD$_3$OD) δ (ppm): 1.48 (s, 9H), 2.36 (t, J=5.1 Hz, 2H), 2.49 (t, J=5.4 Hz, 2H), 3.43 (t, J=5.7 Hz, 2H), 3.52 (t, J=5.7 Hz, 2H), 6.43 (s, 1H), 7.01-7.03 (m, 2H), 7.14 (d, J=8.4 Hz, 2H), 7.38-7.44 (m, 1H), 8.09-8.12 (m, 1H), 8.44 (bs, 1H).

Step 5—To a solution of 6 (10.0 g, 23.0 mmol) in dichloromethane (100 mL) was added trifluoroacetic acid (42.5 mL) at ice temperature and the reaction mixture was stirred at room temperature over a period of 1 h. Then volatiles were removed under reduced pressure to obtain product as red color oil (10.7 g, 83%). The crude product 7 was used for next step without further purification. $^1$H NMR (300 MHz, DMSO-d6) δ (ppm): 2.60-2.64 (m, 4H), 3.11-3.17 (m, 4H), 6.47 (s, 1H), 7.08-7.26 (m, 4H), 7.43 (t, J=8.1 Hz, 1H), 8.21-8.23 (m, 1H), 8.56 (s, 1H), 8.76 (bs, 1H).

Step 6—To a solution of amine 7 (10.5 g, 18.7 mmol) in dimethyl sulfoxide (10 mL) was added diisopropylethylamine (9.8 mL, 56.1 mmol) and product of Step 5, Example 1 (4.74 g, 18.7 mmol) at 25° C. The reaction mixture was allowed to stir at 60° C. over a period of 5 h. The resulting reaction mixture was diluted with ethyl acetate (1.0 L), washed with water (3×150 mL) and dried over sodium sulphate. The crude product obtained upon evaporation of volatiles was purified through silica gel (230-400) column (40% ethyl acetate in petroleum ether) to give product 8 as a white solid 7.0 g (76%). mp: 98.9-101.5° C. $^1$H NMR (300 MHz, DMSO-d6) δ (ppm): 1.08-1.18 (m, 2H), 1.85-1.90 (m, 1H), 2.77 (bs, 2H), 2.39 (bs, 2H), 2.69-2.72 (m, 1H), 3.32-3.39 (m, 4H), 6.37 (s, 1H), 6.85 (s, 1H, D$_2$O exchangeable $^1$H), 7.04-7.24 (m, 9H), 7.41 (t, J=7.8 Hz, 1H), 8.22-8.25 (m, 1H), 8.58 (s, 1H). $^{13}$C NMR (75 MHz, DMSO-d6) δ (ppm): 15.99, 24.74, 29.39, 34.44, 36.07, 44.37, 45.44, 112.25, 118.97, 119.81, 120.23, 120.66, 121.09, 121.53, 122.08, 122.57, 123.42, 125.79, 126.15, 126.38, 128.52, 129.76, 130.08, 137.98, 138.01, 139.42, 140.34, 142.42, 145.72, 145.77, 153.38, 158.08, 166.01. MS: 494 (M+H).

Example 4—Synthesis of 4-[3-(pyridin-2-yloxy)-benzyl]-piperidine-1-carboxylic acid (2-phenyl-cyclopropyl)-amide

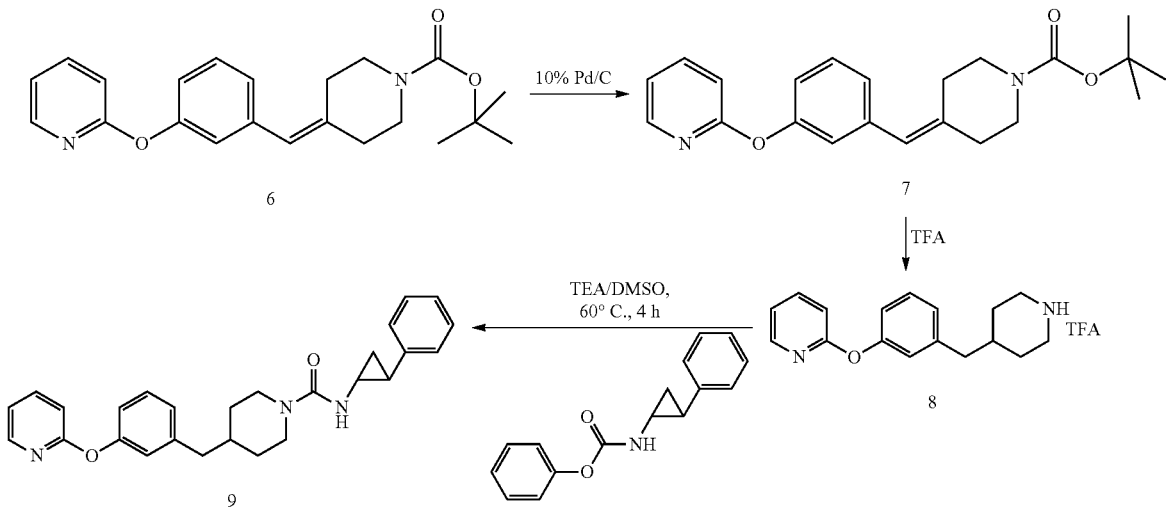

Step 1—To a solution of product of Step 4, Example 2 (6) in methanol (17 mL) was added 10% Pd/C (900 mg) at room temperature and the reaction mixture was stirred under hydrogen balloon pressure over a period of 1 h. The resulting reaction mixture was filtered through celite bed and the filtrate was concentrated under reduced pressure to give product 7 as a yellow oil (850 mg, 66%). $^1$H NMR (300 MHz, DMSO-d6) δ (ppm): 0.98-1.04 (m, 2H), 1.37 (s, 9H), 1.43-1.56 (m, 3H), 2.60 (m, 4H), 3.88-3.92 (m, 2H), 6.91-7.02 (m, 2H), 7.10-7.17 (m, 2H), 7.25-7.31 (m, 2H), 7.84-7.89 (m, 1H), 8.14-8.16 (m, 1H).

Step 2—To a solution of ester 7 (800 mg, 2.17 mmol) in dichloromethane (8 mL) was added trifluoroacetic acid (3.4 mL, 4.25 vol) at ice temperature and the reaction mixture was stirred at room temperature over a period of 1 h. Then volatiles were removed under reduced pressure to obtain product as brown color oil (800 mg, 74%). The crude product 8 was used in next step without further purification.

Step 3—To a solution of crude amine 8 (500 mg, 1.0 mmol) in dimethyl sulfoxide (10 mL) was added diisopropylethylamine (0.5 mL, 2.82 mmol) and product of Step 5, Example 1 (256 mg, 1.0 mmol) at 25° C. The reaction mixture was allowed to stir at 60° C. over a period of 5 h. The resulting reaction mixture was diluted with ethyl acetate (250 mL), washed with water (4×75 mL) and dried over sodium sulphate. The crude product obtained upon evaporation of volatiles was purified through silica gel (230-400) column (60% ethyl acetate in petroleum ether) to give product 9 as a white solid 230 mg (53%). mp: 126.8-128.6° C. $^1$H NMR (300 MHz, CDCl3) δ (ppm): 1.12-1.27 (m, 4H), 1.68-1.71 (m, 3H), 1.89-2.06 (m, 1H), 2.56 (d, J=6.6 Hz, 2H), 2.73 (t, J=11.4 Hz, 2H), 2.82-2.86 (m, 1H), 3.92 (d, J=13.5 Hz, 2H), 4.84 (s, 1H, —CONH—, Exchangeable $^1$H), 6.90-7.03 (m, 5H), 7.15-7.35 (m, 6H), 7.68-7.74 (m, 1H), 8.21-8.23 (m, 2H). $^{13}$C NMR (75 MHz, CDCl3) δ (ppm): 16.45, 25.06, 29.65, 31.82, 33.18, 37.88, 42.86, 44.24, 111.61, 118.48, 118.61, 121.66, 125.36, 125.88, 126.66, 128.24, 129.40, 139.37, 141.02, 141.99, 147.80, 154.28, 158.21 and 163.73. MS: 428 (M+H)

Example 5—Chiral Separation of Racemic Product of Example 2

The chiral column (CHIRALPACK IA 250 mm×10 mm 5 m) was equilibrated using mobile phase (n-hexane: isopropyl alcohol; 80:20 v/v) for 15 column volumes prior to the compound elution. Then 500 μL of the stock solution, prepared by dissolving 500 mg of the product of Example 2 in 5 mL of n-hexane and isopropyl alcohol (8:2), was injected and fractions collected based on the separation seen in the chromatogram. The fraction F1 was the first eluted fraction (retention time:11.5 min to 13.00 min) and F2 the second eluted fraction (retention time:13.50 min to 15.50 min) from chiral column. The injections were repeated to complete separation of the remaining (4.5 mL) stock solution. Then solvents of F-1 and F-2 were removed separately under reduced pressure to yield the chiral products 5A (entA) (140 mg) and 5B (entB) (150 mg), respectively.

5A 4-[3-(pyridin-2-yloxy)-benzylidene]-piperidine-1-carboxylic acid {(1S,2R)-2-phenyl-cyclopropyl)}-amide— HPLC: 99.98% (Chiral purity: 98.55%). mp: 45.0-47.1° C. $^1$H NMR (300 MHz, DMSO-d6) δ (ppm): 1.06-1.10 (m, 1H), 1.15-1.18 (m, 1H), 1.87 (m, 1H), 2.24-2.28 (m, 2H), 2.38-2.40 (m, 2H), 2.69-2.72 (m, 1H), 3.29-3.40 (m, 4H), 6.36 (s, 1H), 6.85-6.86 (m, 1H), 6.95-7.27 (m, 10H), 7.37 (t, J=7.8 Hz, 1H), 7.83-7.85 (m, 1H), 8.14-8.16 (m, 1H). MS: 426 (M+H).

5B 4-[3-(pyridin-2-yloxy)-benzylidene]-piperidine-1-carboxylic acid {(1R,2S)-2-phenyl-cyclopropyl)}-amide— HPLC: 99.89% (Chiral purity: 98.93%). mp: 51.0-54.3° C. $^1$H NMR (300 MHz, DMSO-d6) δ (ppm): 1.06-1.08 (m, 1H), 1.15-1.18 (m, 1H), 1.87 (m, 1H), 2.24-2.26 (m, 2H), 2.38-2.40 (m, 2H), 2.69-2.72 (m, 1H), 3.29-3.40 (m, 4H), 6.36 (s, 1H), 6.84-6.85 (m, 1H), 6.95-7.27 (m, 10H), 7.37 (t, J=7.8 Hz, 1H), 7.83-7.85 (m, 1H), 8.14-8.16 (m, 1H MS: 426 (M+H).

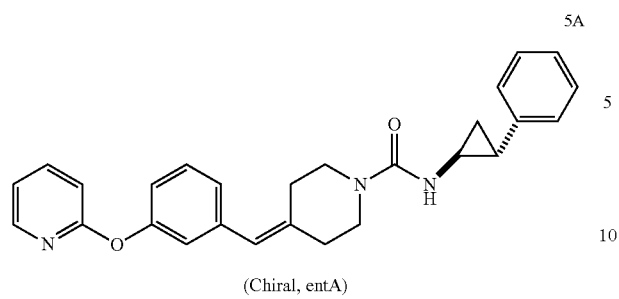
(Chiral, entA)
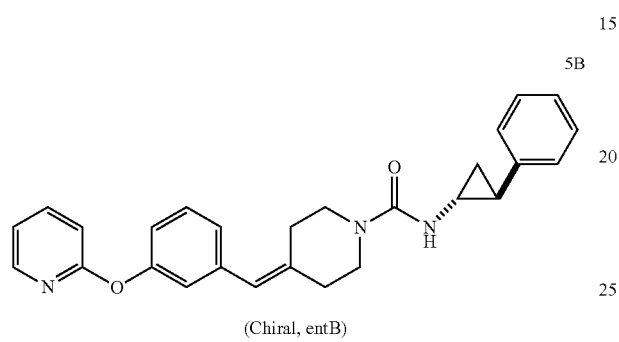
(Chiral, entB)
Example 6—Synthesis of 4-[3-(pyrimidin-2-yloxy)-benzylidene]-piperidine-1-carboxylic acid (2-phenyl-cyclopropyl)-amide
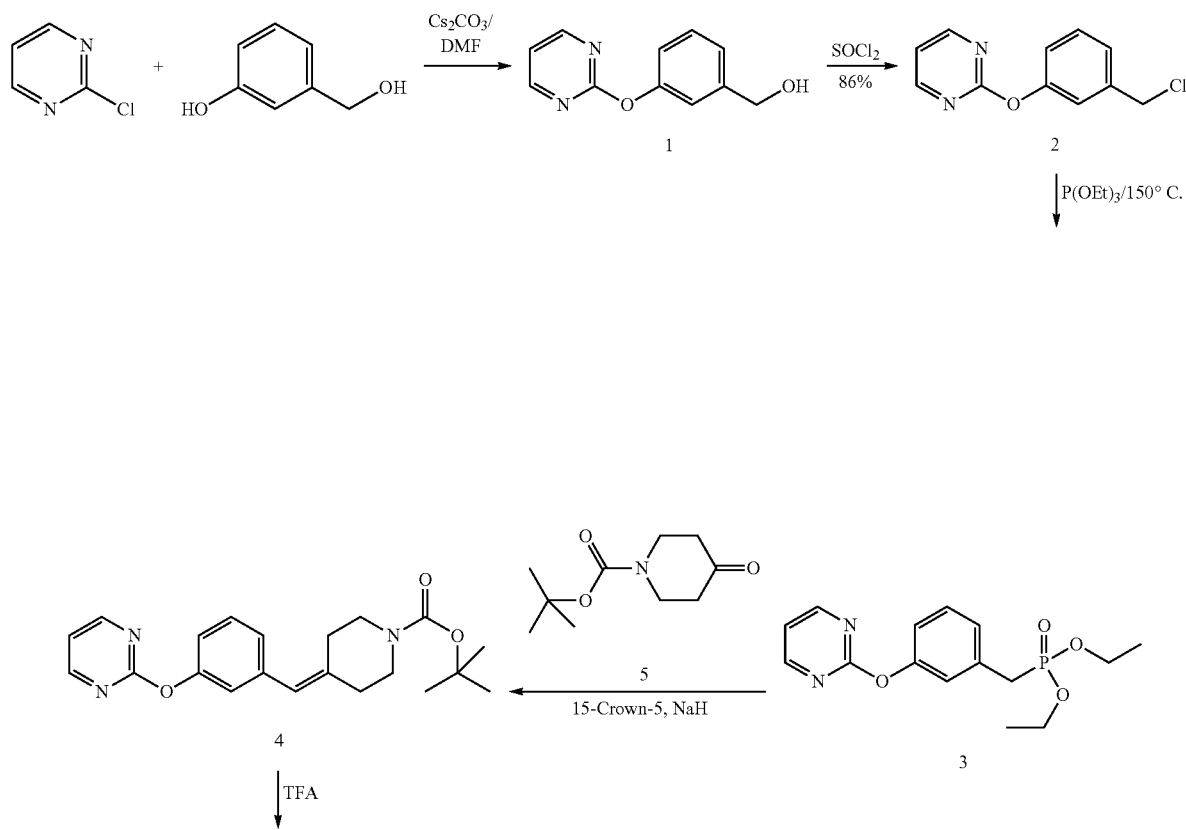

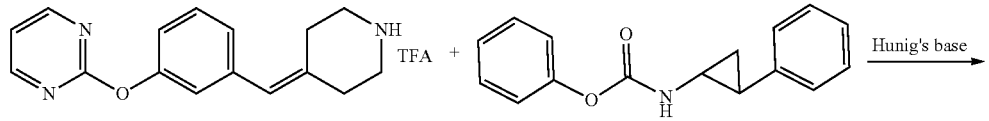

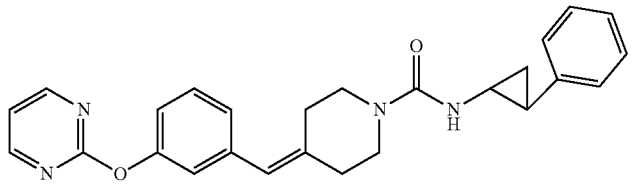

Step 1—To a solution of 3-hydroxyphenyl-methanol (500 mg, 4.0 mmol) in DMF (5 mL) was added cesium carbonate (2.6 g, 8.0 mmol) and 2-chloropyrimidine (680 mg, 6.0 mmol) at room temperature. The reaction mixture was stirred at 100° C. over a period of 5 h. Then the resulting reaction mixture was allowed to cool to room temperature, filtered to remove cesium carbonate, the filtrate was diluted with water (50 mL), extracted with ethyl acetate (100 mL) and the organic layer was dried over sodium sulphate. The crude product obtained upon evaporation of volatiles was purified through silica gel (230-400) column (50% ethyl acetate in petroleum ether) to give product 1 as a pale yellow oil 440 mg (54%). $^1$H NMR (300 MHz, DMSO-d6) δ (ppm): 4.52 (s, 2H), 5.28 (bs, 1H), 7.03-7.99 (m, 5H), 8.63 (d, J=1.2 Hz, 2H).

Step 2—To a solution of 1 (440 mg, 2.1 mmol) in dichloromethane (8 mL) was added thionyl chloride (0.19 mL, 2.6 mmol) dropwise while stirring reaction in an ice bath. After removal of ice-bath, the reaction mixture was allowed to stir at room temperature over a period of 1 h. The resulting reaction mixture was quenched with ice cold water (10 mL) and extracted with ethyl acetate (100 mL) and dried over sodium sulphate. The crude product obtained upon evaporation of volatiles was purified through silica gel (230-400) column (25% ethyl acetate in petroleum ether) to give product 2 as a pale pink solid 400 mg (83%). $^1$H NMR (300 MHz, DMSO-d6) δ (ppm): 4.78 (s, 2H), 7.17-7.19 (m, 1H), 7.28-7.34 (m, 3H), 7.42-7.45 (m, 1H), 8.65 (d, J=4.5 Hz, 2H).

Step 3—A solution of 2-(3-chloromethyl-phenoxy)-pyrimidine 2 (400 mg, 1.8 mmol) in triethyl phosphate (0.45 mL, 2.7 mmol) was heated at 150° C. over a period of 6 h. The reaction mixture was allowed to reach room temperature and the crude product obtained upon evaporation of volatiles was purified through silica gel (230-400) column (50% ethyl acetate in petroleum ether) to give product 3 as white solid 400 mg (69%). $^1$H NMR (300 MHz, DMSO-d6) δ (ppm): 1.16 (t, J=6.9 Hz, 6H), 3.23 (s, 1H), 3.30 (s, 1H), 3.90-4.00 (m, 4H), 7.06-7.09 (m, 2H), 7.16-7.18 (m, 1H), 7.25-7.28 (m, 1H), 7.37 (t, J=7.5 Hz, 1H), 8.64 (d, J=4.8 Hz, 2H).

Step 4—To a solution of ester 3 (400 mg, 1.2 mmol) in THF (2.5 mL) was added 15-crown ether (5 μL, 0.02 mmol). The reaction was cooled (ice bath) and NaH (44 mg, 1.8 mmol) added portion wise. The reaction mixture was allowed to stir at room temperature for 30 min and again cooled to ice temperature. To the above reaction mixture, a solution of 4-oxo-piperidine-1-carboxylic acid tert-butyl ester (250 mg, 1.2 mmol) in THF (2.5 mL) was added at ice temperature and allowed to stir at room temperature over a period 16 h. The resulting reaction mixture was diluted with water (10 mL), extracted with ethyl acetate (100 mL) and dried over sodium sulphate. The crude product obtained upon evaporation of volatiles was purified through silica gel (230-400) column (25% ethyl acetate in petroleum ether) to give product 4 as a white solid 360 mg (80%). $^1$H NMR (300 MHz, DMSO-d6) δ (ppm): 1.41 (s, 9H), 2.28 (t, J=5.4 Hz, 2H), 2.41 (t, J=5.7 Hz, 2H), 3.33-3.41 (m, 4H), 6.38 (s, 1H), 7.03-7.13 (m, 3H), 7.26 (t, J=4.8 Hz, 1H), 7.39 (t, J=7.8 Hz, 1H), 8.65 (d, J=4.8 Hz, 2H).

Step 5—To a solution of 4 (360 mg, 0.97 mmol) in dichloromethane (4.0 mL) was added trifluoroacetic acid (1.7 mL) at ice temperature and the reaction mixture was stirred at room temperature over a period of 1 h. The crude product obtained upon evaporation of the solvent was washed with diethyl ether to yield product 5 as an off-white solid 0.31 g (83%) and was taken to next without additional purification.

Step 6—To a solution of amine 5 (310 mg, 0.6 mmol) in dimethyl sulfoxide (4.0 mL) was added diisopropylethylamine (0.5 mL, 3.1 mmol) and product of Step 5, Example 1 (0.58 g, 2.4 mmol) at 25° C. The reaction mixture was allowed to stir at 60° C. over a period of 5 h. The resulting reaction mixture was diluted with ethyl acetate (100 mL), washed with water (3×50 mL) and dried over sodium sulphate. The crude product obtained upon evaporation of volatiles was purified through silica gel (230-400) column (60% ethyl acetate in petroleum ether) to give product 6 as a white solid 210 mg (77%). mp: 52.7-57.6° C. $^1$H NMR (300 MHz, DMSO-d6) δ (ppm): 1.04-1.06 (m, 1H), 1.14-1.20 (m, 1H), 1.85-1.88 (m, 1H), 2.27 (bs, 2H), 2.39 (bs, 2H), 2.70-2.71 (m, 1H), 3.32-3.39 (m, 4H), 6.37 (s, 1H), 6.85 (bs, 1H, CONH exchangeable $^1$H), 7.03-7.15 (m, 6H), 7.22-7.28 (m, 3H), 7.39 (t, J=7.8 Hz, 1H), 8.65 (d, J=7.8 Hz, 2H). $^{13}$C NMR (75 MHz, DMSO-d6) δ (ppm): 16.03, 24.76, 29.37, 34.50, 36.10, 44.37, 45.41, 117.37, 119.95, 122.23, 123.49, 125.80, 126.00, 126.34, 128.54, 129.91, 139.19, 140.21, 142.44, 153.20, 158.05, 160.47 and 165.21. MS: 427 (M+H).

Example 7—Synthesis of 4-{3-[1-(2-phenyl-cyclopropylcarbamoyl)-piperidin-4-ylidenemethyl]-phenoxy}-benzoic acid methyl ester

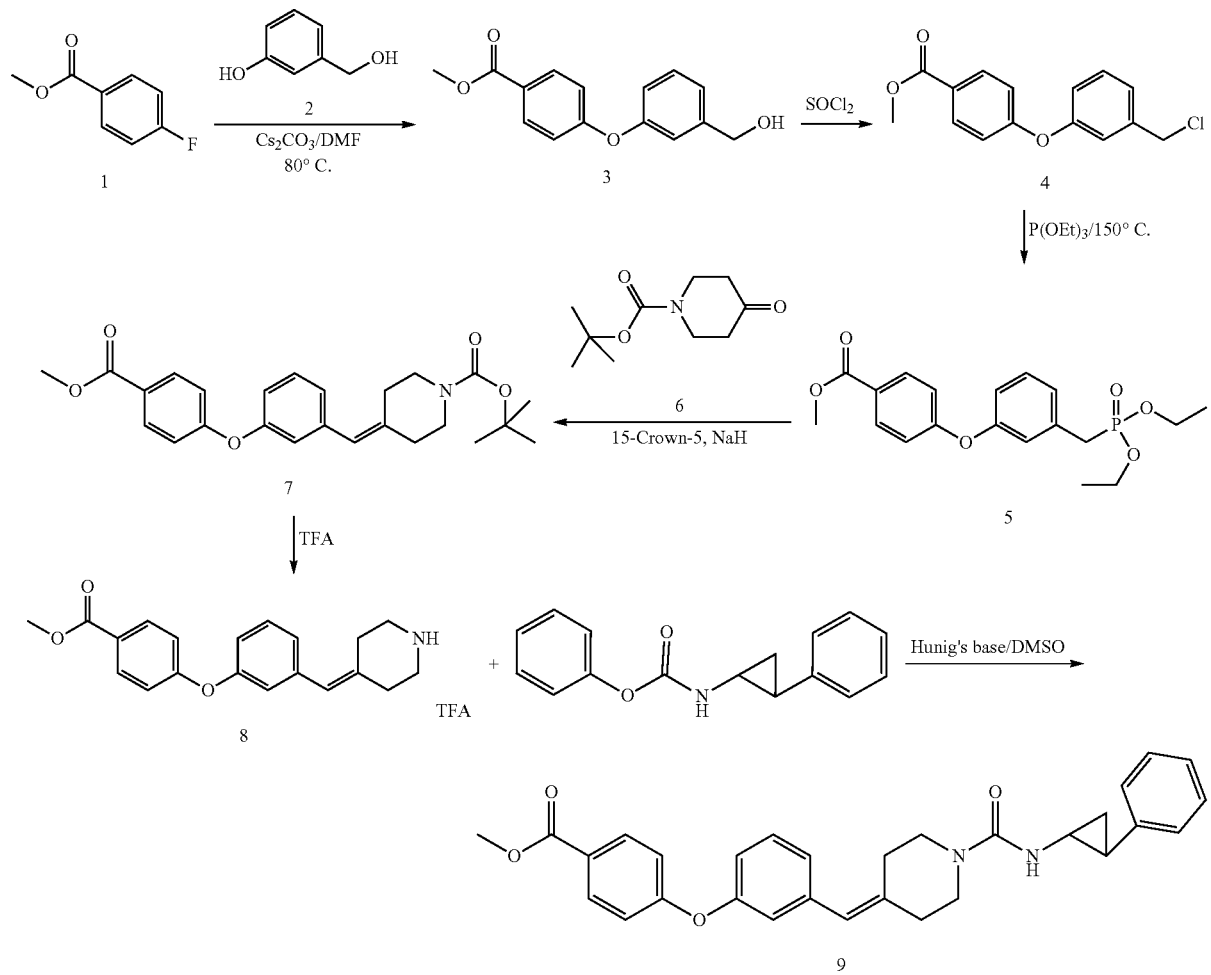

Step 1—To a solution of 3-hydroxyphenyl-methanol 2 (5.0 g, 40.2 mmol) in DMF (50 mL) was added cesium carbonate (26.2 g, 80.5 mmol) and ester 1 (7.5 g, 48.3 mmol) at room temperature. The reaction mixture was stirred at 100° C. over a period of 5 h. Then the resulting reaction mixture was allowed to reach room temperature and filtered to remove cesium carbonate. The filtrate was diluted with water (200 mL), extracted with ethyl acetate (2×250 mL) and the organic layer dried over sodium sulphate. The crude product obtained upon evaporation of volatiles was purified through silica gel (230-400) column (30% ethyl acetate in petroleum ether) to give product 3 as a pale yellow oil 3.2 g (31%). $^1$H NMR (300 MHz, DMSO-d6) δ (ppm): 3.81 (s, 3H), 4.51 (d, J=5.7 Hz, 2H), 5.28 (t, J=5.7 Hz, 1H), 6.98-7.06 (m, 4H), 7.17-7.19 (m, 1H), 7.38-7.40 (m, 1H), 7.95-7.98 (m, 2H).

Step 2—To a solution of alcohol 3 (3.2 g, 12.3 mmol) in dichloromethane (50 mL) was added thionyl chloride (1.7 mL, 14.8 mmol) dropwise while stirring reaction in an ice bath. After removal of ice-bath, the reaction mixture was allowed to stir at room temperature over a period of 1 h. The resulting reaction mixture was quenched with ice cold water (50 mL) and extracted with ethyl acetate (250 mL) and dried over sodium sulphate. The crude product obtained upon evaporation of volatiles was purified through silica gel (230-400) column (5% ethyl acetate in petroleum ether) to give product 4 as colorless oil 2.3 g (67%). $^1$H NMR (300 MHz, DMSO-d6) δ (ppm): 3.83 (s, 3H), 4.78 (s, 2H), 7.06-7.12 (m, 3H), 7.21 (bs, 1H), 7.30-7.33 (m, 1H), 7.44-7.49 (m, 1H), 7.98 (d, J=8.7 Hz, 2H).

Step 3—A solution of compound 4 (2.3 g, 7.9 mmol) in triethyl phosphate (2.3 mL, 11.9 mmol) was heated at 150° C. over a period of 6 h. The reaction mixture was allowed to reach room temperature and the crude product obtained upon evaporation of volatiles was purified through silica gel (230-400) column (50% ethyl acetate in petroleum ether) to give product 5 as pale yellow oil 3.5 g (91%). $^1$H NMR (300 MHz, DMSO-d6) δ (ppm): 1.15 (t, J=6.9 Hz, 6H), 3.23 (s, 1H), 3.30 (s, 1H), 3.83 (s, 3H), 3.89-3.99 (m, 4H), 7.00-7.06 (m, 4H), 7.15-7.17 (m, 1H), 7.39 (t, J=7.8 Hz, 1H), 7.97 (d, J=8.7 Hz, 2H).

Step 4—To a solution of 5 (3.5 g, 9.2 mmol) in THF (20 mL) was added 15-crown ether (40 μL, 0.18 mmol). The reaction was cooled (ice bath) and NaH (560 mg, 13.8 mmol) was added portion wise. The reaction mixture was allowed to stir at room temperature for 30 min and again cooled to ice temperature. To the above reaction mixture, a solution of 4-oxo-piperidine-1-carboxylic acid tert-butyl ester 6 (1.9 g, 9.2 mmol) in THF (15 mL) was added at ice temperature and allowed to stir at room temperature over a period 16 h. The resulting reaction mixture was quenched with saturated ammonium chloride (50 mL), extracted with ethyl acetate (500 mL) and dried over sodium sulphate. The crude product obtained upon evaporation of volatiles was purified through silica gel (230-400) column (10% ethyl acetate in petroleum ether) to give product 7 as a white solid 1.8 g (46%). $^1$H NMR (300 MHz, DMSO-d6) δ (ppm): 1.40 (s, 9H), 2.27-2.40 (m, 4H), 3.40-3.60 (m, 4H), 3.83 (s, 3H), 6.37 (s, 1H), 6.94-6.99 (m, 2H), 7.05-7.12 (m, 3H), 7.39-7.41 (m, 1H), 7.98 (d, J=8.7 Hz, 2H).

Step 5—To a solution of tert-butyl ester 7 (1.8 g, 4.2 mmol) in dichloromethane (18.0 mL) was added trifluoroacetic acid (9.0 mL) at ice temperature and the reaction mixture was stirred at room temperature over a period of 1 h. The crude product obtained upon evaporation of the solvent was washed with n-hexane to obtain product 8 as thick black liquid 1.5 g (83%). $^1$H NMR (300 MHz, DMSO-d6) δ (ppm): 2.63-2.72 (m, 4H), 3.16-3.28 (m, 4H), 3.91 (s, 3H), 6.49 (s, 1H), 6.86 (s, 1H), 6.95-7.02 (m, 4H), 7.36 (t, J=8.1 Hz, 1H), 8.03 (t, J=8.4 Hz, 2H).

Step 6—To a solution of amine 8 (1.5 g, 3.4 mmol) in dimethyl sulfoxide (15.0 mL) was added diisopropylethylamine (2.0 mL, 10.2 mmol) and the product of Step 5, Example 1 (0.86 g, 3.4 mmol) at 25° C. The reaction mixture was allowed to stir at 60° C. over a period of 5 h. The resulting reaction mixture was diluted with ethyl acetate (250 mL), washed with water (2×100 mL) and dried over sodium sulphate. The crude product obtained upon evaporation of volatiles was purified through silica gel (230-400) column (25% ethyl acetate in petroleum ether) to give product 9 as a white solid 0.9 g (54%). mp: 48.5-53.2° C. $^1$H NMR (300 MHz, DMSO-d6) δ (ppm): 1.10-1.20 (m, 2H), 1.88 (bs, 1H), 2.26 (bs, 2H), 2.37 (bs, 2H), 2.70-2.71 (m, 1H), 3.31-3.38 (m, 4H), 3.83 (s, 3H), 6.36 (s, 1H), 6.84 (bs, 1H, CONH exchangeable $^1$H), 6.94-7.26 (m, 10H), 7.42 (t, J=7.8 Hz, 1H), 7.97 (d, J=8.4 Hz, 2H). $^{13}$C NMR (75 MHz, DMSO-d6) δ (ppm): 16.02, 24.76, 29.40, 34.49, 36.07, 44.32, 45.38, 52.44, 117.81, 118.27, 120.49, 123.40, 124.51, 125.61, 125.79, 126.33, 128.53, 130.59, 132.02, 139.85, 140.45, 142.43, 155.40, 158.04, 161.73 and 166.11. MS: 483 (M+H).

Example 8—Synthesis of 4-{3-[1-(2-phenyl-cyclopropylcarbamoyl)-piperidin-4-ylidenemethyl]-phenoxy}-benzoic acid

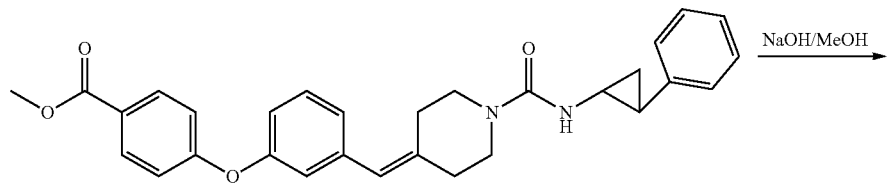

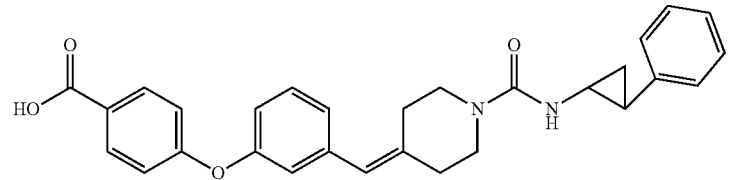

To a solution of product of Step 6, Example 7 (0.5 g, 1.03 mmol) in methanol (3.0 mL) was added a solution of sodium hydroxide (120 mg, 3.1 mmol) in water (2.0 mL) at 25° C. The reaction mixture was allowed to stir at 55° C. over a period of 16 h. The crude product obtained upon evaporation of the solvent was diluted with water (20.0 mL) and the aqueous layer washed with ethyl acetate (2×20 mL). Then aqueous layer was acidified (pH=2, 1.0 N HCl), saturated with solid NaCl and the product was extracted with ethyl acetate (2×150 mL). The combined organic layers were dried over sodium sulphate and concentrated to yield the product as a white solid 350 mg (72%). mp: 99.4-102.5° C. $^1$H NMR (300 MHz, DMSO-d6) δ (ppm): 1.15-1.29 (m, 2H), 1.88 (bs, 1H), 2.26 (bs, 2H), 2.37 (bs, 2H), 2.71 (bs, 1H), 3.32-3.38 (m, 4H), 6.36 (s, 1H), 6.84 (bs, 1H, CONH exchangeable $^1$H), 6.93-7.44 (m, 11H), 7.95 (d, J=8.4 Hz, 2H), 12.83 (bs, 1H). $^{13}$C NMR (75 MHz, DMSO-d6) δ (ppm): 16.02, 24.75, 29.40, 34.51, 36.07, 44.31, 45.37, 117.76, 118.17, 120.38, 123.43, 125.47, 125.79, 126.32, 128.54, 130.57, 132.13, 139.81, 140.41, 144.44, 155.59, 158.03, 163.36 and 167.22. MS: 467 (M−H).

Example 9—Synthesis of 4-(3-pyrrolidin-1-yl-benzyl)-piperidine-1-carboxylic acid-(2-phenyl-cyclopropyl)-amide

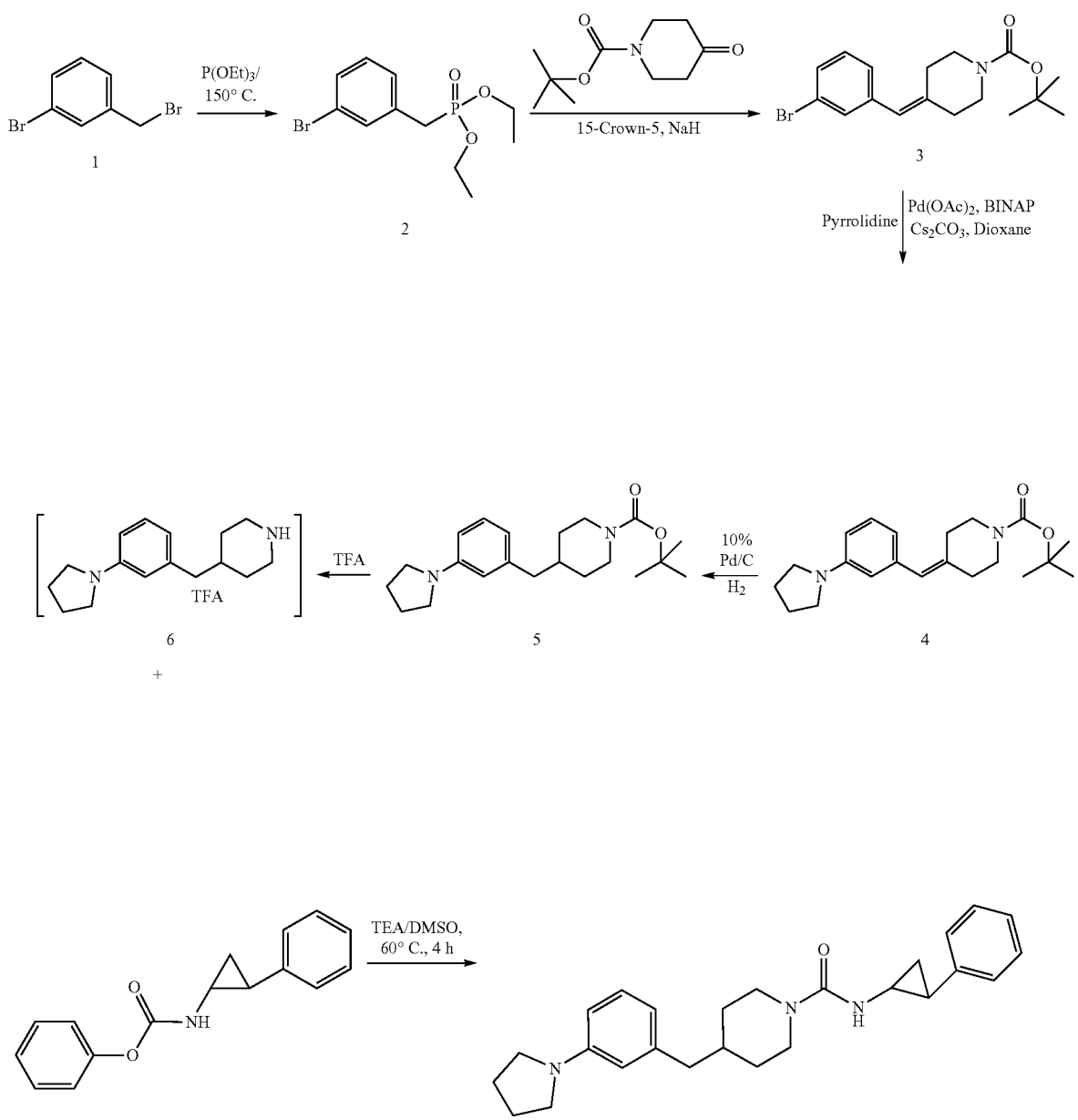

Step 1—A solution of 3-bromobenzyl bromide (6.0 g, 24.0 mmol) in triethyl phosphate (6.2 mL, 36.0 mmol) was heated at 130° C. over a period of 16 h. The reaction mixture was cooled and allowed to reach room temperature and the crude product obtained upon evaporation of volatiles was purified through silica gel (230-400) column (30% ethyl acetate in petroleum ether) to give product 2 as colorless oil 6.5 g (89%). $^1$H NMR (300 MHz, DMSO-d6) δ (ppm): 1.17 (t, J=7.2 Hz, 6H), 3.24 (s, 1H), 3.31 (s, 1H), 3.91-4.01 (m, 4H), 7.28-7.29 (m, 2H), 7.43-7.50 (m, 2H). MS: 307.0 (M+) and 309.0 (M+2).

Step 2—To a solution of 2 (3.0 g, 9.7 mmol) in THF (20 mL) was added 15-crown ether (0.04 mL, 0.19 mmol). The reaction was cooled (ice bath) and NaH (0.58 g, 14.6 mmol) added portion wise. The reaction mixture was allowed to stir at room temperature for 30 min and again cooled to ice temperature. To the above reaction mixture, a solution of 4-oxo-piperidine-1-carboxylic acid tert-butyl ester (1.95 g, 9.7 mmol) in THF (10 mL) was added at ice temperature and allowed to stir at room temperature over a period of 16 h. The resulting reaction mixture was diluted with water (100 mL), extracted with ethyl acetate (3×100 mL) and dried over sodium sulphate. The crude product obtained upon evaporation of volatiles was purified through silica gel (230-400) column (5% ethyl acetate in petroleum ether) to give product 3 as a yellow color oil 1.8 g (53%). $^1$H NMR (300 MHz, DMSO-d6) δ (ppm): 1.41 (s, 9H), 2.28 (bs, 2H), 2.38 (bs, 2H), 3.34-3.41 (m, 4H), 6.36 (s, 1H), 7.25-7.30 (m, 2H), 7.41-7.43 (m, 2H). MS: 252.0 (M-BOC).

Step 3—To a solution of compound 3 (2.0 g, 7.0 mmol) in 1,4-dioxane (20.0 mL) were added pyrrolidine (0.9 mL, 10.6 mmol), cesium carbonate (7.0 g, 21.2 mmol), racemic BINAP (0.9 g, 1.4 mmol) and palladium acetate (0.95 g, 1.4 mmol) under argon atmosphere at room temperature. The reaction mixture was stirred at room temperature for 30 min, followed by stirring under reflux for a period of 16 hours. The resulting reaction mass was filtered through a celite pad, washed with ethyl acetate (250 mL). The ethyl acetate layer was washed with water (2×100 mL), dried over sodium sulphate and concentrated. The crude product obtained was purified by silica gel column chromatography (15% ethyl acetate in petroleum ether) to obtain product 4 as a pale yellow oil 0.6 g (32%). $^1$H NMR (300 MHz, CDCl$_3$) δ (ppm): 1.49 (s, 9H), 2.01 (bs, 4H), 2.33-2.35 (m, 2H), 2.50-2.53 (m, 2H), 3.27-3.29 (m, 4H), 3.39-3.49 (m, 2H), 3.50-3.54 (m, 2H), 6.36-6.53 (m, 4H), 7.19 (t, J=8.1 Hz, 1H). MS: 343.7 (M+H).

Step 4—To a solution of compound 4 (0.6 g, 1.7 mmol) in tetrahydrofuran (10.0 mL) was added 10% Pd/C (240 mg). The reaction mass was stirred at room temperature under hydrogen gas pressure (1 kg/cm$^2$) over a period of two hours. After releasing hydrogen pressure, reaction mixture was filtered through celite pad, washed with tetrahydrofuran and filtrate concentrated to give product 5 as a pale yellow liquid (0.6 g). The crude product was taken to next step without further purification. $^1$H NMR (300 MHz, DMSO-d$_6$) δ (ppm): 1.10-1.21 (m, 2H), 1.49 (s, 9H), 1.64-1.72 (m, 3H), 1.98-2.03 (m, 4H), 2.49 (d, J=6.9 Hz, 2H), 2.65 (t, J=12.3 Hz, 2H). 3.27-3.31 (m, 2H), 4.07-4.15 (m, 2H), 6.35 (s, 1H), 6.42-6.47 (m, 2H), 7.14 (t, J=7.8 Hz, 1H). MS: 345.7 (M+H).

Step 5—To a solution of compound 5 (0.6 g, 1.7 mmol) in dichloromethane (6.0 mL) was added trifluoroacetic acid (3 mL) at ice temperature and the reaction mixture was stirred at room temperature for a period of 1 h. The brown colored oil 6 (0.6 g) obtained upon evaporation of volatiles was used in next step without additional purification.

Step 6—To a solution of amine 6 (600 mg, 1.9 mmol) in dimethyl sulfoxide (6.0 mL) was added N,N-diisopropylethylamine (1.1 mL, 5.8 mmol) and product of Step 5, Example 1 (0.5 g, 1.9 mmol) at 25° C. The reaction mixture was allowed to stir at 60° C. over a period of 5 h. The resulting reaction mixture was diluted with ethyl acetate (500 mL), washed with water (3×100 mL) and dried over sodium sulphate. The crude product obtained upon evaporation of volatiles was purified through silica gel (230-400) column (40% ethyl acetate in petroleum ether) and by preparative HPLC (phenomenex 250×221.20 mm, 10 μM, 0.1% TFA in water and acetonitrile mobile phase) to give product 7 as a pale yellow solid 160 mg (23%). mp: 145.6° C.-151.5° C. IR: 3334, 2842, 1620, 1600, 1545, 1252 and 752 cm$^{-1}$. $^1$H NMR: (300 MHz, DMSO-d6) δ (ppm): 0.95-1.19 (m, 3H), 1.13-1.17 (m, 1H), 1.50-1.55 (m, 2H), 1.63-1.66 (m, 1H), 1.81-1.87 (m, 1H), 1.93 (bs, 4H), 2.40-2.42 (m, 2H), 2.56-2.60 (m, 2H), 2.67-2.68 (m, 1H), 3.19 (bs, 4H), 3.90 (d, J=12.9 Hz, 2H), 6.32-6.40 (m, 3H), 6.71 (bs, 1H), 7.02-7.15 (m, 4H), 7.21-7.26 (m, 2H). MS: 404.5 (M+H).

Example 10—Synthesis of 4-(3-morpholin-4-yl-benzyl)-piperidine-1-carboxylic acid (2-phenyl-cyclopropyl)-amide

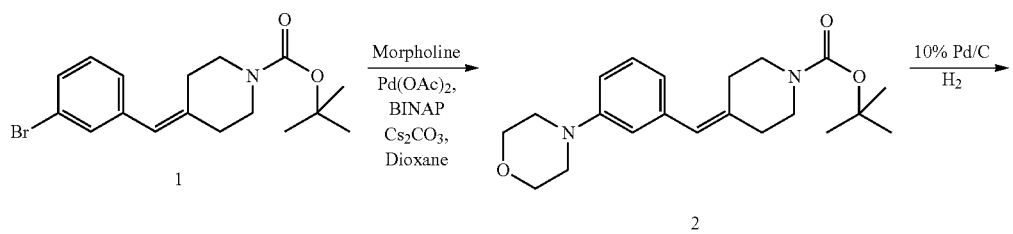

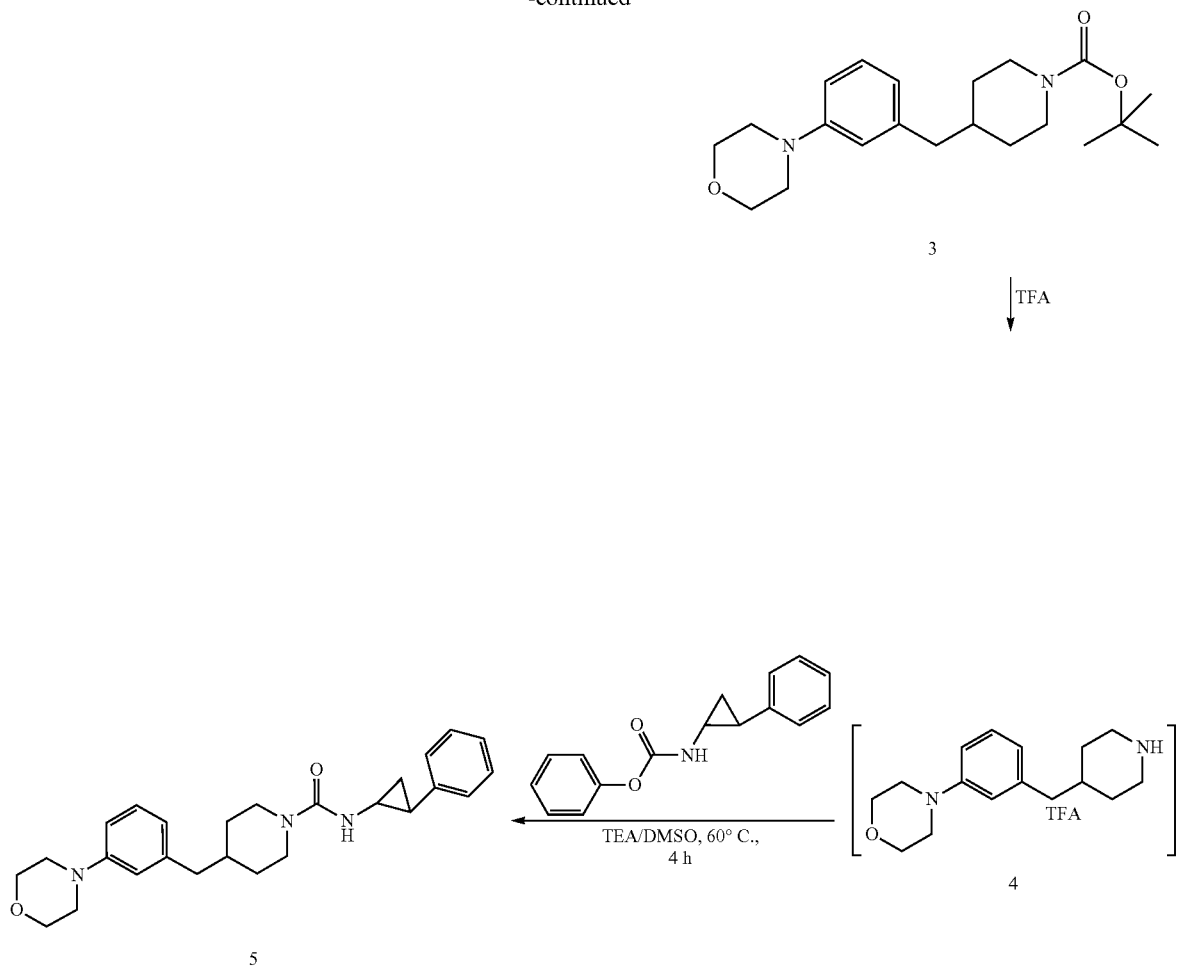

Step 1—To a solution of product of Step 2, Example 9 (1.5 g, 4.2 mmol) in 1,4-dioxane (15.0 mL) were added morpholine (0.45 mL, 5.1 mmol), cesium carbonate (4.1 g, 12.6 mmol), racemic BINAP (0.52 g, 0.84 mmol) and palladium acetate (0.56 g, 0.84 mmol) under argon atmosphere at room temperature. The reaction mixture was stirred at room temperature for 30 min, followed by stirring under reflux for 16 hours. The resulting reaction mass was cooled and filtered through celite pad and washed with ethyl acetate (250 mL). The ethyl acetate layer was washed with water (2×100 mL), organic layer dried over sodium sulphate and concentrated. The crude product obtained was purified by silica gel column chromatography (15% ethyl acetate in petroleum ether) to obtain the crude product 2 as a pale yellow oil 0.35 g.

Step 2—To a solution of compound 2 (0.85 g, 2.37 mmol) in tetrahydrofuran (10.0 mL) was added 10% Pd/C (350 mg). The reaction mass was stirred at room temperature under hydrogen gas pressure (1 kg/cm$^2$) for a period of two hours. After releasing hydrogen pressure, reaction mixture was filtered through celite pad, filtrate was concentrated to get the product 3 as a pale yellow liquid (0.8 g). The product was taken to next step without further purification.

Step 3—To a solution of crude compound 3 (0.8 g, 2.2 mmol) in dichloromethane (8.0 mL) was added trifluoroacetic acid (4 mL) at ice temperature and the reaction mixture was stirred at room temperature for a period of 1 h. The brown color oil 4 (0.8 g) obtained upon evaporation of volatiles was taken to next step without additional purification.

To a solution of amine 4 (800 mg, 2.3 mmol) in dimethyl sulfoxide (8.0 mL) was added diisopropylethylamine (1.3 mL, 7.0 mmol) and the product of Step 5, Example 1 (0.6 g, 2.3 mmol) at 25° C. The reaction mixture was allowed to stir at 60° C. for a period of 5 h. The resulting reaction mixture was diluted with ethyl acetate (500 mL), washed with water (3×100 mL) and dried over sodium sulphate. The crude product obtained upon evaporation of volatiles was purified through silica gel (230-400) column (50% ethyl acetate in petroleum ether) to give product 5 as a pale yellow solid 420 mg. mp: 182.3° C.-186.0° C. IR: 3330, 2841, 1620, 1600, 1545, 1247 and 756 cm$^{-1}$. $^1$H NMR (300 MHz, DMSO-d6) δ (ppm): 0.95-1.08 (m, 3H), 1.11-1.18 (m, 1H), 1.49-1.53 (m, 2H), 1.61-1.67 (m, 1H), 1.85-1.88 (m, 1H), 2.43-2.61 (m, 4H), 2.67-2.68 (m, 1H), 3.08 (t, J=4.5 Hz, 4H), 3.74 (t, J=4.5 Hz, 4H), 3.90 (d, J=12.6 Hz, 2H), 6.61 (d, J=7.2 Hz, 1H), 6.70-6.76 (m, 3H, one $^1$H is D$_2$O exchangeable), 7.07-7.15 (m, 4H), 7.22-7.27 (m, 2H). $^{13}$C NMR (75 MHz, DMSO-d6) δ (ppm): 16.01, 24.75, 32.08, 34.56, 37.96, 43.17, 43.98, 49.00, 66.61, 113.09, 116.43, 120.52, 125.77, 126.29, 128.53, 129.12, 141.31, 142.51, 151.50, 158.28. MS: 420.2 (M+H).

Example 11—Synthesis of 4-[3-(pyridin-2-yloxy)-phenoxy]-piperidine-1-carboxylic acid (2-phenyl-cyclopropyl)-amide

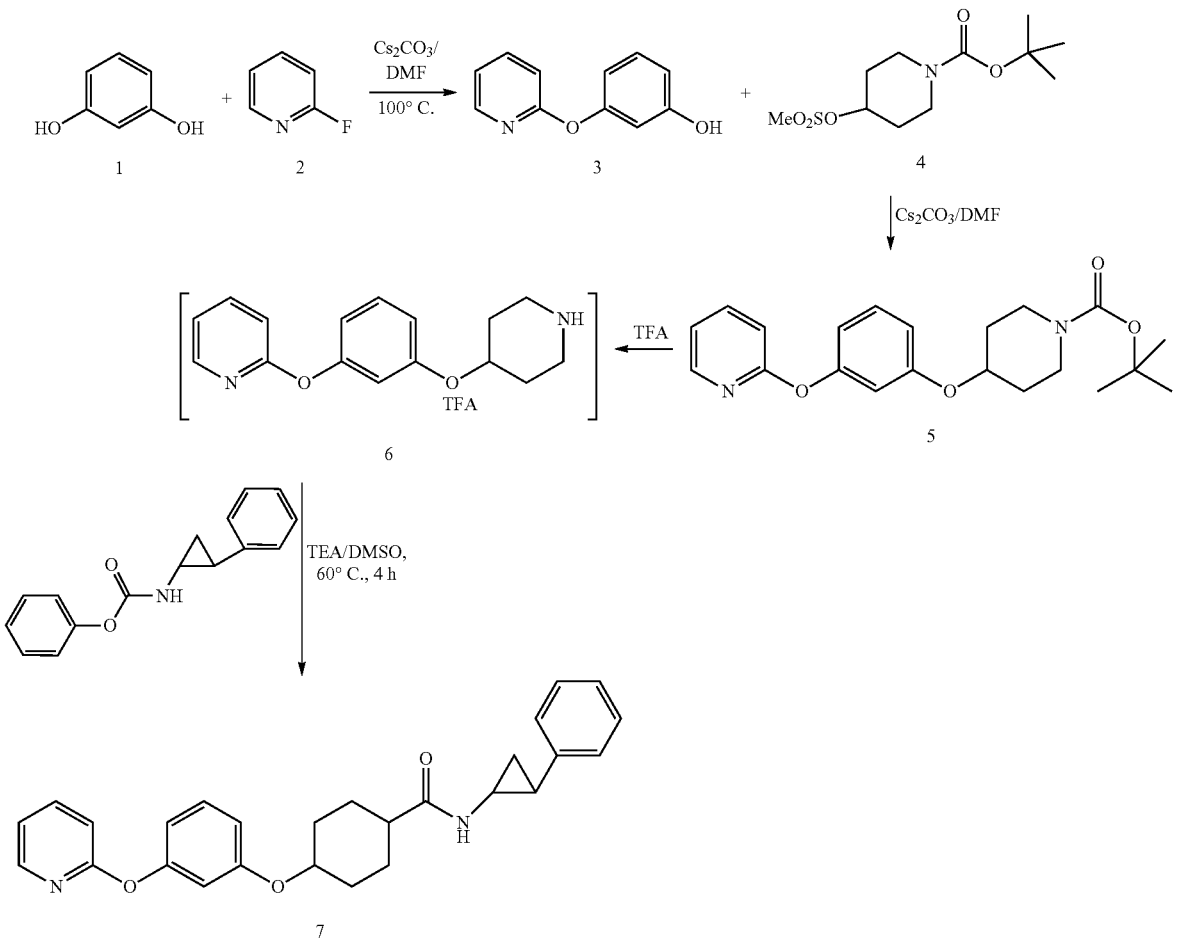

Step 1—To a solution of 1,3-dihydroxybenzene (1.0 g, 9.0 mmol) in DMF (10.0 mL) was added $Cs_2CO_3$ (5.92 g, 18.0 mmol) and 2-fluoropyridine (0.8 mL, 9.0 mmol). The reaction mixture was heated to 100° C. for a period of 16 h. Then the resulting mixture was allowed to reach room temperature, diluted with water (250 mL), extracted with ethyl acetate (3×500 mL) and the organic layer dried over sodium sulphate. The crude product obtained upon evaporation of volatiles was purified through silica gel (230-400) column (10% ethyl acetate in petroleum ether) to give product 3 as a pale yellow oil 400 mg (23%). $^1$H NMR (300 MHz, DMSO-d6) δ (ppm): 6.20 (s, 1H), 6.48-6.53 (m, 1H), 6.61 (d, J=8.1 Hz, 1H), 6.98 (d, J=8.1 Hz, 1H), 7.11-7.21 (m, 2H), 7.84 (t, J=8.1 Hz, 1H), 8.18 (bs, 1H), 9.61 (s, 1H, $D_2O$ exchangeable $^1$H). MS: 187.9 (M+H).

Step 2—To a solution of compound 3 (400 mg, 2.14 mmol) in DMF (8.0 mL) was added $Cs_2CO_3$ (1.4 g, 4.2 mmol) at room temperature. The reaction mixture was stirred for 5 min, then compound 4 (600 mg, 2.14 mmol) in DMF (2.0 mL) was added to the reaction mixture at room temperature and the reaction mixture was stirred at 65° C. for a period of 8 h. The reaction mixture was diluted with ethyl acetate (300 mL), washed with water (3×50 mL) and ethyl acetate layer dried over sodium sulphate. The crude product obtained upon evaporation of volatiles was purified through silica gel (230-400) column (50% ethyl acetate in petroleum ether) to give product 5 as a pale yellow oil 540 mg (67%). $^1$H NMR (300 MHz, DMSO-d6) δ (ppm): 1.40 (s, 9H), 1.48-1.51 (m, 2H), 1.89-1.92 (m, 2H), 3.14-3.16 (m, 2H), 3.63-3.68 (m, 2H), 4.56-4.58 (m, 1H), 6.65-6.68 (m, 1H), 6.75 (s, 1H), 6.80-6.84 (m, 1H), 6.99-7.02 (m, 1H), 7.14 (d, J=5.1 Hz, 1H), 7.29 (t, J=7.8 Hz, 1H), 7.85 (t, J=7.5 Hz, 1H), 8.17 (d, J=5.1 Hz, 1H). MS: 371.4 (M+H).

Step 3—To a solution of compound 5 (0.4 g, 0.8 mmol) in dichloromethane (8.0 mL) was added trifluoroacetic acid (2.0 mL) at ice temperature and the reaction mixture was stirred at room temperature over a period of 1 h. The brown color oil 6 obtained upon evaporation of volatiles was used in next step without additional purification.

To a solution of amine 6 (390 mg, 0.78 mmol) in dimethyl sulfoxide (5.0 mL) were added diisopropylethylamine (0.67 mL, 3.9 mmol) and the product of Step 5, Example 1 (198 mg, 0.78 mmol) at 25° C. The reaction mixture was allowed to stir at 60° C. for a period of 5 h. The resulting reaction mixture was diluted with ethyl acetate (250 mL), washed with water (3×10 mL) and dried over sodium sulphate. The crude product obtained upon evaporation of volatiles was purified through silica gel (230-400) column (70% ethyl acetate in petroleum ether) to give product as an off-white low melting solid. The product obtained was further purified by preparative HPLC to obtain product 7 as an off-white low melting solid 200 mg. mp: 43.9° C.-46.8° C. IR: 3313, 1621, 1586, 1423 and 1235 cm$^{-1}$. $^1$H NMR (300 MHz, DMSO-d6) δ (ppm): 1.07-1.09 (m, 1H), 1.14-1.18 (m, 1H), 1.46-1.49 (m, 2H), 1.86 (bs, 3H), 2.68-2.69 (m, 1H), 3.08 (t, J=9.6 Hz, 2H), 3.64-3.68 (m, 2H), 4.53 (bs, 1H), 6.64-6.67 (m, 1H), 6.74 (bs, 1H), 6.80 (bs, 1H), 6.83 (bs, 1H, D$_2$O exchangeable $^1$H), 7.00 (d, J=8.0 Hz, 1H), 7.08-7.14 (m, 4H), 7.21-7.31 (m, 3H), 8.82 (t, J=7.2 Hz, 2H), 8.16 (d, J=5.1 Hz, 1H). MS: 430.4 (M+H).

Example 12—Synthesis of 4-[3-(1H-pyrazol-4-yl)-benzyl]-piperidine-1-carboxylic acid (-2-phenyl-cyclopropyl)-amide

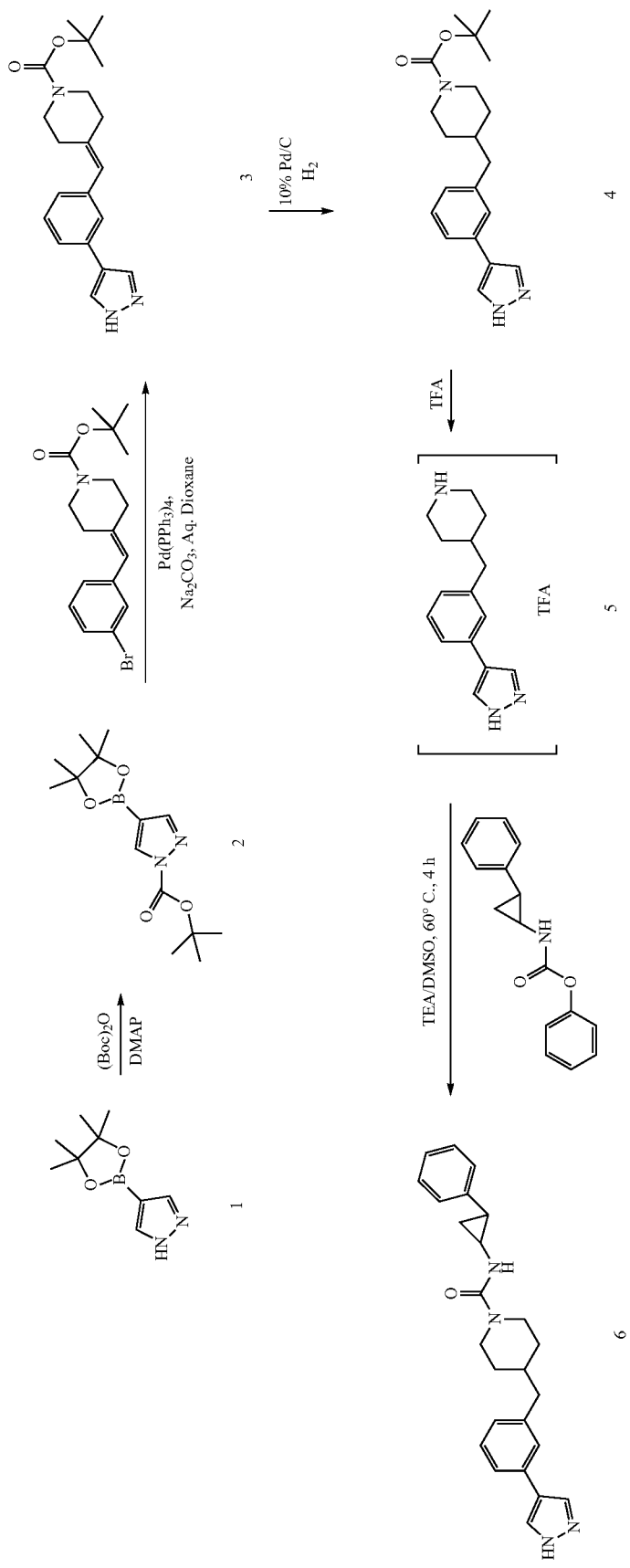

Step 1—To a cooled (0-5° C.) solution of compound 1 (2.0 g, 10.3 mmol, Sigma Aldrich) in dimethylformamide (20.0 mL) was added 4-dimethylaminopyridine (0.25 g, 2.0 mmol) and di-tert-butyl dicarbonate (3.0 mL, 15.4 mmol). The resulting reaction mass was stirred at room temperature for a period of 12 hours. The reaction was quenched with water (50.0 mL) and extracted with ethyl acetate (200 mL). The ethyl acetate layer was dried over anhydrous sodium sulphate and concentrated under reduced pressure. The crude product obtained was purified by silica gel column chromatography (15% ethyl acetate in petroleum ether) to obtain product 2 as an off-white solid 1.25 g (40%). $^1$H NMR (300 MHz, DMSO-d6) δ (ppm): 1.27 (s, 12H), 1.58 (s, 9H), 7.87 (s, 1H), 8.37 (s, 1H). MS: 195.3 (M-BOC+H).

Step 2—To a solution compound product of Step 2, Example 9 (1.0 g, 2.8 mmol) in DMF (10 mL) was added compound 2 (1.9 g, 5.6 mmol) and 2N sodium carbonate solution (4.3 mL, 8.5 mmol) at room temperature. Reaction mixture was stirred under argon atmosphere over a period of 10 minutes. Then tetrakis(triphenylphosphine)palladium(0) (0.33 g, 0.28 mmol) was added to the reaction mixture under argon. The resulting reaction mixture was stirred at room temperature for a period of 16 hours. Reaction mixture was quenched with water (100 mL) and extracted with ethyl acetate (500 mL), washed with water (2×250 mL) and brine (100 mL). Ethyl acetate layer was dried over sodium sulphate and concentrated. The crude product obtained upon evaporation of the solvent under reduced pressure was purified by silica gel column chromatography (40% ethyl acetate in petroleum ether) to obtain the product 3 as an off-white solid 550 mg (57%). $^1$H NMR (300 MHz, DMSO-d6) δ (ppm): 1.42 (s, 9H), 2.28-2.31 (m, 2H), 2.42-2.44 (m, 2H), 3.34-3.44 (m, 4H), 6.39 (s, 1H), 7.03 (d, J=7.5 Hz, 1H), 7.31 (t, J=7.5 Hz, 1H), 7.44-7.47 (m, 2H), 7.92 (s, 1H), 8.19 (s, 1H), 12.94 (s, 1H). MS: 338.1 (M−H).

Step 3—To a solution of compound 3 (0.5 g, 1.4 mmol) in 20% methanol in chloroform (10.0 mL) was added 10% Pd/C (200 mg). The reaction mass was stirred at room temperature under hydrogen gas pressure (1 kg/cm$^2$) over a period of 24 hours. Reaction mass was filtered through a celite pad, the filtrate was concentrated to get the product 4 as a pale yellow liquid (0.5 g). The crude product was taken for next step without further purification.

Step 4—To a solution of compound 4 (0.5 g, 1.6 mmol) in dichloromethane (5.0 mL) was added trifluoroacetic acid (2.5 mL) at ice temperature and the reaction mixture was stirred at room temperature over a period of 1 h. The brown color oil 5 (0.5 g) obtained upon evaporation of volatiles was used to next step without additional purification.

Step 5—To a solution of amine 5 (500 mg, 1.0 mmol) in dimethyl sulfoxide (5.0 mL) was added N,N-diisopropyl-ethylamine (0.8 mL, 4.2 mmol) and the product of Step 5, Example 1 (270 mg, 1.0 mmol) at 25° C. The reaction mixture was allowed to stir at 60° C. over a period of 5 h. The resulting reaction mixture was diluted with ethyl acetate (500 mL), washed with water (3×100 mL) and dried over sodium sulphate. The crude product obtained upon evaporation of volatiles was purified through silica gel (230-400) column (3% methanol in chloroform) to give product 6 as an off-white solid 210 mg. mp: 157.4° C.-163.4° C. IR: 3330, 1619, 1545, 1475 and 753 cm$^{-1}$. $^1$H NMR (300 MHz, DMSO-d6) δ (ppm): 1.01-1.17 (m, 4H), 1.51-1.55 (m, 2H), 1.82 (bs, 1H), 1.83-1.85 (m, 1H), 2.54-2.68 (m, 5H), 3.90 (d, J=12.6 Hz, 2H), 6.71 (d, J=2.7 Hz, 1H, D$_2$O exchangeable $^1$H), 6.98 (d, J=7.5 Hz, 1H), 7.07-7.15 (m, 3H), 7.21-7.27 (m, 3H), 7.41-7.43 (m, 2H), 7.90 (s, 1H), 8.17 (s, 1H), 12.91 (s, 1H, D$_2$O exchangeable $^1$H). $^{13}$C NMR (75 MHz, DMSO-d6) δ (ppm): 16.00, 24.74, 32.06, 34.53, 37.88, 42.81, 43.98, 121.69, 123.17, 125.77, 126.31, 127.05, 128.52, 128.99, 133.22, 141.06, 142.50, 158.22. MS: 401.3 (M+H).

Example 13—Synthesis of 4-[3-(1-methyl-1H-pyra-zol-4-yl)-benzyl]-piperidine-1-carboxylic acid (2-phenyl-cyclopropyl)-amide

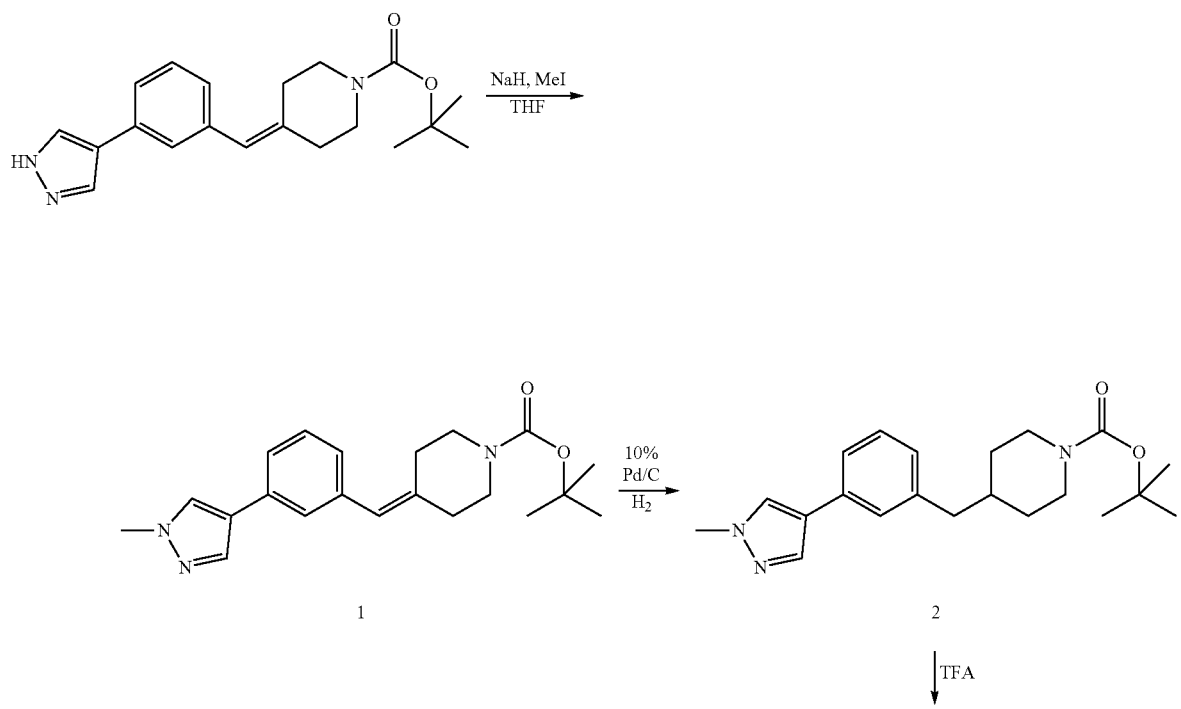

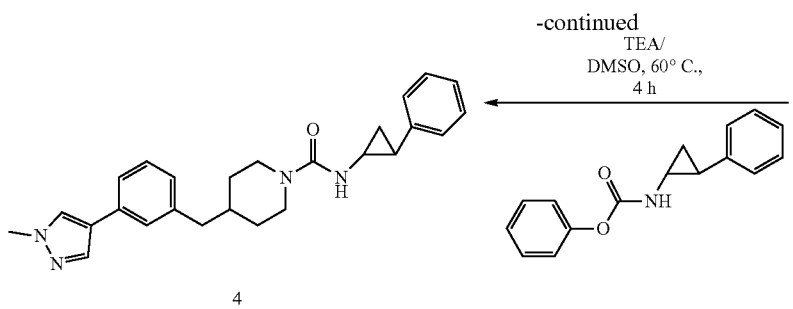
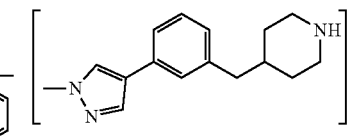

Step 1—To a cooled (0-5° C.) solution of product of Step 2, Example 12 (0.7 g, 2.0 mmol) in THF (25 mL) was added sodium hydride (0.25 g, 6.1 mmol) and methyl iodide (0.4 mL, 6.1 mmol). The resulting reaction mass was allowed to stir at room temperature over a period of 1 hour. Reaction mixture was quenched with water (100 mL) and extracted with ethyl acetate (500 mL). Organic layer was washed with water (2×250 mL) and brine (100 mL). Ethyl acetate layer was dried over anhydrous sodium sulphate and concentrated. The crude product obtained was purified by silica gel column chromatography (20% ethyl acetate in petroleum ether) to get the product 1 as an off-white solid 600 mg (83%). $^1$H NMR (300 MHz, DMSO-d6) δ (ppm): 1.45 (s, 9H), 2.30-2.31 (m, 2H), 2.42-2.44 (m, 2H), 3.35-3.44 (m, 4H), 3.89 (s, 3H), 6.39 (s, 1H), 7.02-7.05 (m, 1H), 7.30 (t, J=7.5 Hz, 1H), 7.39-7.43 (m, 2H), 7.85 (s, 1H), 8.14 (s, 1H). MS: 298.0 (M-t-butyl+H).

Step 2—To a solution of compound 1 (0.6 g, 1.7 mmol) in 20% methanol in chloroform (10.0 mL) was added 10% Pd/C (240 mg). The reaction mass was stirred at room temperature under hydrogen gas pressure (1 kg/cm$^2$) over a period of 16 hours. Reaction mass was filtered through celite pad, filtrate was concentrated to get the product 2 as a pale yellow liquid (0.6 g, 98%). The product obtained was taken to next step without further purification. $^1$H NMR (300 MHz, DMSO-d6) δ (ppm): 1.02-1.09 (m, 2H), 1.38 (s, 9H), 1.54-1.58 (m, 2H), 1.68-1.70 (m, 1H), 2.50-2.52 (m, 1H), 2.62-2.73 (m, 2H), 3.85-3.93 (m, 2H), 3.89 (s, 3H), 6.98 (d, J=7.2 Hz, 1H), 7.25 (t, J=7.5 Hz, 1H), 7.36 (s, 2H), 7.83 (s, 1H), 8.11 (s, 1H). MS: 300.2 (M-t-butyl+H).

Step 3—To a solution of compound 2 (0.6 g, 1.6 mmol) in dichloromethane (6.0 mL) was added trifluoroacetic acid (3.0 mL) at ice temperature and the reaction mixture was stirred at room temperature over a period of 1 h. The brown color oil 3 (0.6 g) obtained upon evaporation of volatiles was used in next step without additional purification.

Step 4—To a solution of amine 3 (600 mg, 1.6 mmol) in dimethyl sulfoxide (6.0 mL) was added diisopropylethylamine (1.2 mL, 6.4 mmol) and the product of Step 5, Example 1 (370 mg, 1.4 mmol) at 25° C. The reaction mixture was allowed to stir at 60° C. for a period of 5 h. The resulting reaction mixture was diluted with ethyl acetate (500 mL), washed with water (3×100 mL) and dried over sodium sulphate. The crude product obtained upon evaporation of volatiles was purified through silica gel (230-400) column (3% methanol in chloroform) to give product 4 as an off-white solid 350 mg (53%). mp: 158.4° C.-160.3° C. IR: 3353, 1619, 1544, 1473 and 752 cm$^{-1}$. $^1$H NMR (300 MHz, DMSO-d6) δ (ppm): 1.01-1.15 (m, 4H), 1.51-1.55 (m, 2H), 1.82-1.83 (m, 1H), 1.84-1.86 (m, 1H), 2.57-2.68 (m, 4H), 3.34-3.37 (m, 1H), 3.85 (s, 3H), 3.90 (d, J=13.2 Hz, 2H), 6.71 (d, J=2.7 Hz, 1H, D$_2$O exchangeable $^1$H), 6.98 (d, J=7.5 Hz, 1H), 7.07-7.15 (m, 3H), 7.21-7.27 (m, 3H), 7.36-7.38 (m, 2H), 7.83 (s, 1H), 8.11 (s, 1H). $^{13}$C NMR (75 MHz, DMSO-d6) δ (ppm): 16.00, 24.74, 32.05, 34.53, 37.89, 42.79, 43.99, 122.44, 122.97, 125.77, 126.10, 126.31, 127.15, 128.19, 128.52, 129.05, 132.91, 136.43, 141.11, 142.50, 158.21. MS: 415.0 (M+H).

Example 14—Synthesis of 4-(3-benzoimidazol-1-yl-benzyl)-piperidine-1-carboxylic acid (2-phenyl-cyclopropyl)-amide

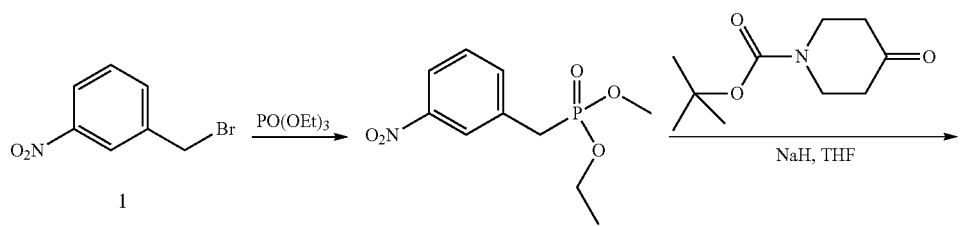

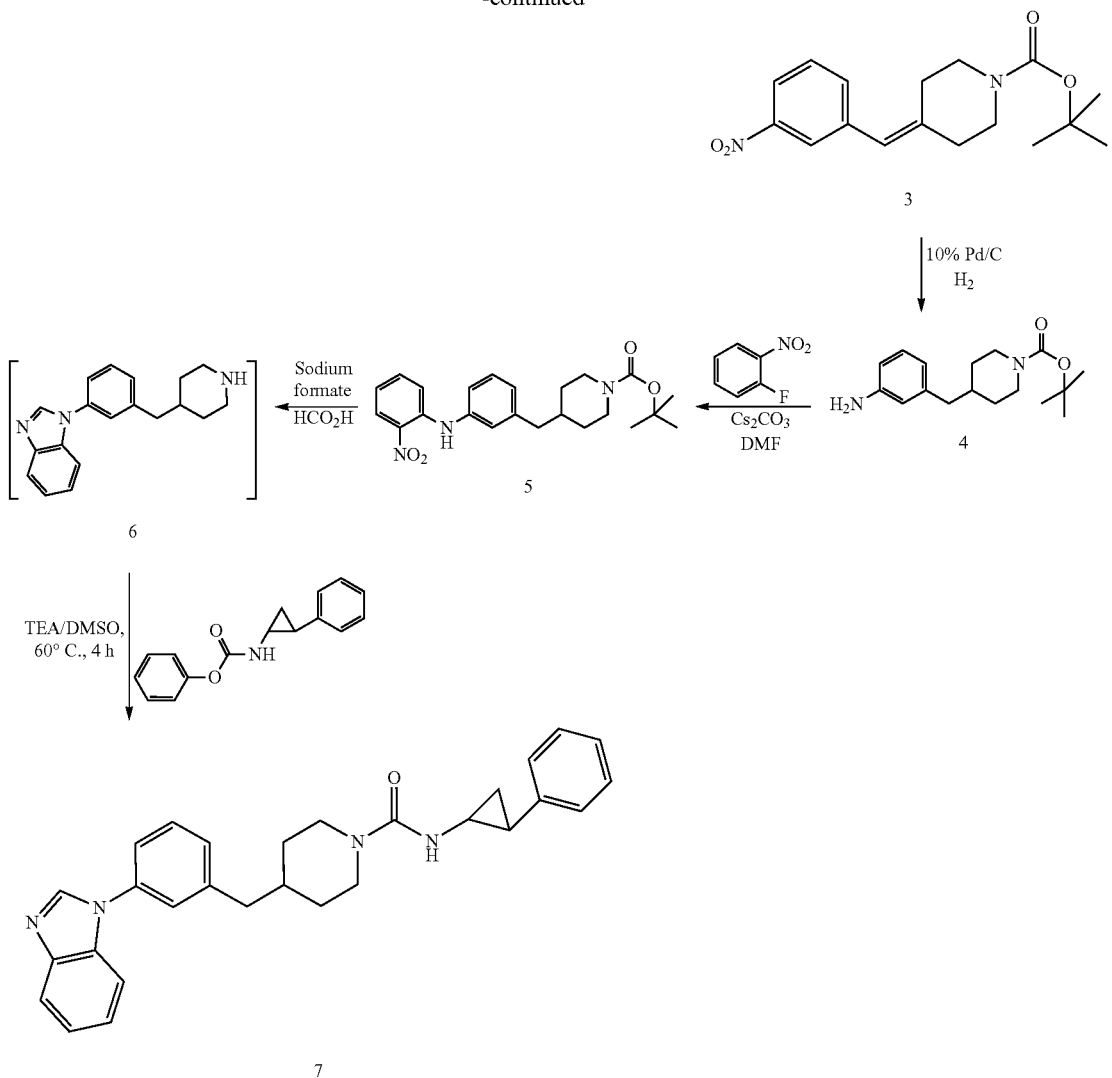

Step 1—A solution of compound 1 (5.0 g, 23.14 mmol) in triethyl phosphate (5.9 mL, 37.7 mmol) was heated at 130° C. over a period of 16 h. The reaction mixture was cooled to room temperature and the crude product obtained upon evaporation of volatiles was purified through silica gel (230-400) column (50% ethyl acetate in petroleum ether) to give product 2 as a pale yellow oil 4.9 g (89%). $^1$H NMR (300 MHz, DMSO-d6) δ (ppm): 1.09-1.21 (m, 6H), 3.44 (s, 1H), 3.51 (s, 1H), 3.93-4.07 (m, 4H), 7.60-7.66 (m, 1H), 7.73-7.76 (m, 1H), 8.11-8.14 (m, 1H), 8.19 (s, 1H). MS: 274.1 (M+1).

Step 2—To a solution of compound 2 (4.9 g, 20.3 mmol) in THF (50 mL) was added 15-crown ether (0.08 mL, 0.04 mmol). The reaction was cooled (ice bath) and NaH (1.22 g, 30.5 mmol) added portion wise. The reaction mixture was allowed to stir at room temperature for 30 min and again cooled to ice temperature. To the above reaction mixture, a solution of 4-oxo-piperidine-1-carboxylic acid tert-butyl ester (4.05 g, 20.3 mmol) in THF (10 mL) was added at ice temperature and allowed to stir at room temperature over a period 4 h. The resulting reaction mixture was diluted with water (100 mL), extracted with ethyl acetate (3×250 mL) and dried over sodium sulphate. The crude product obtained upon evaporation of volatiles was purified through silica gel (230-400) column (5% ethyl acetate in petroleum ether) to give product 3 as a yellow color oil 4.0 g (62%). $^1$H NMR (300 MHz, DMSO-d6) δ (ppm): 1.42 (s, 9H), 2.33 (t, J=5.7 Hz, 2H), 2.41 (t, J=5.7 Hz, 2H), 3.38-3.41 (m, 2H), 3.44 (t, J=5.7 Hz, 2H), 6.50 (s, 1H), 7.61-7.71 (m, 2H), 8.02 (s, 1H), 8.07-8.10 (m, 1H). MS: 219.2 (M-BOC+H), 263.1 (M-t-Butyl+1).

Step 3—To a solution of compound 3 (4.0 g, 12.5 mmol) in 90% methanol in dichloromethane (40.0 mL) was added 10% Pd/C (3.0 g). The reaction mass was stirred at room temperature under hydrogen gas pressure (1 kg/cm$^2$) over a period of 20 hours. Reaction mass was filtered through celite pad, filtrate was concentrated to get the product 4 as a pale yellow liquid (1.5 g, 41%). The product was taken to next step without further purification. $^1$H NMR (300 MHz, DMSO-d6) δ (ppm): 0.81-1.00 (m, 2H), 1.38 (s, 9H), 1.77-1.80 (m, 2H), 2.28-2.34 (m, 2H), 2.60-2.72 (m, 1H), 3.90 (t, J=12.6 Hz, 2H) 4.92 (s, 2H), 6.28-6.38 (m, 3H), 6.90 (t, J=12.6 Hz, 1H). MS: 191.1 (M-BOC+1).

Step 4—To a solution of compound 4 (1.5 g, 3.4 mmol) in DMF (8.0 mL) was added Cs$_2$CO$_3$ (8.9 g, 25.7 mmol) at room temperature. The reaction mixture was stirred for 5 min and 1-fluoro-2-nitrobenzene (0.8 g, 3.7 mmol) in DMF (2.0 mL) was added to the reaction mixture at room temperature and the mixture stirred at 100° C. for a period of 16 h. The reaction mixture was diluted with ethyl acetate (500 mL), washed with water (3×100 mL). The ethyl acetate layer was dried over sodium sulphate. The crude product obtained upon evaporation of volatiles was purified through silica gel (230-400) column (7% ethyl acetate in petroleum ether) to give product 5 as a reddish yellow oil 500 mg (35%). $^1$H NMR (300 MHz, DMSO-d6) δ (ppm): 0.97-1.08 (m, 2H), 1.38 (s, 9H), 1.54-1.58 (m, 2H), 1.65-1.68 (m, 1H), 2.40-2.52 (m, 2H), 2.64-2.73 (m, 2H), 3.91 (d, J=12.9 Hz, 2H), 6.87 (t, J=7.5 Hz, 1H), 7.01 (d, J=7.8 Hz, 1H), 7.13-7.20 (m, 3H), 7.30-7.35 (m, 1H), 7.50 (t, J=6.6 Hz, 1H), 8.11 (d, J=7.5 Hz, 1H), 9.35 (s, 1H). MS: 410.0 (M−H).

Step 5—To a solution of compound 5 (500 mg, 1.2 mmol) in formic acid (10 mL) were added sodium formate (290 mg, 4.3 mmol). and Pd/C (10 mol %, 120 mg, 0.01 mmol) at room 25° C. Then the reaction mixture was allowed to stir at 110° C. for a period of 18 h. The reaction mixture was allowed to cool (o room temperature and then filtered through celite with the aid of 20 mL of formic acid. The crude product obtained upon evaporation of the volatiles was dissolved in 5% methanol in dichloromethane (50 mL) and filtered to remove inorganic salts. The filtrate was concentrated to obtain product 6 as an off-white solid (350 mg). The crude product was taken to next without purification.

Step 6—To a solution of amine 6 (350 mg, 1.2 mmol) in dimethyl sulfoxide (5.0 mL) were added diisopropylethylamine (1.03 mL, 6.0 mmol) and the product of Step 5, Example 1 (186 mg, 1.2 mmol) at 25° C. The reaction mixture was allowed to stir at 60° C. for a period of 6 h. The resulting reaction mixture was diluted with ethyl acetate (300 mL), washed with water (3×50 mL) and dried over sodium sulphate. The crude product obtained upon evaporation of volatiles was purified through silica gel (230-400) column (1.5% methanol in dichloromethane) to give product 7 as an off-white solid 170 mg (31%). mp: 72.5° C.-76.4° C. IR: 3347, 2931, 16161, 1542, and 742 cm$^{-1}$. $^1$H NMR (300 MHz, DMSO-d6) δ (ppm): 1.00-1.14 (m, 4H), 1.54-1.57 (m, 2H), 1.71-1.79 (m, 1H), 1.80-1.84 (m, 1H), 2.48-2.65 (m, 5H), 3.92 (d, J=12.9 Hz, 2H), 6.72 (d, J=2.7 Hz, 1H, D$_2$O exchangeable $^1$H), 7.07-7.15 (m, 3H), 7.21-7.26 (m, 3H), 7.30-7.35 (m, 3H), 7.50-7.54 (m, 3H), 7.60-7.62 (m, 1H), 7.77-7.79 (m, 1H), 8.55 (s, 1H). MS: 451.0 (M+H).

Example 15—Synthesis of 4-(3-pyrrolidin-1-yl-benzylidene)-piperidine-1-carboxylic acid (2-phenyl-cyclopropyl)-amide

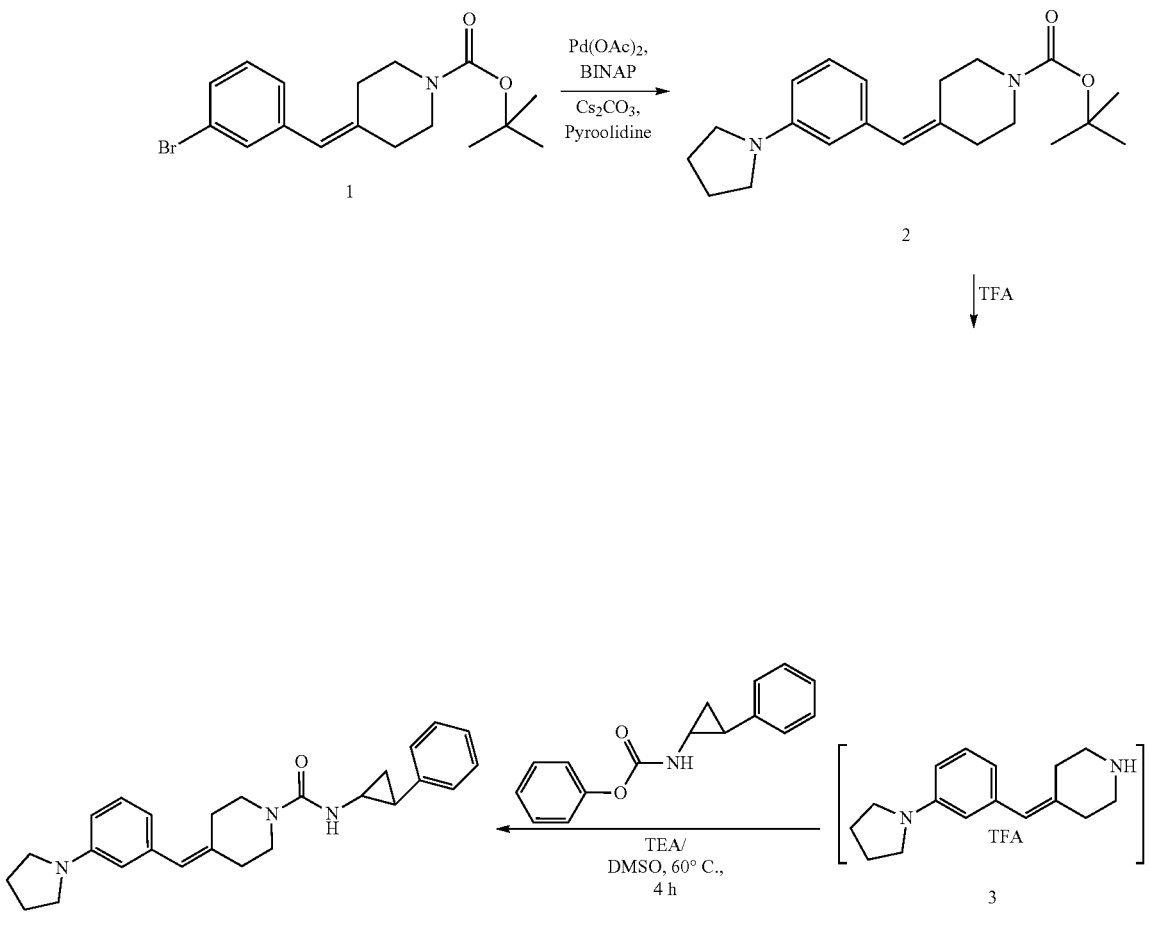

Step 1—To a solution of product of Step 2, Example 9 (2.0 g, 7.0 mmol) in 1,4-dioxane (20.0 mL) were added pyrrolidine (0.9 mL, 10.6 mmol), cesium carbonate (7.0 g, 21.2 mmol), racemic BINAP (0.9 g, 1.4 mmol) and palladium acetate (0.95 g, 1.4 mmol) under argon atmosphere at room temperature. The reaction mixture was stirred at room temperature for 30 min, followed by stirring under reflux for a period of 16 hours. The resulting reaction mass was filtered through a celite pad, washed with ethyl acetate (250 mL). The ethyl acetate layer was washed with water (2×100 mL), dried over sodium sulphate and concentrated. The crude product obtained was purified by silica gel column chromatography (15% ethyl acetate in petroleum ether) to obtain the product 2 as a pale yellow oil 0.6 g (32%). $^1$H NMR (300 MHz, CDCl$_3$) δ (ppm): 1.49 (s, 9H), 2.01 (bs, 4H), 2.33-2.35 (m, 2H), 2.50-2.53 (m, 2H), 3.27-3.29 (m, 4H), 3.39-3.49 (m, 2H), 3.50-3.54 (m, 2H), 6.36-6.53 (m, 4H), 7.19 (t, J=8.1 Hz, 1H). MS: 343.7 (M+1).

Step 2—To a solution of compound 2 (0.6 g, 1.7 mmol) in dichloromethane (6.0 mL) was added trifluoroacetic acid (3 mL) at ice temperature and the reaction mixture was stirred at room temperature over a period of 1 h. The brown color oil 3 (0.6 g) obtained upon evaporation of volatiles was used in next step without additional purification.

Step 3—To a solution of amine 3 (600 mg, 1.9 mmol) in dimethyl sulfoxide (6.0 mL) was added diisopropylethylamine (1.1 mL, 5.8 mmol) and the product of Step 5, Example 1 (0.5 g, 1.9 mmol) at 25° C. The reaction mixture was allowed to stir at 60° C. over a period of 5 h. The resulting reaction mixture was diluted with ethyl acetate (500 mL), washed with water (3×100 mL) and dried over sodium sulphate. The crude product obtained upon evaporation of volatiles was purified through silica gel (230-400) column (40% ethyl acetate in petroleum ether) to give product 4 as an off-white solid 300 mg (42%). mp: 145.7° C.-147.4° C. IR: 3292, 2963, 1626, 1533, 1263 and 746 cm$^{-1}$. $^1$H NMR (300 MHz, CDCl$_3$) δ (ppm): 1.22-1.26 (m, 2H), 2.02 (bs, 5H), 2.38-2.41 (m, 2H), 2.56-2.59 (m, 2H), 2.88 (bs, 1H), 3.30 (bs, 4H), 3.36-3.40 (m, 2H), 3.47-3.51 (m, 2H), 4.87 (bs, 1H, D$_2$O exchangeable $^1$H), 6.38-6.52 (m, 3H), 7.19-7.46 (m, 7H). $^{13}$C NMR (75 MHz, CDCl$_3$) δ (ppm): 16.01, 24.75, 32.08, 34.56, 37.96, 43.17, 43.98, 49.00, 66.61, 113.09, 116.43, 120.52, 125.77, 126.29, 128.53, 129.12, 141.31, 142.51, 151.50, 158.28. MS: 402.7 (M+H).

Example 16—Synthesis of phenyl N-[(1R,2S)-2-phenylcyclopropyl] carbamate

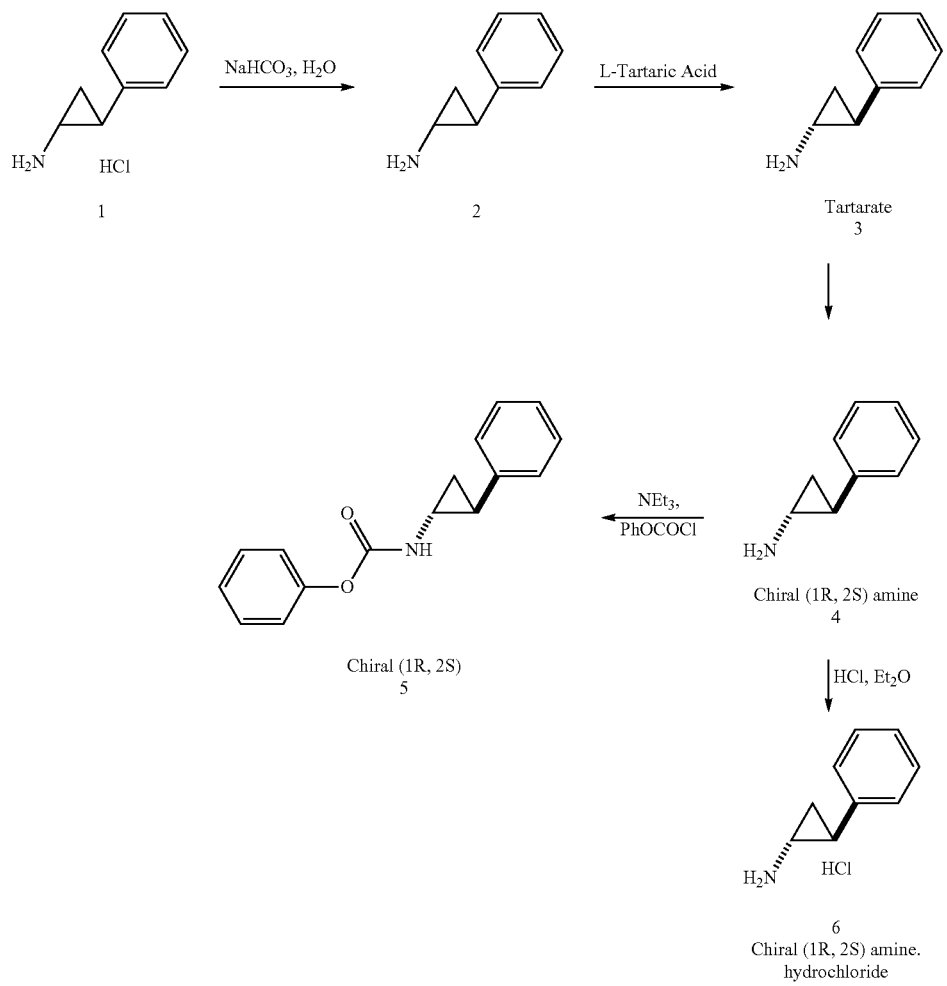

A general methodology described in literature (WO 2013/057322) was used to synthesize the chiral intermediate above.

Step 1—To a suspension of trans-2-phenyl-cyclopropylamine hydrochloride (100 g, 0.59 mol) in water (500 mL) was added saturated sodium bicarbonate solution at 0-5° C. over a period of 20 min and basified to pH>7. The reaction mixture was stirred at 25-30° C. over a period of 2 h. The reaction mixture was extracted with dichloromethane (3×700 mL), separated organic phase was dried over sodium sulphate and concentrated to yield 2-phenyl-cyclopropylamine as an off-white solid 2 (71.2 g, 92%).

Step 2—To a solution of trans-2-phenyl-cyclopropylamine (70 g, 0.52 mol) in ethanol (700 mL) was added L (+) tartaric acid (79 g, 0.52 mol) at 0-5° C. and stirred at 25-30° C. for 1 h. After reaction completion, the solid was filtered and dried to yield 2-phenyl-cyclopropylamine as tartrate salt (133 g). Isopropanol: water (3:1) (1.3 L) was added to the above salt (130 g) and stirred at 70° C. over a period of 2 h. The reaction mixture was allowed to cool to room temperature over a period of 1 h. The solid separated was collected by filtration to yield (1R,2S)—N-{[(2R,3R)-3-carboxy-2,3-dihydroxypropanoyl]oxy}-2-phenylcyclopropan-1-aminium (3) as a white solid (60 g, 90%).

Step 3—To a solution of (1R,2S)—N-{[(2R,3R)-3-carboxy-2,3-dihydroxypropanoyl]oxy}-2-phenylcyclopropan-1-aminium (3) (60 g, 0.19 mol) in water (200 mL) was added 1.0 M sodium hydroxide (194 mL, 0.19 mol) at 0-5° C. over a period of 20 min and stirred for 1 h. The aqueous phase was extracted with ethyl acetate (2×700 mL). The combined extracts were washed with water (2×400 mL), brine (400 mL), dried over sodium sulphate and concentrated under reduced pressure to yield (1R,2S)-2-phenyl-cyclopropylamine as pale yellow solid 4 (25 g, 87%).

Step 4—To a suspension of amine 4 (15.0 g, 88.0 mmol) in dichloromethane (150 mL) was added triethylamine (36.0 mL, 0.26 mol), phenyl chloroformate (20.7 g, 0.13 mol) at ice bath temperature. Then ice bath was removed and reaction mixture was allowed to stir at room temperature over a period of 1 h. The resulting reaction mixture was diluted with ethyl acetate (1.0 L), washed with water (2×200 mL) and dried over sodium sulphate. The crude product obtained upon evaporation of volatiles was purified through silica gel (230-400) column (10% ethyl acetate in petroleum ether) to give product 5 as a white solid 16.0 g (71%). ¹H NMR (400 MHz, DMSO-d6) δ (ppm): 1.15-1.25 (m, 2H), 2.04-2.08 (m, 1H), 2.72-2.75 (m, 1H), 7.10-7.40 (m, 10H), 8.17 (bs, 1H). MS (M+H) 254.3.

Step 5—To a stirring solution of (1R,2S)-2-phenyl-cyclopropylamine 4 (25.0 g, 0.19 mol) in diethyl ether (150 mL) was added 2.0 M HCl in ether (140 mL, 0.28 mol) at 0-5° C. The reaction mixture was allowed to stir at 20-25° C. over a period of 30 min. The reaction mixture was concentrated under reduced pressure. The resulted reaction mass was washed with diethyl ether (2×100 mL) to yield product 6, hydrochloric acid salt of (1R,2S)-2-phenyl-cyclopropylamine as an off-white solid 30.0 g (95%). mp: 179.2-180.1° C.; IR: 3643, 3054, 1979, 1501, 1160, 799, 743, 696 cm⁻¹. ¹H NMR (400 MHz, DMSO-d6) δ (ppm): 1.14-1.19 (m, 1H), 1.43-1.48 (m, 1H), 2.38-2.43 (m, 1H), 2.72-2.76 (m, 1H), 7.09-7.24 (m, 3H), 7.22-7.33 (m, 2H), 8.81 (bs, 3H). MS (M+H) 134.3. Chiral HPLC purity: 100%. The chirality of 6 was further confirmed by matching analytical and spectral data with authentic sample, (1R,2S)-2-phenylcyclopropylamine hydrochloride, purchased from Sigma-Aldrich.

Example 17—Synthesis of 4-[3-(5-trifluoromethyl-pyridin-2-yloxy)-benzylidene]-piperidine-1-carboxylic acid [(1S,2R)-2-phenyl-cyclopropyl)]-amide

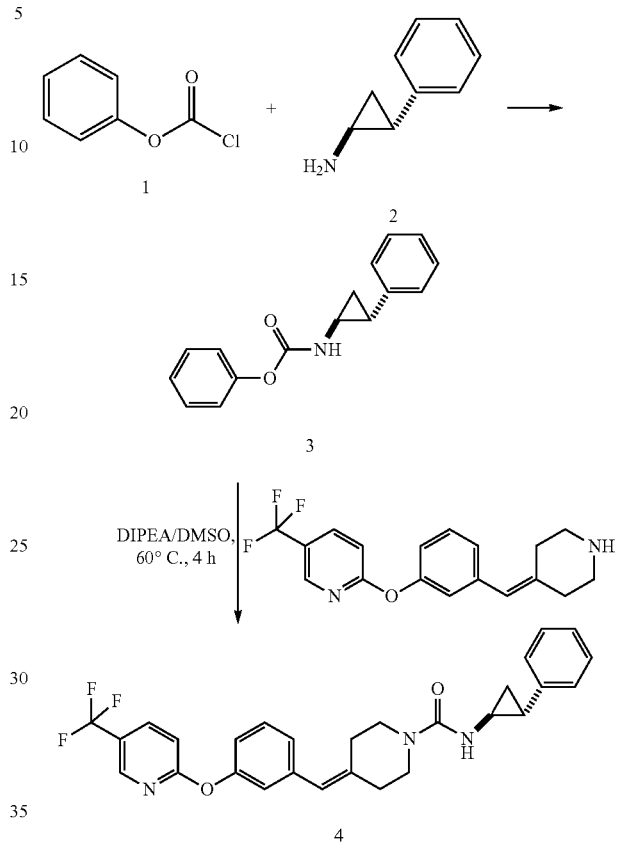

Step 1—To a suspension of (1S,2R)-2-phenylcyclopropan-1-amine 2 (500 mg, 2.95 mmol) in dichloromethane (5.0 mL) was added triethylamine (1.21 mL, 8.85 mol), phenyl chloroformate 1 (0.41 mL, 3.3 mol) at ice bath temperature. Then ice bath was removed and reaction mixture allowed to stir at room temperature over a period of 1 h. The resulting reaction mixture was diluted with ethyl acetate (1.0 L), washed with water (2×200 mL) and dried over sodium sulphate. The crude product obtained upon evaporation of volatiles was purified through silica gel (230-400) column (10% ethyl acetate in petroleum ether) to give product 3 as a white solid 500 mg (71%). ¹H NMR (400 MHz, DMSO-d6) δ (ppm): 1.19-1.26 (m, 2H), 2.05-2.08 (m, 1H), 2.72-2.75 (m, 1H), 7.11-7.38 (m, 10H), 8.18 (bs, 1H). MS (M+H) 254.5.

Step 2—To a solution of product of Step 5, Example 3 (1.0 g, 2.2 mmol) in dimethyl sulfoxide (10 mL) was added diisopropylethylamine (1.2 mL, 6.6 mmol) and 3 (556 mg, 2.2 mmol) at 25° C. The reaction mixture was allowed to stir at 60° C. over a period of 4 h. The resulting reaction mixture was diluted with ethyl acetate (300 mL), washed with water (3×100 mL) and dried over sodium sulphate. The crude product obtained upon evaporation of volatiles was purified through silica gel (230-400) column (40% ethyl acetate in petroleum ether) to give product 4 as a white solid 770 mg (70%). mp: 100.2° C.-101.0° C. IR: 3329, 1622, 1531, 1487, 1329, 1076 cm⁻¹. ¹H NMR (400 MHz, DMSO-d6) δ (ppm): 1.08-1.18 (m, 2H), 1.85-1.90 (m, 1H), 2.27 (t, J=5.6 Hz, 2H), 2.40 (t, J=5.2 Hz, 2H), 2.69-2.72 (m, 1H), 3.32 (t, J=6.0 Hz, 2H), 3.38 (t, J=6.0 Hz, 1H), 6.37 (s, 1H), 6.85 (d, J=3.2

Hz, 1H), 7.04-7.41 (m, 10H), 8.22-8.25 (m, 1H), 8.58 (bs, 1H). MS: 494.3 (M+H). HPLC purity: 99.78%. Chiral HPLC purity: 100%.

Example 18—Synthesis of 4-[3-(5-trifluoromethyl-pyridin-2-yloxy)-benzylidene]-piperidine-1-carboxylic acid [(1R,2S)-2-phenyl-cyclopropyl)]-amide

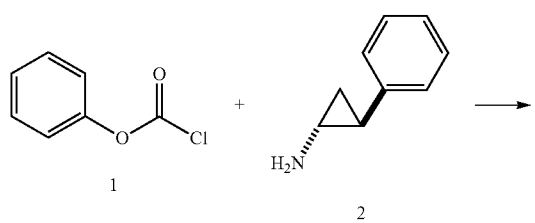

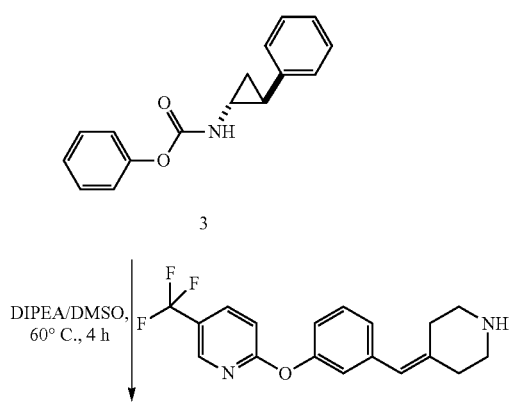

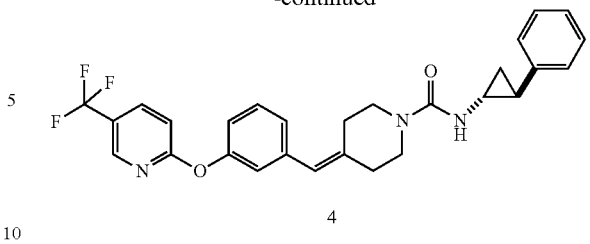

Step 1—To a suspension of (1R,2S)-2-phenyl-cyclopropylamine 2 (500 mg, 2.95 mmol) in dichloromethane (5.0 mL) was added triethylamine (1.21 mL, 8.85 mol), phenyl chloroformate 1 (0.41 mL, 3.3 mol) at ice bath temperature. Then ice bath was removed and reaction mixture was allowed to stir at room temperature over a period of 1 h. The resulting reaction mixture was diluted with ethyl acetate (250 mL), washed with water (2×100 mL) and dried over sodium sulphate. The crude product obtained upon evaporation of volatiles was purified through silica gel (230-400) column (10% ethyl acetate in petroleum ether) to give product 3 as a white solid 495 mg (70%). $^1$H NMR (400 MHz, DMSO-d6) δ (ppm): 1.15-1.25 (m, 2H), 2.04-2.08 (m, 1H), 2.72-2.75 (m, 1H), 7.10-7.40 (m, 10H), 8.17 (bs, 1H). MS (M+H) 254.3.

Step 2—To a solution of product of Step 5, Example 3 (1.0 g, 2.2 mmol) in dimethyl sulfoxide (10 mL) was added diisopropylethylamine (1.2 mL, 6.6 mmol) and 3 (556 mg, 2.2 mmol) at 25° C. The reaction mixture was allowed to stir at 60° C. over a period of 4 h. The resulting reaction mixture was diluted with ethyl acetate (300 mL), washed with water (3×100 mL) and dried over sodium sulphate. The crude product obtained upon evaporation of volatiles was purified through silica gel (230-400) column (40% ethyl acetate in petroleum ether) to give product 4 as a white solid 715 mg (65%). mp: 101.8° C.-103.2° C. IR: 3329, 1623, 1531, 1388, 1329, 1076, 697 cm$^{-1}$. $^1$H NMR (400 MHz, DMSO-d6) δ (ppm): 1.07-1.18 (m, 2H), 1.85-1.90 (m, 1H), 2.25-2.40 (m, 4H), 2.67-2.75 (m, 2H), 2.69-2.72 (m, 1H), 3.31 (t, J=6.0 Hz, 2H), 3.38 (t, J=5.6 Hz, 1H), 6.36 (s, 1H), 6.85 (s, 1H), 7.04-7.15 (m, 6H), 7.22-7.41 (m, 4H), 8.22-8.24 (m, 1H), 8.58 (bs, 1H). MS: 494.3 (M+H). HPLC purity: 99.96%. Chiral HPLC purity: 100%.

Example 19—Synthesis of 4-({3-[(5-methylpyridin-2-yl)oxy]phenyl} methylidene)-N-[2-phenylcyclopropyl]piperidine-1-carboxamide

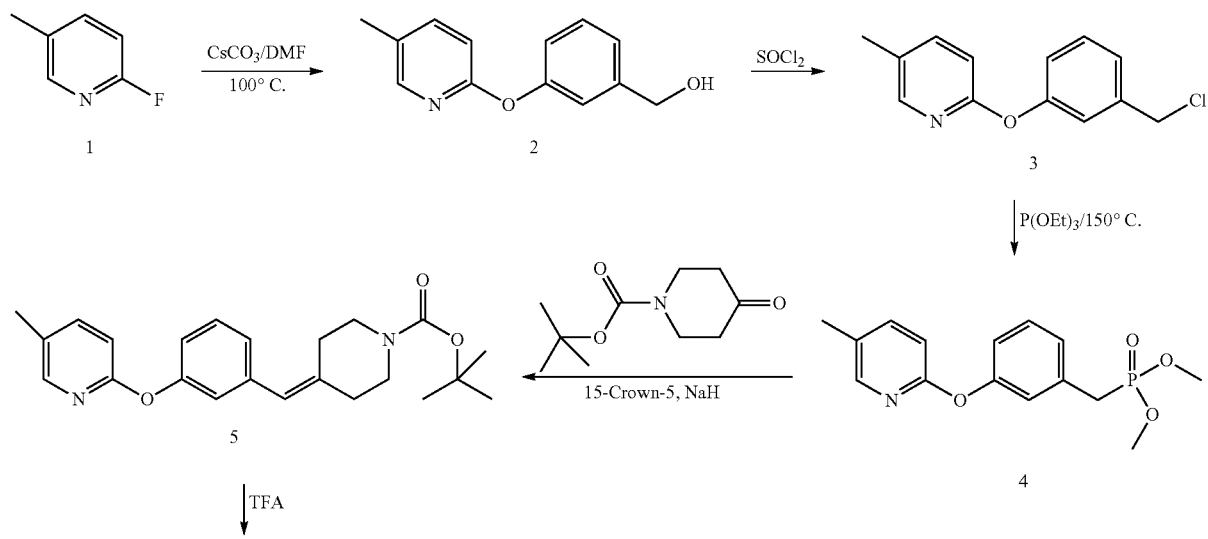

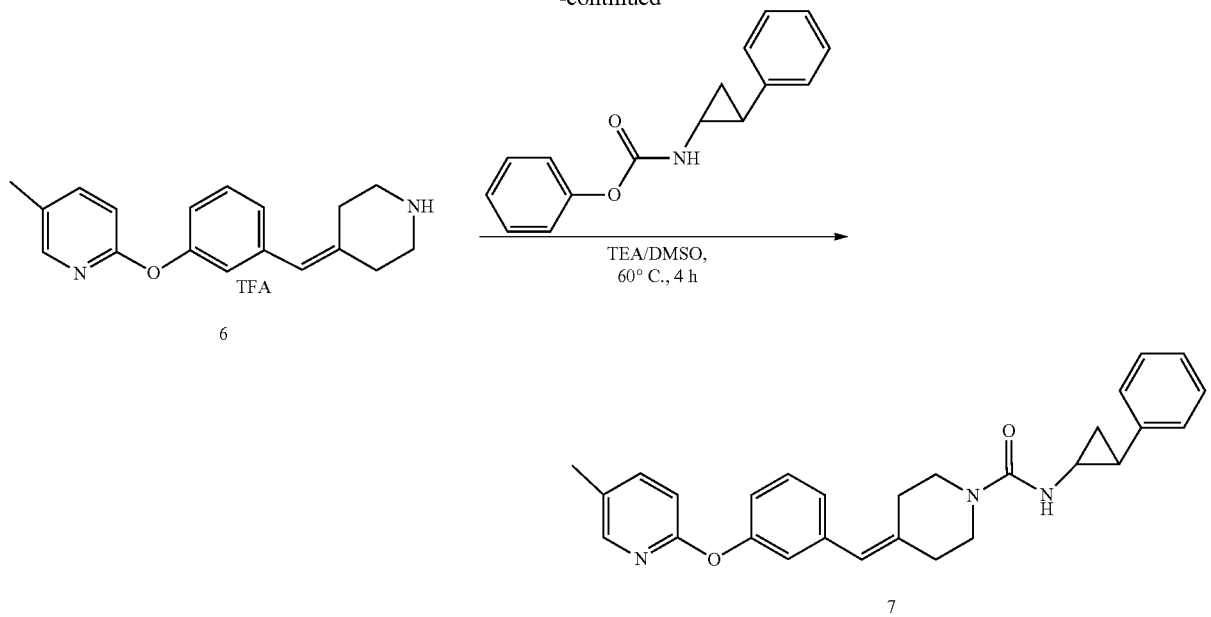

Step 1—To a solution of 2-fluoro-5-methyl-pyridine 1 (14.76 g, 0.13 mol) in DMF (150 mL) was added 3-hydroxyphenyl-methanol (15.0 g, 0.12 mol) and cesium carbonate (59.0 g, 0.18 mol) at room temperature. The reaction mixture was stirred at 100° C. over a period of 5 h. Then the resulting mixture was cooled and allowed to reach room temperature, diluted with water (250 mL), extracted with ethyl acetate (3×500 mL) and the organic layer was dried over sodium sulphate. The crude product obtained upon evaporation of volatiles was purified through silica gel (230-400) column (30% ethyl acetate in petroleum ether) to give product 2 as a pale yellow oil 6.0 g (23%). $^1$H NMR (300 MHz, DMSO-d6) δ (ppm): 2.25 (s, 3H), 4.40 (d, J=6.0 Hz, 2H), 5.22 (t, J=6.0 Hz, 1H), 6.91-6.94 (m, 2H), 7.01 (s, 1H), 7.11 (d, J=7.5 Hz, 1H), 7.34 (t, J=7.5 Hz, 1H), 7.66-7.69 (m, 1H), 7.98 (d, J=2.1 Hz, 1H). MS: (M+H) 216.2.

Step 2—To a solution of [3-(5-methyl-pyridin-2-yloxy)-phenyl]-methanol 2 (6.0 g, 0.027 mol) in dichloromethane (60 mL) was added thionyl chloride (2.3 mL, 0.03 mol) drop wise while stirring reaction in an ice bath. After removal of ice-bath, the reaction mixture was allowed to stir at room temperature over a period of 1 h. Then volatiles were evaporated under reduced pressure and diluted with toluene (25 mL) and toluene was evaporated under reduced pressure. This azeotropic process was repeated 3 times to obtain product 3 as pale brown color oil (6.2 g, 95%). $^1$H NMR (300 MHz, DMSO-d6) δ (ppm): 2.25 (s, 3H), 4.76 (s, 2H), 6.95-6.98 (m, 2H), 7.15-7.26 (m, 2H), 7.38-7.40 (m, 1H), 7.66-7.69 (m, 1H), 7.99-8.0 (m, 1H). MS: (M+H) 234.3.

Step 3—A solution of 2-(3-chloromethyl-phenoxy)-5-methyl-pyridine (6.2 g, 0.026 mol) in triethyl phosphate (7.3 mL, 0.042 mol) was heated at 150° C. over a period of 6 h. The reaction mixture was allowed to reach room temperature and the crude product obtained upon evaporation of volatiles was purified through silica gel (230-400) column (60% ethyl acetate in petroleum ether) to give product 4 as a pale yellow oil 8.3 g. The product contained unused triethyl phosphate and was used in next step without additional purification. $^1$H NMR (300 MHz, DMSO-d6) δ (ppm): 1.13-1.23 (m, 6H), 2.25 (s, 3H), 3.20-3.27 (m, 2H), 3.89-3.99 (m, 4H), 6.91-6.99 (m, 3H), 7.09 (d, J=7.4 Hz, 1H), 7.32 (t, J=8.1 Hz, 1H), 7.66-7.69 (m, 1H), 7.98-8.32 (m, 1H). MS: (M+H) 336.1.

Step 4—To a solution of [3-(5-methyl-pyridin-2-yloxy)-benzyl]-phosphonic acid diethyl ester 4 (8.3 g, 0.024 mol) in THF (40 mL) was added 15-crown ether (0.1 g, 0.48 mmol). The reaction was cooled (ice bath) and NaH (1.44 g, 0.036 mol) was added portion wise. The reaction mixture was allowed to stir at room temperature for 30 min and again cooled to ice temperature. To the above reaction mixture, a solution of 4-oxo-piperidine-1-carboxylic acid tert-butyl ester (4.9 g, 0.024 mol) in THF (40 mL) was added at ice temperature and allowed to stir at room temperature over a period 16 h. The resulting reaction mixture was diluted with water (250 mL), extracted with ethyl acetate (3×500 mL) and dried over sodium sulphate. The crude product obtained upon evaporation of volatiles was purified through silica gel (230-400) column (3% ethyl acetate in petroleum ether) to give product 5 as a pale yellow color oil (6.7 g, 76%). $^1$H NMR (300 MHz, CDCl3) δ (ppm): 1.41 (s, 9H), 2.25-2.29 (m, 5H), 2.39 (t, J=6.0 Hz, 2H), 3.36-3.42 (m, 4H), 6.36 (s, 1H), 6.90-6.95 (m, 3H), 7.02-7.05 (m, 1H), 7.35 (t, J=7.8 Hz, 1H), 7.66-7.70 (m, 1H), 7.98 (d, J=2.4 Hz, 1H). MS: (M+H) 381.2.

Step 5—To a solution of 4-[3-(5-methyl-pyridin-2-yloxy)-benzylidene]-piperidine-1-carboxylic acid tert-butyl ester 5 (6.7 g, 0.017 mol) in dichloromethane (67.0 mL) was added trifluoroacetic acid (27 mL) at ice temperature and the reaction mixture was stirred at room temperature over a period of 1 h. The product 6 (6.96 g) obtained upon evaporation of volatiles was used to next step without additional purification. $^1$H NMR (300 MHz, DMSO-d6) δ (ppm): 2.24 (s, 3H), 2.61 (t, J=6.1 Hz, 2H), 3.10-3.30 (m, 4H), 6.36 (s, 1H), 6.90-6.95 (m, 3H), 7.02-7.05 (m, 1H), 7.35 (t, J=7.8 Hz, 1H), 7.66-7.70 (m, 1H), 7.98 (d, J=2.4 Hz, 1H), 8.70 (bs, 2H). MS: (M+H) 281.3.

Step 6—To a solution of amine 6 (3.0 g, 7.0 mmol) in dimethyl sulfoxide (30 mL) was added diisopropylethylamine (4.2 mL, 22.0 mmol) and the product of Step 5, Example 1 (1.93 g, 7.0 mmol) at 25° C. The reaction mixture was allowed to stir at 60° C. over a period of 5 h. The resulting reaction mixture was diluted with ethyl acetate (500 mL), washed with water (3×150 mL) and dried over sodium sulphate. The crude product obtained upon evaporation of volatiles was purified through silica gel (230-400) column (50% ethyl acetate in petroleum ether) to give product 7 as an off-white solid 2.33 g (70%). mp: 87.8° C.-91.0° C. IR: 3250, 2895, 1624, 1425, 1263, 848, 774 cm$^{-1}$. $^1$H NMR (300 MHz, DMSO-d6) δ (ppm): 1.05-1.18 (m, 2H), 1.80-1.95 (m, 1H), 2.23-2.33 (m, 5H), 2.40 (t, J=5.1 Hz, 2H), 2.71 (m, 1H), 3.31 (t, J=5.5 Hz, 2H), 3.38 (t, J=5.5 Hz, 2H), 6.37 (s, 1H), 6.86-6.97 (m, 4H), 7.04-7.22 (m, 3H), 7.23-7.33 (m, 3H), 7.40 (td, J=7.9, 2.0 Hz, 1H), 7.70 (dt, J=8.3, 2.5 Hz, 1H), 7.99 (bs, 1H). MS: (M+H) 440.5.

Example 20—Synthesis of 4-[3-(pyridin-2-yloxy)-benzylidene]-piperidine-1-carboxylic acid [2-(4-methyl)phenyl-cyclopropyl]-amide

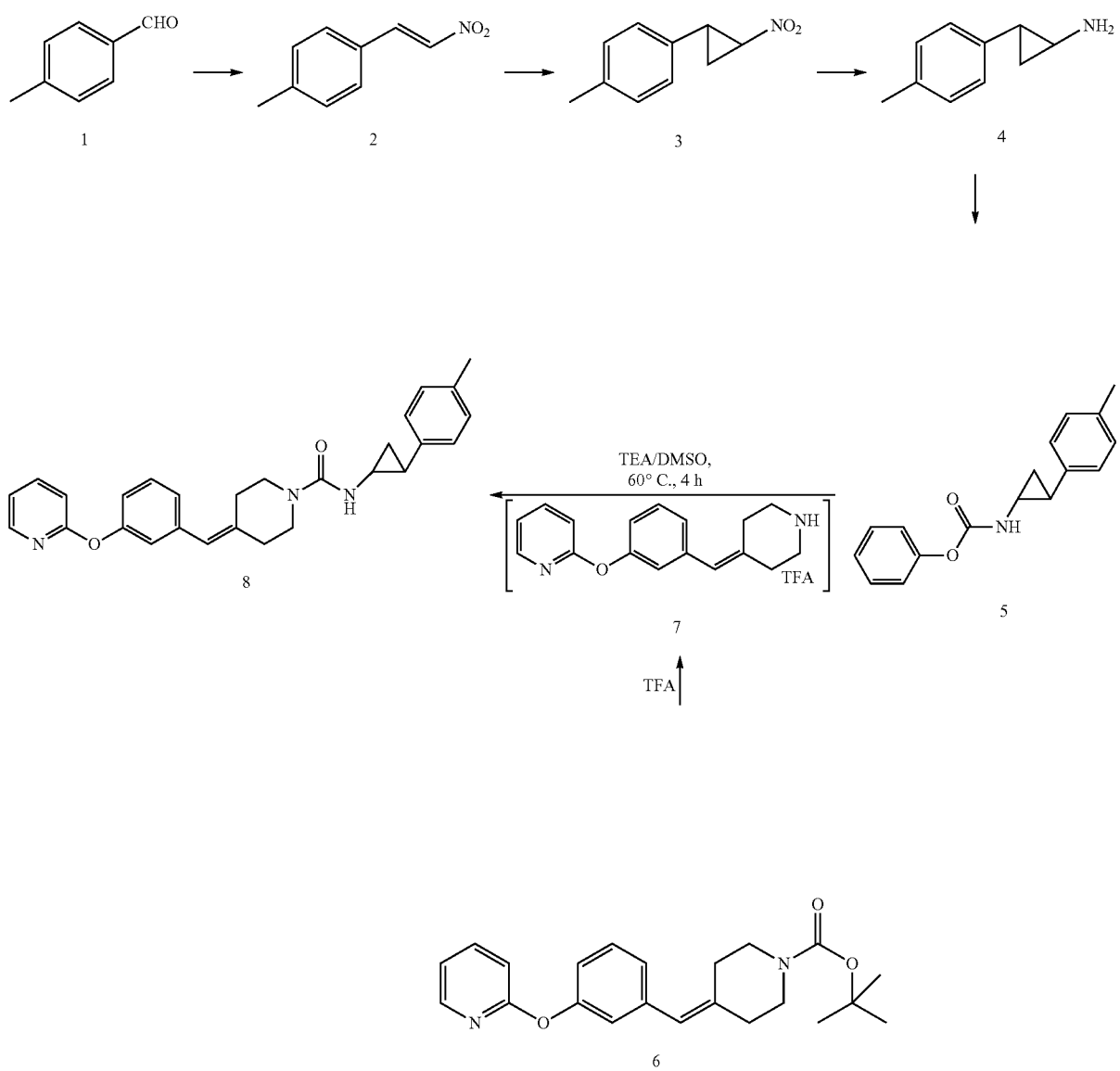

Step 1—Ammonium acetate (13.4 g, 0.17 mol) was added to acetic acid (100 mL) and stirred until fully dissolved. Then nitromethane (30.46 g, 0.49 mol) was added to reaction mixture followed by addition of 4-methyl-benzaldehyde (9.82 mL, 0.083 mol). The reaction mixture was refluxed at 100° C. for 6 h. The reaction mixture was allowed to stir at room temperature over a period of 16 h. The resulting reaction mixture was quenched with aq. 2M sodium hydroxide solution (pH=7) and extracted with ethyl acetate (2×300 mL), dried over sodium sulphate and concentrated under reduced pressure. The crude was washed with hexane to give product 2 as a yellow solid (10 g, 74%). $^1$H NMR (300 MHz, DMSO-d6) δ (ppm): 2.361 (s, 3H), 7.303 (d, 2H), 7.755 (d, 2H), 8.072-8.213 (m, 2H). MS (M−H) 162.9.

Step 2—To a solution of sodium hydride 60% dispersion in mineral oil (0.98 g, 0.024 mol) in dimethyl sulfoxide (10 mL) was added trimethyloxosulphonium iodide (6.7 g, 0.03 mol) and stirred for 30 min at room temperature. Then 2 (2 g, 0.012 mol) in dimethyl sulfoxide (10 mL) was added and reaction mixture stirred at room temperature over a period of 1 h. The resulting reaction mixture was quenched with water (100 mL), extracted with ethyl acetate (2×300 mL) and dried over sodium sulphate. The crude product obtained upon evaporation of volatiles was purified through silica gel (230-400 mesh) column (2% ethyl acetate in hexanes) to give product 3 as a pale yellow oil (300 mg, 14%). $^1$H NMR (300 MHz, DMSO-d6) δ (ppm): 1.653-1.704 (m, 1H), 2.203-2.273 (m, 1H), 2.353 (s, 3H), 3.112-3.157 (m, 1H), 4.370-4.417 (m, 1H), 7.015-7.042 (d, 2H), 7.14-7.166 (d, 2H). MS (M+H) 178.1.

Step 3—To a solution of 3 (0.3 g, 0.0016 mol) in isopropyl alcohol (12 mL) was added hydrochloric acid (6.2 mL of 2.7 N solution, 0.0169 mol) followed by zinc dust (1.1 g, 0.0169 mol) portion wise. Reaction mass allowed to stir at room temperature over a period of 16 h. The reaction mass was neutralized with 10% sodium hydroxide solution and filtered through celite bed. The filtrate was diluted with ethyl acetate (150 mL), washed with water (50 mL) and brine solution (50 mL), dried over sodium sulphate and concentrated under reduced pressure. The crude product obtained upon evaporation of volatiles was purified through silica gel (230-400 mesh) column (2% methanol in chloroform) to give product 4 as a yellow oil (150 mg, 60%). $^1$H NMR (300 MHz, DMSO-d6) δ (ppm): 0.879 (m, 2H), 1.667 (m, 1H), 2.229 (s, 3H), 2.293-2.331 (m, 1H), 7.018 (d, J=8.1, 2H), 6.879 (d, J=8.1, 2H). MS (M+H) 148.2.

Step 4—To a solution of 4 (90 mg, 0.0006 mol) in dichloromethane (2 mL) was added triethylamine (0.17 mL, 0.0012 mol) and phenyl chloroformate (115 mg, 0.0007 mol) at 0° C. Reaction mass was allowed to stir at room temperature over a period of 1 h. The resulting reaction mass was diluted with ethyl acetate (150 mL), washed with water (50 mL), dried over sodium sulphate and concentrated under reduced pressure. The crude product obtained upon evaporation of volatiles was purified through silica gel (230-400 mesh) column (10% ethyl acetate in hexanes) to give product 5 as a white solid (30 mg, 18%). $^1$H NMR (300 MHz, DMSO-d6) δ (ppm): 1.115-1.123 (m, 2H), 2.245 (s, 3H), 7.000-7.120 (m, 6H), 7.181-7.356 (m, 1H), 7.361-7.395 (m, 2H). MS (M+H) 268.3.

Step 5—To a solution of product of Step 4, Example 2 (1.0 g, 0.002 mol) in dichloromethane (10 mL) was added trifluoroacetic acid (4 mL) at 0° C. and the reaction mixture was allowed to stir at room temperature over a period of 1 h. The product 7 (1.3 g, 97%) obtained upon evaporation of volatiles was used for next step without additional purification.

Step 6—To a solution of 7 (0.29 g, 0.0006 mol) in dimethyl sulfoxide (3 mL) was added diisopropylethylamine (0.59 mL, 0.0034 mol) and 5 (0.16 g, 0.0006 mol) at room temperature. The reaction mass was allowed to stir at 60° C. over a period of 5 h. The resulting reaction mass was diluted with ethyl acetate (200 mL), washed with water (3×50 mL) and dried over sodium sulphate and concentrated under reduced pressure. The crude product obtained upon evaporation of volatiles was purified through silica gel (230-400 mesh) column (40% ethyl acetate in hexanes) to give product 8 as an off-white solid (180 mg, 69%). mp: 87.8-91.0° C. IR: 3250, 3013, 1624, 1573, 1425, 1263, 1117, 775 cm$^{-1}$. $^1$H NMR (300 MHz, DMSO-d6) δ (ppm): 1.001-1.046 (m, 1H), 1.085-1.133 (m, 1H), 1.836-1.845 (m, 1H), 2.249 (s, 5H), 2.382-2.44 (m, 2H), 2.643-2.665 (m, 1H), 3.29-3.326 (m, 2H), 3.365-3.401 (m, 2H), 6.360 (s, 1H), 6.952-7.082 (m, 8H), 7.117-7.157 (m, 1H), 7.348-7.401 (m, 1H), 7.830-7.888 (m, 1H), 8.156-8.166 (m, 1H). MS (M+H) 440.4.

Example 21—Synthesis of 4-[3-(pyrimidin-2-yloxy)-benzylidene]-piperidine-1-carboxylic acid [(1R, 2S)-2-phenyl-cyclopropyl]-amide

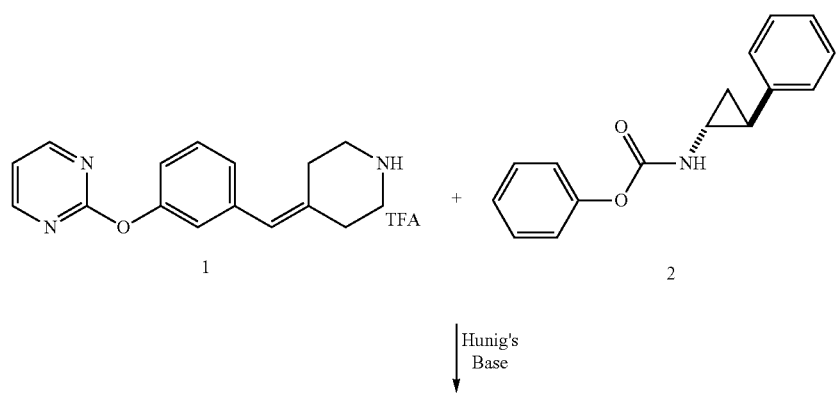

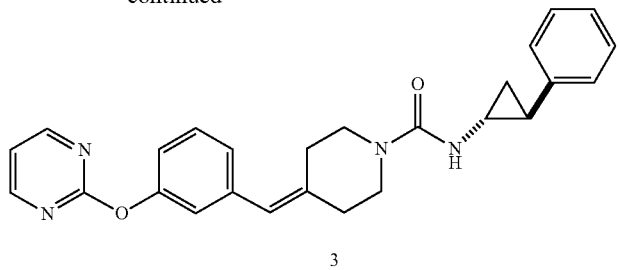

3

Step 1—To a solution of amine 1, the product of Step 5, Example 6 (3.02 g, 7.89 mmol) in dimethyl sulfoxide (30.0 mL) was added diisopropylethylamine (4.13 mL, 23.6 mmol) and 2, the product of Step 4, Example 16 (2.0 g, 7.89 mmol) at 25° C. The reaction mixture was allowed to stir at 60° C. over a period of 5 h. The resulting reaction mixture was diluted with ethyl acetate (300 mL), washed with water (3×150 mL) and dried over sodium sulphate. The crude product obtained upon evaporation of volatiles was purified through silica gel (230-400) column (60% ethyl acetate in petroleum ether) to give product 3 as a white solid 2.3 g (70%). mp: 62.8-65.2° C. IR: 3627, 3310, 1732, 1629, 1570, 1526, 1310, 1249, 1148, 753, 696 cm$^{-1}$. $^1$H NMR (400 MHz, DMSO-d6) δ (ppm): 1.04-1.18 (m, 2H), 1.85-1.88 (m, 1H), 2.27 (t, J=5.7 Hz, 2H), 2.39 (t, J=5.8 Hz, 2H), 2.71 (dt, J=7.4, 3.7 Hz, 1H), 3.31 (d, J=5.9 Hz, 2H), 3.39 (d, J=5.9 Hz, 2H), 6.37 (s, 1H), 6.84 (d, J=3.1 Hz, 1H), 7.03-7.12 (m, 6H), 7.20-7.30 (m, 3H), 7.39 (t, J=4.7 Hz, 1H), 8.64 (dd, J=4.7 Hz, 1.1 Hz, 2H). MS: 427.4 (M+H). HPLC purity: 99.79%. Chiral HPLC purity: 99.92%. Optical Rotation: −1.190. Specific Optical Rotation: −111.71.

Example 22—Synthesis of 4-[3-(5-methyl-pyridin-2-yloxy)-benzylidene]-piperidine-1-carboxylic acid ((1R,2S)-2-phenyl-cyclopropyl)-amide

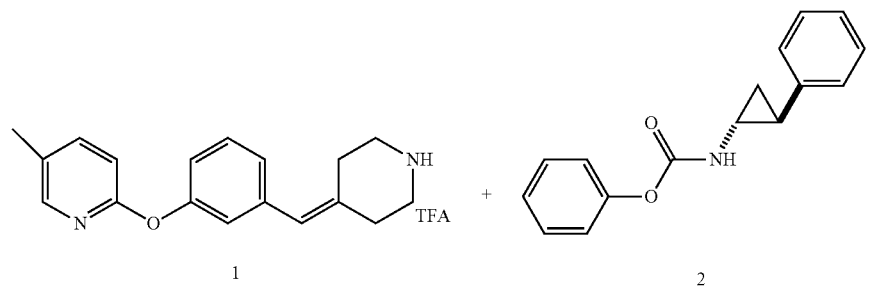

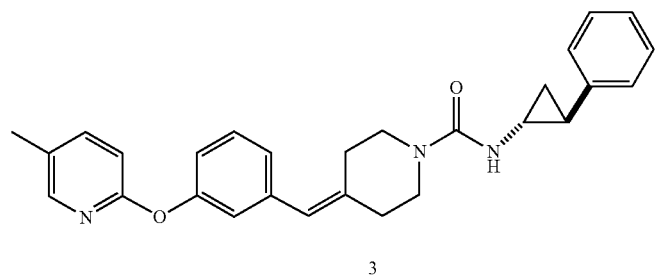

3

Step 1—To a solution of amine 1, the product of Step 5, Example 19 (3.0 g, 7.0 mmol) in dimethyl sulfoxide (30 mL) was added diisopropylethylamine (4.2 mL, 22.0 mmol) and the product of Step 4, Example 16 (1.93 g, 7.0 mmol) at 25° C. The reaction mixture was allowed to stir at 60° C. over a period of 5 h. The resulting reaction mixture was diluted with ethyl acetate (500 mL), washed with water (3×150 mL) and dried over sodium sulphate. The crude product obtained upon evaporation of volatiles was purified through silica gel (230-400) column (50% ethyl acetate in petroleum ether) to give product 3 as a pale yellow solid 2.7 g (81%). mp: 53.1-53.9° C. IR: 3321, 3024, 1628, 1526, 1475, 1249, 752, 695 cm$^{-1}$. $^1$H NMR (300 MHz, DMSO-d6) δ (ppm): 1.06-1.21 (m, 2H), 1.80-1.95 (m, 1H), 2.23-2.33 (m, 5H), 2.40 (t, J=5.6 Hz, 2H), 2.71 (m, 1H), 3.31 (t, J=5.5 Hz, 2H), 3.38 (t, J=5.5 Hz, 2H), 6.37 (s, 1H), 6.86-6.97 (m, 4H), 7.04-7.22 (m, 3H), 7.23-7.33 (m, 3H), 7.40 (td, J=7.9, 2.0 Hz, 1H), 7.70 (dt, J=8.3, 2.5 Hz, 1H), 7.99 (d, J=2.8 Hz, 1H). MS (M+H) 440.5. HPLC purity: 98.5%. Chiral HPLC purity: 100%.

Example 23—Synthesis of 4-[3-(pyrimidin-2-yloxy)-benzylidene]-piperidine-1-carboxylic acid methyl-((1R,2S)-2-phenyl-cyclopropyl)-amide

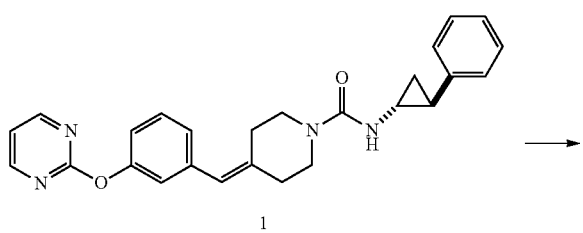

1

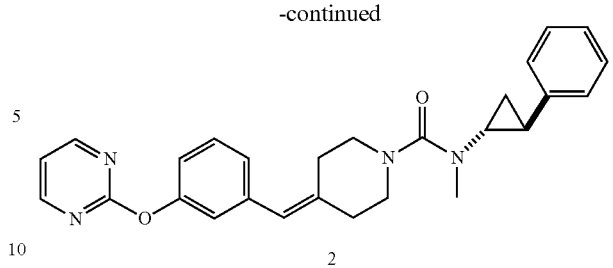

2

Step 1—To a solution of 1, product of Example 21 (150 mg, 7.89 mmol) in dimethylformamide (30.0 mL) were added sodium hydride (4.13 mL, 23.6 mmol) and methyl iodide (2.0 g, 7.89 mmol) at 0-5° C. The reaction mixture was allowed to stir at 25-30° C. over a period of 1 h. The resulting reaction mixture was diluted with water (50 mL), extracted with ethyl acetate (2×100 mL) and dried over sodium sulphate. The crude product obtained upon evaporation of volatiles was purified through silica gel (230-400) column (25% ethyl acetate in petroleum ether) to give 2 as a pale yellow solid 77 mg (50%). $^1$H NMR (300 MHz, DMSO-d6) δ (ppm): 1.24 (dt, J=7.8 Hz, 5.9 Hz, 2H), 2.02-2.07 (m, 1H), 2.27 (q, J=5.9 Hz, 2H), 2.38-2.41 (m, 2H), 2.79 (s, 4H), 3.12-3.33 (m, 4H), 6.34 (s, 1H), 6.97-7.21 (m, 6H), 7.20-7.31 (m, 3H), 7.39 (t, J=7.9 Hz, 1H), 8.65 (d, J=4.8 Hz, 2H). MS: 441.5 (M+H). HPLC purity: 98.1%.

Example 24—Synthesis of 4-[3-(5-methyl-pyrazin-2-yloxy)-benzylidene]-piperidine-1-carboxylic acid ((1R,2S)-2-phenyl-cyclopropyl)-amide

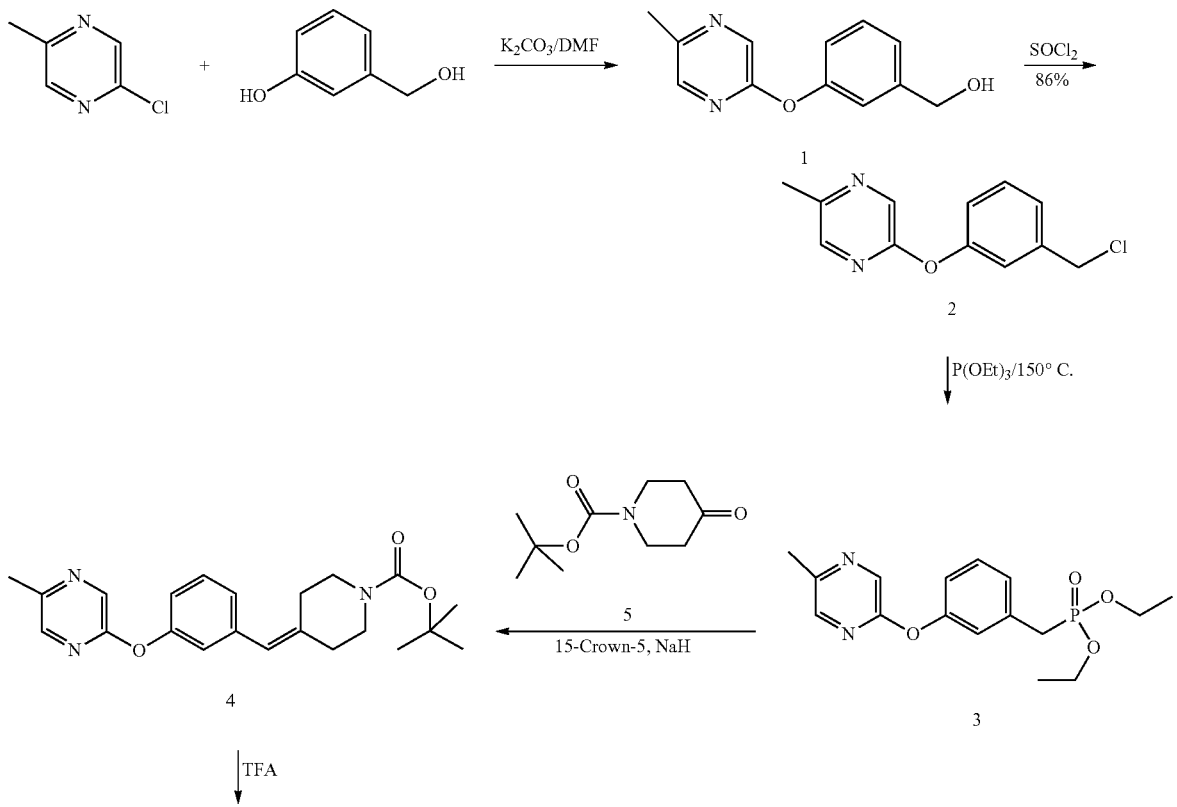

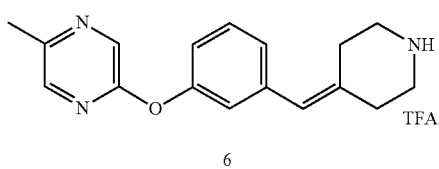

+

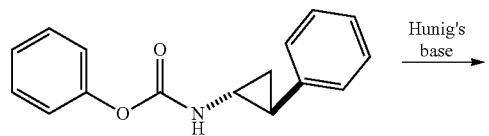

-continued

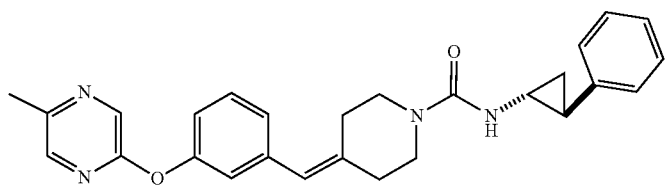

Step 1—To a solution of 2-chloro-5-methyl-pyrazine (10 g, 0.078 mol) in DMF (100 mL) was added 3-hydroxyphenyl-methanol (11.6 g, 0.094 mol) and cesium carbonate (76.0 g, 0.23 mol) at room temperature. The reaction mixture was stirred at 100° C. over a period of 5 h. Then the resulting mixture was allowed to reach room temperature, diluted with water (250 mL), extracted with ethyl acetate (3×500 mL) and the organic layer was dried over sodium sulphate. The crude product obtained upon evaporation of volatiles was purified through silica gel (230-400) column (30% ethyl acetate in petroleum ether) to give product 1 as a pale yellow oil 6.8 g (40%). $^1$H NMR (300 MHz, DMSO-d6) δ (ppm): 2.45 (s, 3H), 4.50 (d, J=4.5 Hz, 2H), 5.26 (t, J=5.26 Hz, 1H), 7.0-7.18 (m, 3H), 7.37 (t, J=7.5 Hz, 1H), 8.1 (s, 1H), 8.4 (d, J=1.2 Hz, 1H). MS (M+H) 217.2.

Step 2—To a solution of 1 (6.0 g, 0.027 mol) in dichloromethane (60 mL), thionyl chloride (2.3 mL, 0.03 mol) was added in a dropwise fashion while stirring reaction mixture in an ice bath. After removal of ice-bath, the reaction mixture was allowed to stir at room temperature over a period of 1 h. Then volatiles were evaporated under reduced pressure and diluted with toluene (25 mL) and toluene was evaporated under reduced pressure. This azeotropic process was repeated 3 times to obtain product 2 as a pale brown color oil (6.2 g). The crude product was used for next step without further purification. MS (M+H) 235.3.

Step 3—A solution of 2 (6.2 g, 0.026 mol) in triethyl phosphate (7.3 mL, 0.042 mol) was heated at 150° C. over a period of 6 h. The reaction mixture was cooled and allowed to reach room temperature and the crude product obtained upon evaporation of volatiles was purified through silica gel (230-400) column (60% ethyl acetate in petroleum ether) to give product 3 as a pale yellow oil 8.3 g. The product contained unused triethylphosphate and was used in next step without additional purification. $^1$H NMR (400 MHz, DMSO-d6) δ (ppm): 1.16 (t, J=7.0 Hz, 6H), 2.45 (s, 3H), 3.23 (s, 1H), 3.23 (s, 1H), 3.94 (dq, J=8.2 Hz, 7.0 Hz, 4H), 7.0-7.12 (m, 2H), 7.13-7.15 (m, 1H), 7.36 (t, J=7.8 Hz, 1H), 8.09 (dd, J=1.4 Hz, 0.7 Hz, 1H), 8.39 (d, J=1.4 Hz, 1H). MS (M+H) 337.1.

Step 4—To a solution of 3 (8.3 g, 0.024 mol) in THF (40 mL) was added 15-crown ether (0.1 g, 0.48 mmol). The reaction was cooled (ice bath) and NaH (1.44 g, 0.036 mol) was added portion wise. The reaction mixture was allowed to stir at room temperature for 30 min and again cooled to ice temperature. To the above reaction mixture, a solution of 4-oxo-piperidine-1-carboxylic acid tert-butyl ester 5 (4.9 g, 0.024 mol) in THF (40 mL) was added at ice temperature and allowed to stir at room temperature over a period 16 h. The resulting reaction mixture was diluted with water (250 mL), extracted with ethyl acetate (3×500 mL) and dried over sodium sulphate. The crude product obtained upon evaporation of volatiles to give product 4 as a pale yellow color oil (6.7 g). MS (M+H) 382.3. The product 4 was used in next step without further purification.

Step 5—To a solution of 4 (6.7 g, 0.017 mol) in dichloromethane (67.0 mL) was added trifluoroacetic acid (27 mL, 4V) at ice-cold temperature and the reaction mixture was stirred at room temperature over a period of 1 h. The product 6 (6.96 g, 90%) obtained upon evaporation of volatiles was used to next step without additional purification. $^1$H NMR (400 MHz, DMSO-d6) δ (ppm): 2.45 (s, 3H), 2.60-2.67 (m, 4H), 3.10-3.17 (m, 4H), 6.46 (s, 1H), 7.04-7.12 (m, 4H), 7.38 (t, J=7.8 Hz, 1H), 8.09 (s, 1H), 8.40 (d, J=4.4 Hz, 1H), 8.61 (bs, 2H). MS (M+H) 282.3.

Step 6—To a solution of amine 6 (1.0 g, 2.5 mmol) in dimethyl sulfoxide (30 mL) was added diisopropylethylamine (1.4 mL, 7.5 mmol) and the carbamate product of Step 4, Example 16 (0.7 g, 2.75 mmol) at 25° C. The reaction mixture was allowed to stir at 60° C. over a period of 5 h. The resulting reaction mixture was diluted with ethyl acetate (500 mL), washed with water (3×150 mL) and dried over sodium sulphate. The crude product obtained upon evaporation of volatiles was purified through silica gel (230-400) column (60% ethyl acetate in petroleum ether) to give product 7 as a pale yellow solid 0.7 g (68%). mp: 50.8° C. IR: 3305, 2923, 1627, 1528, 1473, 1337, 1266, 695 cm$^{-1}$. $^1$H NMR (300 MHz, DMSO-d6) δ (ppm): 1.02-1.20 (m, 2H), 1.82-1.84 (m, 1H), 2.21-2.41 (m, 4H), 2.46 (s, 3H), 2.60-2.70 (m, 1H), 3.26-3.34 (m, 4H), 6.32 (s, 1H), 6.80-7.22 (m, 9H), 7.35 (t, J=7.6, 1H), 8.06 (bs, 1H), 8.37 (bs, J=8.3, 1H). MS: 441.4 (M+H). HPLC: 99.91%.

Example 25—Synthesis of 4-[3-(5-chloro-pyridin-2-yloxy)-benzylidene]-piperidine-1-carboxylic acid ((1R,2S)-2-phenyl-cyclopropyl)-amide

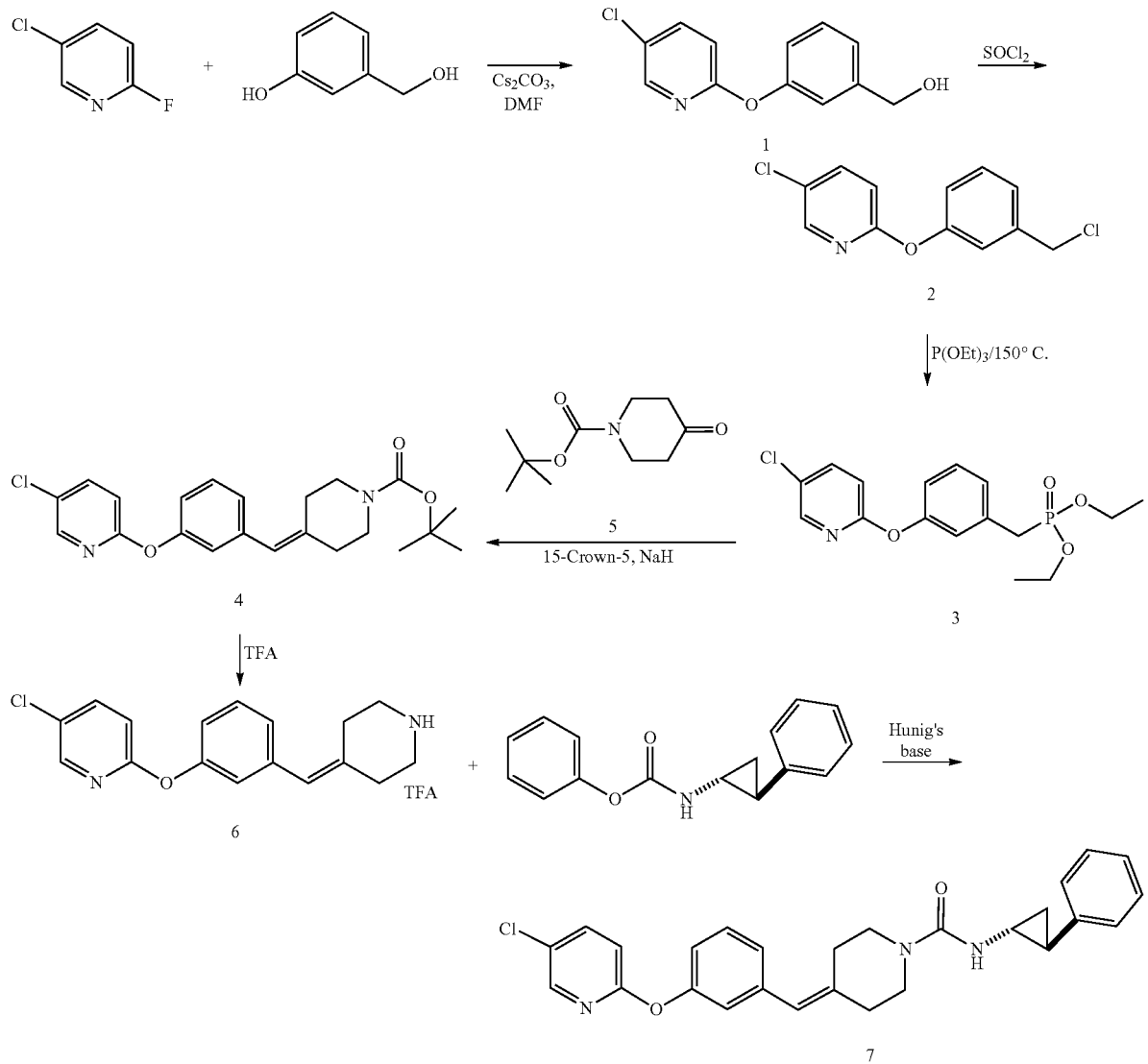

Step 1—To a solution of 5-chloro-2-fluoropyridine (10.0 g, 0.0760 mol) in DMSO (100 mL) were added 3-hydroxy-phenyl-methanol (9.42 g, 0.0760 mol) and cesium carbonate (29.72 g, 0.0912 mol) at room temperature. The reaction mixture was stirred at 100° C. over a period of 6 h. Reaction was monitored by TLC. The resulting mixture was cooled to room temperature, diluted with water (200 mL), extracted with ethyl acetate (2×400 mL) and the organic layer was dried over sodium sulphate. The crude product obtained upon evaporation of volatiles was purified through silica gel (230-400) column (12% ethyl acetate in petroleum ether) to give product 1 as a pale-yellow oil 12.0 g (67%). $^1$H NMR (400 MHz, DMSO-$d_6$) δ(ppm): 8.17 (t, J=2.4 Hz, 1H), 7.94-7.91 (m, 1H), 7.33 (t, J=8.0 Hz, 1H), 7.14-7.1 (m, 1H), 7.06-7.03 (m, 2H), 6.98-6.95 (m, 1H), 5.22 (t, J=5.6 Hz, 1H), 4.48 (d, J=5.6 Hz, 2H). MS m/z (M+H): 236.0

Step 2: To a solution of 1 (12.0 g, 0.0509 mol) in dichloromethane (120 mL) was added thionyl chloride (4.1 mL, 0.0560 mol) in a dropwise fashion while stirring reaction in an ice bath. After removal of ice-bath, the reaction mixture was allowed to stir at room temperature over a period of 1 h. After complete consumption of starting material, the volatiles were evaporated under reduced pressure, diluted with ethyl acetate (250 mL) and organic layer was washed with saturated sodium bicarbonate solution and water. Organic layer was dried over anhydrous sodium sulphate and concentrated. The crude product 2 obtained upon evaporation was directly taken to next step without further purification (12.5 g, 96%). $^1$H NMR (400 MHz, DMSO-$d_6$) δ(ppm): 8.20 (d, J=2.4 Hz, 1H), 8.19-7.95 (m, 1H), 7.42 (t, J=7.6 Hz, 1H), 7.29 (d, J=8.0 Hz, 1H), 7.21 (t, J=2.0 Hz, 1H), 7.12-7.09 (m, 2H), 4.75 (s, 1H). MS m/z (M+H): 254.1

Step 3: A solution of 2 (12.5 g, 0.0494 mol) in triethyl phosphate (20.0 mL, 0.1235 mol) was heated at 150° C. over a period of 6 h. The reaction mixture was allowed to reach room temperature and the crude product obtained after removal of the volatiles was added to n-heptane (150 mL) to yield a light orange color precipitate. The precipitate obtained was filtered and dried under vacuum to give product 3 as an off-white solid (16.5 g, 91%) and was used in the next step without further purification. $^1$H NMR (400 MHz, DMSO-d$_6$) δ(ppm): 8.19-8.18 (m, 1H), 7.97-7.94 (m, 1H), 7.34 (t, J=7.6 Hz, 1H), 7.13-7.06 (m, 1H), 7.03-6.99 (m, 3H), 3.95 (m, 4H), 3.27 and 3.21 (2s, 2H), 1.15 (t, J=4.4 Hz, 6H). MS m/z (M+H): 356.2

Step 4: To a solution of 3 (15.5 g, 0.0435 mol) in THF (100 mL) was added 15-crown ether (0.19 g, 0.87 mmol). The reaction was cooled (ice bath) and NaH (2.07 g, 0.0870 mol) added portion wise over a period of 5 min. The reaction mixture was allowed to stir at room temperature for 30 minutes and again cooled to ice temperature. A solution of 4-oxo-piperidine-1-carboxylic acid tert-butyl ester 5 (8.66 g, 0.0435 mol) in THF (50 mL) was added at ice temperature and allowed to stir at room temperature over a period 16 h. The resulting reaction mixture was quenched with water and extracted with ethyl acetate. Organic layer was dried over anhydrous sodium sulphate and concentrated. The crude product obtained after evaporation of the volatiles were purified by silica-gel column chromatography to obtain the product 4 as a light yellow liquid (13.1 g, 75%). $^1$H NMR (400 MHz, DMSO-d$_6$) δ (ppm): 8.19 (d, J=2.0 Hz, 1H), 7.96-7.93 (m, 1H), 7.36 (t, J=7.6 Hz, 1H), 7.09-7.06 (m, 2H), 6.99-6.96 (m, 2H), 6.35 (s, 1H), 3.40-3.32 (m, 4H), 2.38 (t, J=5.2 Hz, 2H), 2.26 (t, J=6.0 Hz, 2H), 1.39 (s, 9H). MS m/z (M+Na): 423.2

Step 5: To a solution of 4 (13.0 g, 0.0325 mol) in dichloromethane (130 mL) was added trifluoroacetic acid (52.0 mL) at ice temperature and the reaction mixture was stirred at room temperature over a period of 2 h. Reaction was monitored by TLC. After complete consumption of the starting material, volatiles were removed under reduced pressure to get product as a pale brown oil. The crude product obtained was washed with ether (3×50 mL) to give 6 as a pale brown thick liquid (13.8 g crude). $^1$H NMR (400 MHz, DMSO-d6) δ (ppm): 8.82 (bs, 2H), 8.19 (d, J=2.8 Hz, 1H), 7.96-7.93 (m, 1H), 7.38 (t, J=8.0 Hz, 1H), 7.09 (d, J=8.8 Hz, 2H), 7.02-7.00 (m, 2H), 6.44 (s, 1H), 3.38-3.33 (m, 4H), 2.60 (t, J=5.6 Hz, 2H), 2.53-2.48 (m, 2H). MS m/z (M+H): 301.2

Step 6: To a solution of 6 (15.8 g, 0.0381 mol) in dimethyl sulfoxide (78 mL) was added diisopropyl-ethyl-amine (20.34 mL, 0.1149 mol) and the carbamate product of Step 4, Example 16 (10.62 g, 0.0419 mol) at 25° C. The reaction mixture was allowed to stir at 60° C. over a period of 6 h. The resulting reaction mixture was diluted with ethyl acetate (500 mL), washed with water (3×200 mL) and dried over sodium sulphate. The crude product obtained upon evaporation of volatiles was purified through silica gel (230-400) column (40% ethyl acetate in petroleum ether) to give product 7 as a light yellow fluffy solid (11.6 g, 66%). melting range (MR): 44.8-62.6° C. $^1$H NMR (400 MHz, DMSO-d6) δ (ppm): 8.18 (d, J=2.4 Hz, 1H), 7.94-7.91 (m, 1H), 7.35 (t, J=7.6 Hz, 1H), 7.23-7.19 (m, 2H), 7.12-7.05 (m, 5H), 6.95-6.82 (m, 2H), 6.32 (s, 1H), 3.37-3.26 (m, 4H), 2.71-2.69 (m, 1H), 2.36-2.33 (t, J=5.2 Hz, 2H), 2.24-2.22 (t, J=5.6 Hz, 2H), 1.85 (m, 1H), 1.13 (d, J=4.8 Hz, 1H), 1.04 (d, J=7.6 Hz, 1H). $^{13}$C NMR: (100 MHz, DMSO-d6): δ 161.69, 157.57, 153.49, 145.56, 141.99, 139.92, 139.75, 138.80, 129.56, 128.08, 125.85, 125.34, 125.21, 123.04, 121.29, 119.02, 113.05, 44.93, 43.89, 35.63, 34.07, 28.91, 24.32 and 15.58. MS m/z (M+H): 460.32, HPLC purity: 99.36%, Chiral purity: 99.71%.

Example 26—Synthesis of 4-[3-(5-fluoro-pyridin-2-yloxy)-benzylidene]-piperidine-1-carboxylic acid ((1R,2S)-2-phenyl-cyclopropyl)-amide

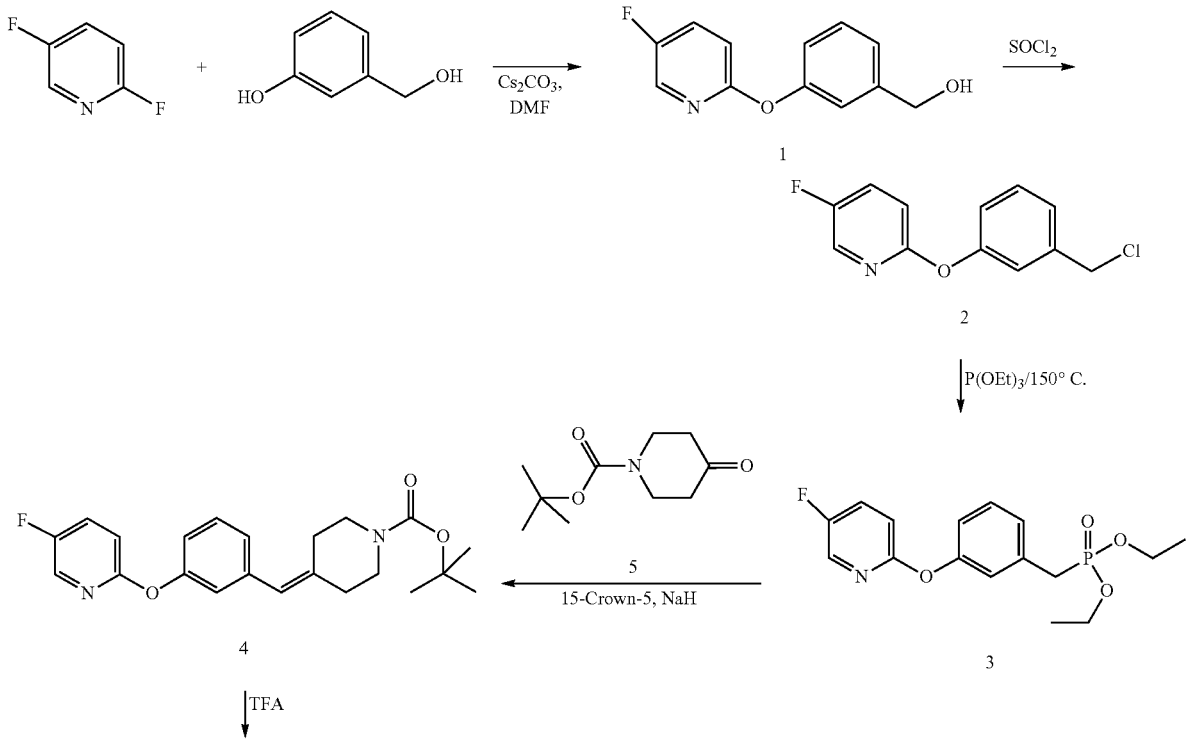

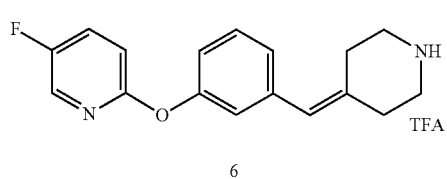 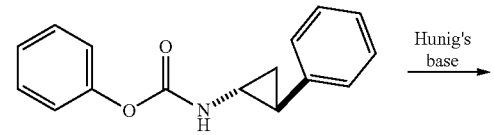

-continued

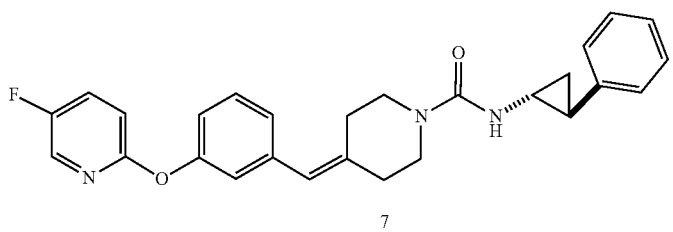

Step 1: To a solution of 2,5-difluoropyridine (8.2 g, 0.0719 mol) in DMSO (80 mL) were added 3-hydroxyphenyl-methanol (8.9 g, 0.0719 mol) and cesium carbonate (28.12 g, 0.0863 mol) at room temperature and the reaction mixture stirred at 85° C. over a period of 6 h. Reaction was monitored by TLC. The resulting mixture was cooled to reach room temperature, diluted with water (200 mL), extracted with ethyl acetate (3×400 mL) and the organic layer dried over sodium sulphate. The crude product obtained upon evaporation of volatiles was purified through silica gel (230-400) column (12% ethyl acetate in petroleum ether) to give product 1 as a pale yellow oil 4.3 g (28%). $^1$H NMR (400 MHz, DMSO-d$_6$) δ(ppm): 8.17 (t, J=2.4 Hz, 1H), 7.84-7.78 (m, 1H), 7.35 (t, J=10.4 Hz, 1H), 7.15-6.95 (m, 4H), 5.25 (t, J=7.6 Hz, 1H), 4.50 (d, J=7.6 Hz, 2H). MS m/z (M+H): 220.0

Step 2: To a solution of 1 (6.5 g, 0.0296 mol) in dichloromethane (65 mL) was added thionyl chloride (2.4 mL, 0.0326 mol) dropwise while stirring reaction in an ice bath. After removal of ice-bath, the reaction mixture was allowed to stir at room temperature over a period of 2 hours. After complete consumption of starting material, the volatiles were evaporated under reduced pressure, diluted with ethyl acetate (200 mL), and organic layer washed with saturated sodium bicarbonate solution and water. Organic layer was dried over anhydrous sodium sulphate and concentrated. The crude product 2 obtained upon evaporation was directly taken to next step without further purification (6.7 g, 95%). $^1$H NMR (400 MHz, DMSO-d$_6$) δ(ppm): 8.15 (d, J=2.4 Hz, 1H), 7.83-7.80 (m, 1H), 7.40 (t, J=7.6 Hz, 1H), 7.27-7.25 (m, 1H), 7.19-7.06 (m, 3H), 4.75 (s, 1H). MS m/z (M+H): 238.0

Step 3: A solution of 2 (6.5 g, 0.0274 mol) in triethyl phosphate (12.6 mL, 0.0685 mol) was heated at 150° C. over a period of 6 h. The reaction mixture was cooled to reach room temperature and the mixture obtained after evaporation of the volatiles was purified by silica-gel (230-400) column chromatography to obtain product 3 as a pale yellow liquid (9.0 g, 95%). $^1$H NMR (400 MHz, DMSO-d$_6$) δ(ppm): 8.15 (d, J=4.0 Hz, 1H), 7.86-7.80 (m, 1H), 7.34 (t, J=10.4 Hz, 1H), 7.12-6.97 (m, 4H), 4.02-3.89 (m, 4H), 3.28 and 3.21 (2s, 2H), 1.15 (t, J=9.2 Hz, 6H). MS m/z (M+H): 340.2

Step 4: To a solution of 3 (9.0 g, 0.0256 mol) in THF (60 mL) was added 15-crown ether (0.12 g, 0.53 mmol). The reaction was cooled (ice bath) and 60% NaH (1.26 g, 0.0530 mol) was added portion wise over a period of 5 min. The reaction mixture was allowed to stir at room temperature for 30 min and again cooled to ice temperature. A solution of 4-oxo-piperidine-1-carboxylic acid tert-butyl ester 5 (5.28 g, 0.0256 mol) in THF (30 mL) was added at ice temperature and allowed to stir at room temperature over a period 16 h. The resulting reaction mixture was quenched with water and extracted with ethyl acetate. Organic layer was dried over anhydrous sodium sulphate and concentrated. The crude product obtained after evaporation of the volatiles were purified by silica-gel column chromatography to get product 4 as a pale yellow solid (8.0 g, 78%). %). $^1$H NMR (400 MHz, DMSO-d$_6$) δ (ppm): 8.15 (d, J=3.2 Hz, 1H), 7.84-7.79 (m, 1H), 7.35 (t, J=8.0 Hz, 1H), 7.12-7.04 (m, 2H), 6.96-6.92 (m, 2H), 6.35 (s, 1H), 3.40-3.32 (m, 4H), 2.37 (t, J=5.6 Hz, 2H), 2.25 (t, J=5.2 Hz, 2H), 1.39 (s, 9H). MS m/z (M+Na): 407.2

Step 5: To a solution of 4 (8.2 g, 0.0213 mol) in dichloromethane (82 mL) was added trifluoroacetic acid (32.5 mL) at ice temperature and the reaction mixture was stirred at room temperature over a period of 1 h. Reaction was monitored by TLC. After complete consumption of starting material, volatiles were removed under reduced pressure to obtain product as a red oil. The crude product obtained was washed with ether (3×50 mL) to yield 6 as thick brown oil (9.0 g Crude). $^1$H NMR (300 MHz, DMSO-d6) δ (ppm): 8.73 (bs, 2H), 8.15 (d, J=3.2 Hz, 1H), 7.84-7.79 (m, 1H), 7.37 (t, J=8.0 Hz, 1H), 7.12-7.06 (m, 2H), 7.00-6.96 (m, 2H), 6.44 (s, 1H), 3.15-3.09 (m, 4H), 2.59 (t, J=6.0 Hz, 2H), 2.49-2.48 (m, 2H). MS m/z (M+H): 285.4

Step 6: To a solution of 6 (8.4 g, 0.021 mol) in dimethyl sulfoxide (42 mL) was added diisopropyl-ethyl-amine (11.1 mL, 0.063 mol) and the carbamate product of Step 4, Example 16 (5.8 g, 0.023 mol) at 25° C. The reaction mixture was allowed to stir at 60° C. over a period of 6 h. The resulting reaction mixture was diluted with ethyl acetate (400 mL), washed with water (3×100 mL) and dried over sodium sulphate. The crude product obtained upon evaporation of volatiles was purified through silica gel (230-400) column (40% ethyl acetate in petroleum ether) to give product 7 as a light yellow fluffy solid (7.15 g, 66%). $^1$H NMR (400 MHz, DMSO-d6) δ (ppm): 8.15 (d, J=2.4 Hz, 1H), 7.82-7.80 (m, 1H), 7.35 (t, J=8.0 Hz, 1H), 7.24-7.21 (m, 2H), 7.14-7.04 (m, 5H), 6.96-6.94 (m, 2H), 6.84 (d, J=2.8 Hz, 1H), 6.34 (s, 1H), 3.38-3.28 (m, 4H), 2.71-2.69 (m, 1H), 2.34 (t, J=5.2 Hz, 2H), 2.23 (t, J=4.8 Hz, 2H), 1.86 (m, 1H), 1.13 (d, J=4.8 Hz, 1H), 1.04 (d, J=7.6 Hz, 1H). $^{13}$C NMR: (100 MHz, DMSO-d6): δ 159.15, 157.57, 156.01 (d, J=244.7 Hz), 154.08, 141.99, 139.69, 138.76, 134.13 (d, J=26.3 Hz), 129.54, 128.09, 127.85 (d, J=20.9 Hz), 125.86, 125.35, 124.91, 123.09, 120.97, 118.71, 113.01, 44.94, 43.90, 35.63, 34.07, 28.91, 24.32 and 15.58. MS m/z (M+H): 444.3, HPLC purity: 99.21%, Chiral HPLC: 99.37%.

Example 27: Synthesis of 6-{3-[1-((1R,2S)-2-phenyl-cyclopropylcarbamoyl)-piperidin-4-ylidenemethyl]-phenoxy}-nicotinic acid methyl ester

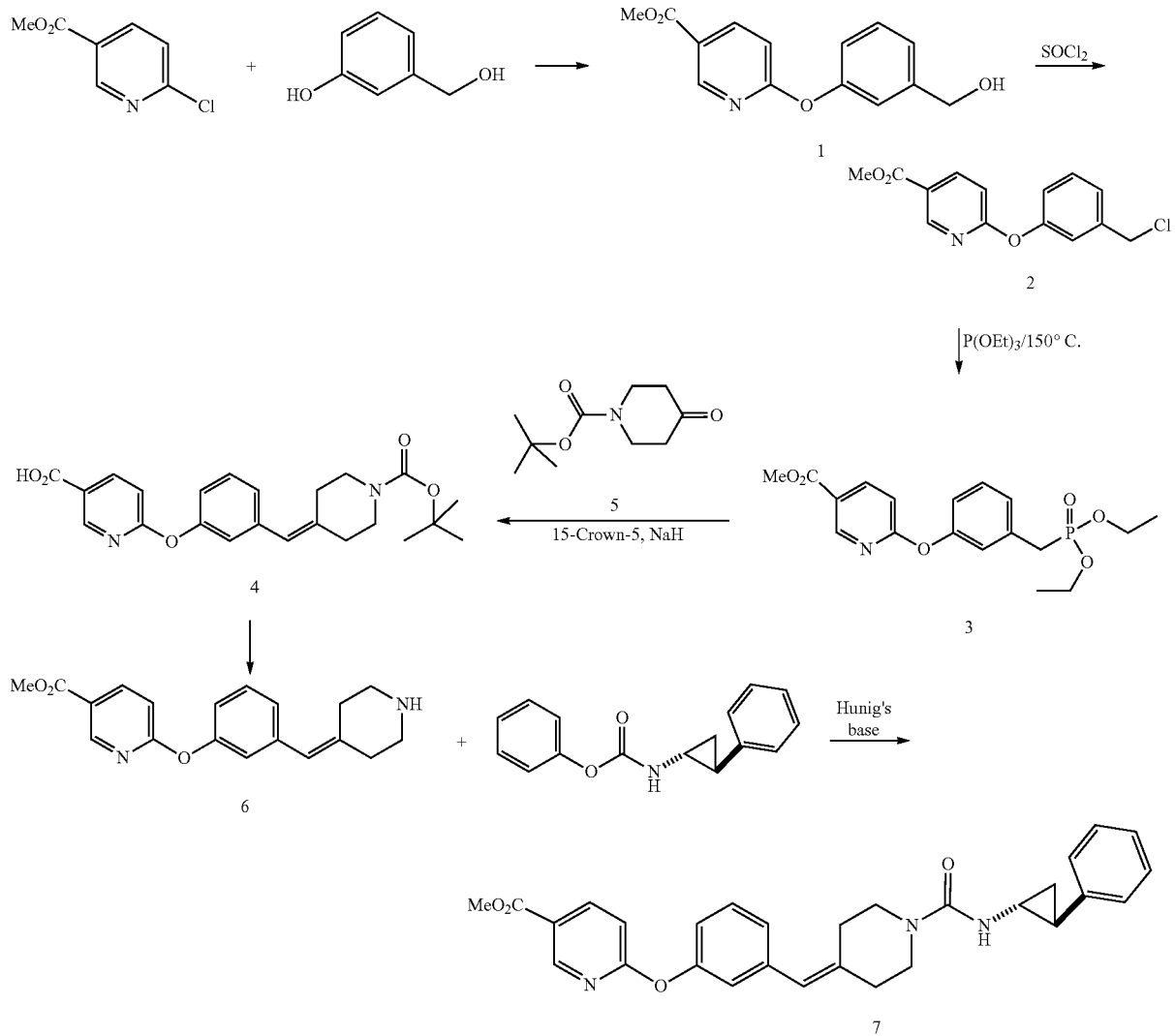

Step 1: To a solution of methyl 6-chloropyridine-3-carboxylate (50.0 g, 0.29 mol) in dimethyl-acetamide (500 mL) were added 3-hydroxyphenyl-methanol (39.79 g, 0.32 mol) and potassium carbonate (60.4 g, 0.43 mol) at room temperature. The reaction mixture was stirred at 100° C. over a period of 6 h. Reaction was monitored by TLC. The resulting mixture was cooled to room temperature, diluted with water (300 mL), extracted with ethyl acetate (2×500 mL) and the organic layer dried over sodium sulphate. The crude product obtained upon evaporation of volatiles was purified through silica gel (230-400) column (12% ethyl acetate in petroleum ether) to give product 1 as a pale yellow oil (30.0 g, 40%). $^1$H NMR (400 MHz, DMSO-d$_6$) δ(ppm): 8.82 (d, J=2.0 Hz, 1H), 8.30-8.27 (m, 1H), 7.42 (t, J=8.0 Hz, 1H), 7.27-7.19 (m, 2H), 7.09-7.07 (m, 1H), 6.96 (d, J=8.8 Hz, 1H), 4.73 (s, 2H), 3.93 (d, J=3.6 Hz, 3H). MS m/z (M+H): 259.8

Step 2: To a solution of 1 (30.0 g, 0.115 mol) in dichloromethane (300 mL) was added thionyl chloride (9.4 mL, 0.127 mol) dropwise while stirring reaction in an ice bath. After removal of ice-bath, the reaction mixture was allowed to stir at room temperature over a period of 2 hours. After complete consumption of starting material, the volatiles were evaporated under reduced pressure, diluted with ethyl acetate (500 mL), organic layer was washed with saturated sodium bicarbonate (200 mL) solution and water. Organic layer was dried over anhydrous sodium sulphate and concentrated. The crude product obtained upon evaporation was purified by silica gel (230-400) column chromatography to obtain product 2 as a pale yellow liquid (28.0 g, 87%). $^1$H NMR (400 MHz, DMSO-$d_6$) δ(ppm): 8.82 (d, J=0.8 Hz, 1H), 8.31-8.28 (m, 1H), 7.43 (t, J=8.0 Hz, 1H), 7.29-7.27 (m, 1H), 7.21 (t, J=2.0 Hz, 1H), 7.14-7.11 (m, 1H), 6.98-6.96 (m, 1H), 4.61 (s, 2H), 3.93 (s, 3H). MS m/z (M+H): 278.0

Step 3: A solution of 2 (28.0 g, 0.10 mol) in triethyl phosphate (41.0 mL, 0.25 mol) was heated at 150° C. over a period of 6 h. The reaction mixture was cooled to reach room temperature and the mixture obtained after evaporation of the volatiles was purified by silica-gel column chromatography to get 3 as a pale yellow liquid (32.0 g, 84%). $^1$H NMR (400 MHz, DMSO-$d_6$) δ(ppm): 8.65-8.64 (m, 1H), 8.30-8.27 (m, 1H), 7.35 (t, J=8.0 Hz, 1H), 7.16-7.03 (m, 4H), 3.96-3.88 (m, 4H), 3.82 (s, 3H), 3.27 and 3.21 (2s, 2H), 1.15-1.11 (m, 6H). MS m/z (M+H): 380.2

Step 4: To a solution of 3 (35.5 g, 0.093 mol) in THF (200 mL) was added 15-crown ether (0.41 g, 1.8 mmol). The reaction was cooled (ice bath) and 60% NaH (5.5 g, 0.14 mol) added portion wise over a period of 5 minutes. The reaction mixture was allowed to stir at room temperature for 30 min and again cooled to ice temperature. A solution of 4-oxo-piperidine-1-carboxylic acid tert-butyl ester 5 (18.7 g, 0.093 mol) in THF (150 mL) was added at ice temperature and allowed to stir at room temperature over a period 16 h. The resulting reaction mixture was quenched with saturated ammonium chloride and extracted with ethyl acetate. Organic layer was dried over anhydrous sodium sulphate and concentrated. The crude product (30.0 g) obtained after evaporation of the volatiles was dissolved in methanol (300 mL) and aqueous lithium hydroxide solution (3.0 g, 0.0707 mol) was added at ice temperature. Resulting reaction mass was stirred at 50° C. for 2 hours. Reaction was monitored by TLC. The crude product obtained after evaporation of the volatiles was dissolved in water (200 mL) and washed with methyl tert-butyl ether (2×200 mL). Aqueous layer was acidified to pH 2.0 using 1.0 N aqueous HCl solution. The product precipitated was filtered and dried to get 4 as an off-white solid (23.0 g, 61%). $^1$H NMR (400 MHz, DMSO-$d_6$) δ(ppm): 13.19 (bs, 1H), 8.66-8.65 (m, 1H), 8.28-8.25 (m, 1H), 7.39 (t, J=8.0 Hz, 1H), 7.11-7.00 (m, 4H), 6.37 (s, 1H), 3.40-3.32 (m, 4H), 2.39 (t, J=5.6 Hz, 2H), 2.27 (t, J=5.2 Hz, 2H), 1.39 (s, 9H). MS m/z (M+H): 433.2

Step 5: To a solution of 4 (13.0 g, 0.0317 mol) in methanol (130 mL) was added trimethyl sillyl chloride (8.9 mL, 0.0697 mol) at ice temperature and the reaction mixture was stirred at room temperature over a period of 12 h and monitored by TLC. After complete consumption of starting material, volatiles were removed under reduced pressure. The crude product obtained was diluted with saturated sodium bicarbonate solution and extracted with ethyl acetate. Organic layer was washed with water, dried over anhydrous sodium sulphate, filtered and concentrated. The crude product obtained after evaporation of the volatiles were purified by silica-gel (230-400) column chromatography to obtain the product 6 as a pale yellow liquid (5.2 g, 51%). $^1$H NMR (400 MHz, DMSO-$d_6$) δ(ppm): 8.68-8.67 (m, 1H), 8.31-8.28 (m, 1H), 7.39-7.36 (m, 1H), 7.13-6.97 (m, 4H), 6.24 (s, 1H), 3.84 (s, 3H), 2.78-2.65 (m, 4H), 2.34 (t, J=5.2 Hz, 2H), 2.21 (t, J=5.2 Hz, 2H). MS m/z (M+H): 325.3

Step 6: To a solution of 6 (5.2 g, 0.016 mol) in dimethyl sulfoxide (52 mL, 10V) was added diisopropyl ethyl amine (8.9 mL, 0.048 mol) and the carbamate product of Step 4, Example 16 (4.0 g, 0.016 mol) at 25° C. The reaction mixture was allowed to stir at 60° C. over a period of 6 h. Reaction was monitored by TLC. The resulting reaction mixture was diluted with ethyl acetate (300 mL), washed with water (3×100 mL) and dried over anhydrous sodium sulphate. The crude product obtained upon evaporation of volatiles was purified through silica gel (230-400) column (40% ethyl acetate in petroleum ether) to give product 7 as a light yellow fluffy solid (5.0 g, 65%). melting point range (MR): 52.6-72.8° C. $^1$H NMR (400 MHz, DMSO-d6) δ (ppm): 8.68 (d, J=2.0 Hz, 1H), 8.31-8.28 (m, 1H), 7.38 (t, J=8.0 Hz, 1H), 7.24-7.20 (m, 2H), 7.13-7.01 (m, 7H), 6.84-6.83 (m, 1H), 6.35 (s, 1H), 3.84 (s, 3H), 3.38-3.30 (m, 4H), 2.71-2.69 (m, 1H), 2.37 (t, J=5.2 Hz, 2H), 2.25 (t, J=5.2 Hz, 2H), 1.86 (m, 1H), 1.15 (d, J=4.8 Hz, 1H), 1.05 (d, J=6.0 Hz, 1H). $^{13}$C NMR: (100 MHz, DMSO-d6): δ 165.87, 164.78, 157.57, 152.92, 149.45, 141.99, 140.87, 139.87, 138.88, 129.66, 128.08, 125.85, 125.67, 125.34, 122.97, 121.66, 120.97, 119.39, 111.21, 52.23, 44.92, 43.88, 35.63, 34.07, 28.90, 24.31 and 15.57. MS m/z (M+H): 484.3, HPLC purity: 98.65%, Chiral HPLC: 99.08%

Example 28: Synthesis of 6-{3-[1-((1R,2S)-2-phenyl-cyclopropylcarbamoyl)-piperidin-4-ylidenemethyl]-phenoxy}-nicotinic acid

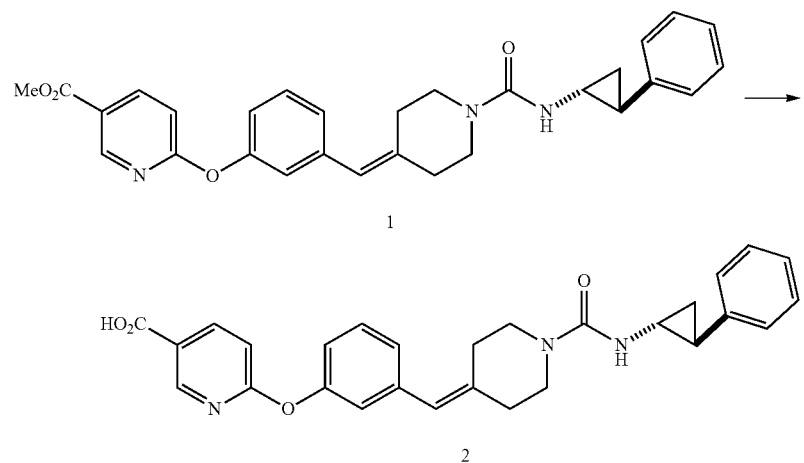

To a solution of 1, product of Example 27 (1.8 g, 0.0038 mol) in methanol (18 mL) was added aqueous lithium hydroxide (0.32 g, 0.0076 mol) dropwise at ice temperature. The reaction mixture was allowed to stir at room temperature over a period of 3 h. Reaction was monitored by TLC. The crude product obtained after evaporation of the volatiles were diluted with water (10 mL) and the aqueous layer washed with methyl tert-butyl ether. The resulting aqueous layer was acidified with 1.5 N HCl to pH 2. The product precipitated, was filtered and dried to give 2 as an off-white solid 1.52 g (87%). Melting range (MR) 141-159° C. $^1$H NMR (400 MHz, DMSO-d6) δ (ppm): 13.19 (bs, 1H), 8.66-8.65 (m, 1H), 8.28-8.26 (m, 1H), 7.38 (t, J=8.0 Hz, 1H), 7.24-7.21 (m, 2H), 7.13-7.01 (m, 7H), 6.83 (d, J=3.2 Hz, 1H), 6.35 (s, 1H), 3.38-3.28 (m, 4H), 2.71-2.69 (m, 1H), 2.37 (t, J=5.2 Hz, 2H), 2.25 (t, J=5.2 Hz, 2H), 1.86 (m, 1H), 1.15 (d, J=4.4 Hz, 1H), 1.05 (d, J=7.6 Hz, 1H). $^{13}$C NMR: (100 MHz, DMSO-d6): δ 165.84, 165.69, 157.57, 153.03, 149.57, 142.0, 141.05, 139.84, 138.86, 129.64, 128.09, 125.85, 125.59, 125.34, 123.0, 122.02, 121.66, 119.40, 111.06, 44.92, 43.89, 35.64, 34.08, 28.91, 24.30 and 15.57. MS m/z (M+H): 470.3, HPLC purity: 99.88%, Chiral HPLC: 99.50%, Example 29: Synthesis of 4-[3-(5-hydroxymethyl-pyridin-2-yloxy)-benzylidene]-piperidine-1-carboxylic acid ((1R,2S)-2-phenyl-cyclopropyl)-amide

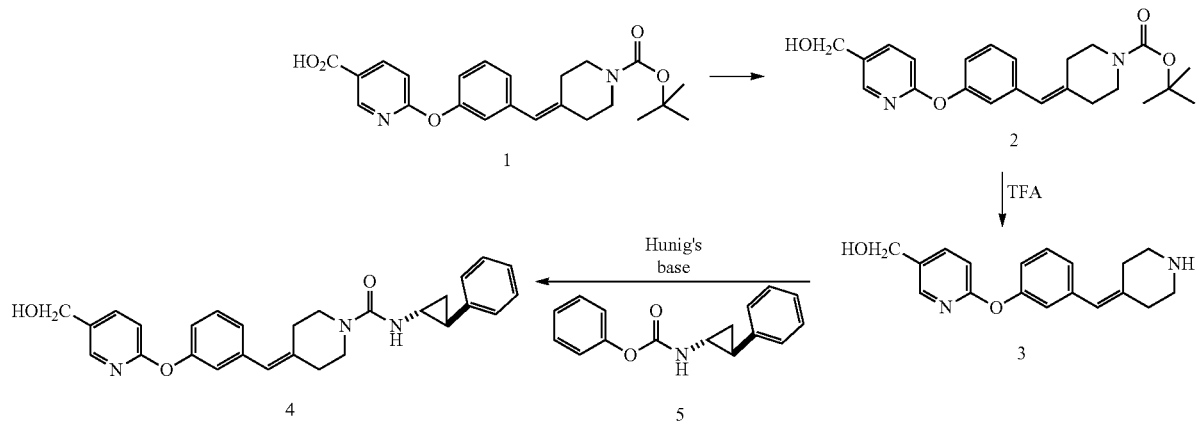

Step 1: To a solution of 1, product of step 4 Example 27 (3.6 g, 0.0085 mol) in dimethoxyethane (35 mL) was added N-methyl morpholine (1.4 mL, 0.0128 mol) and isobutyl chloroformate (1.21 mL, 0.0093 mol) at ice temperature and the reaction mixture was stirred at room temperature over a period of 30 minutes. Sodium borohydride (1.9 g, 0.0512 mol) was added portion wise to the reaction mass and stirred for 12 hours. Reaction was monitored by TLC. After complete consumption of the starting material 1, reaction mass was quenched with water (100 mL) and extracted with ethyl acetate (300 mL). Organic layer was dried over anhydrous sodium sulphate and concentrated. The crude product obtained was purified by silica-gel (230-400) column chromatography to obtain the product 2 as an off-white solid (3.2 g, 92%). $^1$H NMR (400 MHz, DMSO-d$_6$) δ(ppm): 8.06 (m, 1H), 7.79-7.76 (m, 1H), 7.34 (t, J=8.0 Hz, 1H), 7.05-6.95 (m, 4H), 6.35 (s, 1H), 5.24 (t, J=6.0 Hz, 1H), 4.45 (d, J=5.6 Hz, 1H), 3.40-3.32 (m, 4H), 2.38 (t, J=5.6 Hz, 2H), 2.25 (t, J=5.2 Hz, 2H), 1.39 (s, 9H). MS m/z (M+H): 397.3

Step 2: To a solution of 2 (3.2 g, 0.08 mol) in dichloromethane (32 mL) was added trifluoroacetic acid (12.8 mL) at ice temperature and the reaction mixture was stirred at room temperature over a period of 1 h. Reaction was monitored by TLC. After complete consumption of starting material, volatiles were removed under reduced pressure to obtain crude product as brown red oil. The crude product obtained was washed with ether (3×50 mL) to yield 3 as an off-white solid (3.3 g crude). MS m/z (M+H): 297.17

Step 3: To a solution of 3 (3.3 g, 0.08 mmol) in dimethyl sulfoxide (30 mL) was added diisopropyl ethyl amine (4.2 mL, 0.024 mol) and the carbamate product of Step 4, Example 16 (2.0 g, 0.08 mmol) at 25° C. The reaction mixture was allowed to stir at 60° C. over a period of 6 h. The resulting reaction mixture was diluted with ethyl acetate (300 mL), washed with water (3×100 mL) and dried over sodium sulphate. The crude product obtained upon evaporation of volatiles was purified through silica gel (230-400) column (40% ethyl acetate in petroleum ether) to give 4 as a light yellow fluffy solid (1.82 g, 58%). Melting range (MR): 51-65° C. $^1$H NMR (400 MHz, DMSO-d$_6$) δ(ppm): 8.07 (d, J=2.0 Hz, 1H), 7.80-7.77 (m, 1H), 7.34 (t, J=8.0 Hz, 1H), 7.26-6.92 (m, 7H), 6.83 (d, J=3.2 Hz, 1H), 6.35 (s, 1H), 5.25 (t, J=6.0 Hz, 1H), 4.45 (d, J=7.2 Hz, 1H), 3.40-3.32 (m, 4H), 2.38 (t, J=5.6 Hz, 2H), 2.25 (t, J=5.2 Hz, 2H), 1.87 (m, 1H), 1.16 (d, J=6.0 Hz, 1H), 1.05 (d, J=7.6 Hz, 1H). $^{13}$C NMR: (100 MHz, DMSO-d6): δ162.03, 157.55, 154.11, 145.64, 141.94, 139.57, 139.09, 138.65, 132.95, 129.43, 128.04, 125.84, 125.31, 124.66, 123.11, 120.95, 118.69, 111.17, 60.09, 44.92, 43.87, 35.59, 34.00, 28.88, 24.26 and 15.52. MS m/z (M+H) 456.3, HPLC purity: 98.99%, Chiral HPLC: 98.95%.

Example 30: Synthesis of 4-[3-(5-methoxymethyl-pyridin-2-yloxy)-benzylidene]-piperidine-1-carboxylic acid ((1R,2S)-2-phenyl-cyclopropyl)-amide

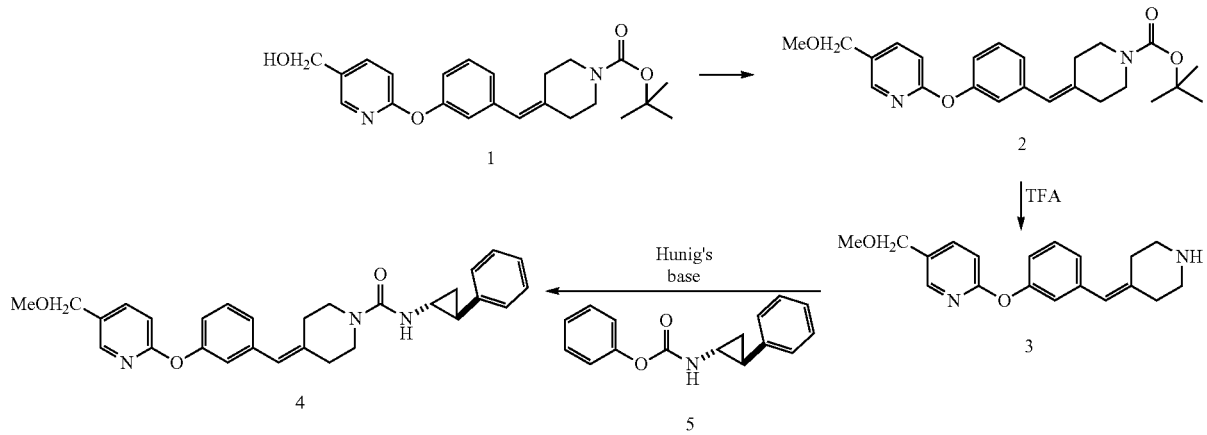

Step 1: To a solution of 1, product of step 1 of Example 29, (3.2 g, 8.0 mmol) in tetrahydrofuran (32 mL) was added 60% NaH (0.97 g, 0.024 mol) at ice temperature and the reaction mixture was stirred at room temperature over a period of 10 minutes. Methyl iodide (1.56 mL, 0.024 mol) was added to the reaction mass at the same ice temperature and continued the stirring for 12 h. Reaction was monitored by TLC. After complete consumption of starting material, reaction was quenched with saturated ammonium chloride solution (100 mL) and extracted with ethyl acetate (300 mL). Organic layer further washed with water, dried over anhydrous sodium sulphate, filtered and concentrated under reduced pressure. The crude product obtained was purified by silica-gel (230-400) column chromatography to obtain the product 2 as an off-white solid (2.6 g, 78%). $^1$H NMR (400 MHz, DMSO-d$_6$) δ(ppm): 8.08 (d, J=2.0 Hz, 1H), 7.80-7.78 (m, 1H), 7.35 (t, J=8.0 Hz, 1H), 7.06-6.93 (m, 4H), 6.35 (s, 1H), 4.37 (s, 2H), 3.40-3.32 (m, 4H), 3.26 (s, 3H), 2.38 (t, J=5.6 Hz, 2H), 2.25 (t, J=5.6 Hz, 2H), 1.39 (s, 9H). MS m/z (M+H): 411.3

Step 2: To a solution of 2 (2.6 g, 6.3 mmol) in dichloromethane (26.0 mL) was added trifluoroacetic acid (10.4 mL) at ice temperature and the reaction mixture was stirred at room temperature over a period of 2 h. Reaction was monitored by TLC. After complete consumption of starting material, volatiles were removed under reduced pressure to obtain product as brow red oil. The crude product obtained was washed with ether (3×50 mL) to yield 3 as a pale yellow thick liquid (2.9 g crude). $^1$H NMR (400 MHz, DMSO-d$_6$) δ(ppm): 8.69 (bs, 2H), 8.09-8.08 (m, 1H), 7.81-7.78 (m, 1H), 7.38 (t, J=7.6 Hz, 1H), 7.08-6.97 (m, 4H), 6.45 (s, 1H), 4.37 (s, 2H), 3.27 (s, 3H), 3.15-3.09 (m, 4H), 2.60 (t, J=5.6 Hz, 2H), 2.45 (t, J=5.6 Hz, 2H). MS m/z (M+H): 311.3

Step 3: To a solution of 3 (2.9 g, 6.8 mmol) in dimethyl sulfoxide (30 mL, 10V) was added diisopropyl ethyl amine (3.5 mL, 0.0205 mol) and the carbamate product 5 of Step 4, Example 16 (1.7 g, 6.8 mmol) at 25° C. The reaction mixture was allowed to stir at 60° C. over a period of 6 h. Reaction was monitored by TLC. The resulting reaction mixture was diluted with ethyl acetate (300 mL), washed with water (3×100 mL) and dried over sodium sulphate. The crude product obtained upon evaporation of the volatiles were purified through silica gel (230-400) column (30% ethyl acetate in n-hexane) to give product 4 as a light yellow gummy solid (2.6 g, 86%). $^1$H NMR (400 MHz, DMSO-d$_6$) δ(ppm): 8.08 (d, J=2.0 Hz, 1H), 7.81-7.78 (m, 1H), 7.33 (t, J=7.6 Hz, 1H), 7.25-7.21 (m, 2H), 7.09-6.93 (m, 7H), 6.83 (d, J=3.2 Hz, 1H), 6.34 (s, 1H), 4.37 (s, 2H), 3.38-3.28 (m, 4H), 3.27 (s, 3H), 2.71-2.69 (m, 1H), 2.36 (t, J=5.6 Hz, 2H), 2.25 (t, J=5.6 Hz, 2H), 1.85 (m, 1H), 1.13 (d, J=4.8 Hz, 1H), 1.04 (d, J=7.6 Hz, 1H). $^{13}$C NMR: (100 MHz, DMSO-d6): δ162.60, 157.57, 153.87, 146.76, 142.00, 140.15, 139.65, 138.71, 129.52, 128.87, 128.10, 125.86, 125.35, 124.90, 123.12, 121.21, 118.96, 111.26, 70.58, 57.49, 44.94, 43.90, 35.63, 34.08, 28.92, 24.31 and 15.57. MS m/z (M+H): 470.3, HPLC Purity: 99.57%, Chiral HPLC: 99.60%.

Example 31—Soluble Epoxide Hydrolase (sEH) Inhibition Assay

The sEH enzyme inhibition assay was performed using a commercially available kit from Cayman Chemical Company of Ann Arbor, Michigan (Cayman Cat. No. 10011671). The assay uses 3-phenyl-cyano(6-methoxy-2-naphthalenyl)-methyl ester-2-oxiraneacetic acid as the substrate for sEH. Hydrolysis of the substrate yields a highly fluorescent product that can be monitored at excitation and emission wavelengths of 330 and 465 nm, respectively. The assay mixture consists of 185-190 μL assay buffer, 5 μL of sEH enzyme in a 96 well plate. Compounds at different concentrations (in 5 μL DMSO) or DMSO (vehicle) alone were added and the reaction was initiated by the addition of 5 μl of substrate. The plate was incubated for 15 min at 25° C. Data analysis was performed and the percentage inhibition determined.

Compounds that inhibit soluble epoxide hydrolase at concentration ($IC_{50}$) of less than 10 μM are considered active. Inhibitory activity of compounds of Formula I is given in Table 1, see FIG. 1.

The efficacy of compounds of general Formula I in neuropathic and inflammatory pain can be evaluated using animal models known in literature (*Pain*, 43, 1990, 205-218; Pain, 153, 2012, 2380-2392).

Example 32—the Model (Partial Sciatic Nerve Ligation) Described Below can be Used to Evaluate Potential of Compounds of Formula 1 to Treat Neuropathic Pain Rats were anesthetized with Ketamine hydrochloride inj (Aneket® obtained from Neon Laboratories Ltd. of Mumbai, India.) 100 mg/kg, i.p. and Xylazine hydrochloride inj. (Xylazine obtained from Indian Immunologicals Ltd. of Hyderabad, India) 10 mg/kg, i.p. mixed in a 10:1 ratio. The right sciatic nerve was exposed in the proximal thigh region. The dorsum of the nerve was carefully freed from surrounding connective tissues at a site near the trochanter just distal to the point at which the posterior biceps semitendinosus (PBST) nerve branches off the common sciatic nerve. The nerve was fixed in its place by pinching the epineurium on its dorsal aspect, taking care not to press the nerve against the underlying structures. A 5-0 mersilk (obtainable from the Johnson & Johnson Company, Ethicon) was inserted into the nerve with a ⅜ curved, reverse-cutting mini-needle, and ligated tightly so that the dorsal one-third to one-half of the nerve thickness was trapped in the ligature. The muscle was closed with 3-0 vicryl absorbable suture and also skin with skin staples. Sulfanilamide (Negasunt® from Bayer) dusting powder was applied on the muscle after suturing. Sham controls were performed for each surgery by exposing the nerve without ligation and the wound was closed as above mentioned method. After completion of surgery, animals were housed individually in a cage under warm conditions till they recover from anesthesia. On day 6, paw withdrawal latencies were measured and randomized. Following body weight measurement and a minimum of 15 min acclimatization to procedure room, the animals were administered, in a staggered manner, test items (Compound C or Compound D of Formula I at 25 mg/kg/day, oral; reference item gabapentin (30 mg/kg/day, ip) or vehicles as per the study plan. The volume of the dose administered was based on the body weight of the animals.

The paw withdrawal latency (PWL) of both hind paws of all rats were measured by using Hargreaves Plantar test apparatus (obtained from Ugo Basile of Comerio, Italy), once pre- and twice post-dosing (on day 6 and day 12, each at 1 h and 3 h post treatment). The means of 2 close observations out of total 3/paw, at respective time point and based on the acceptance criteria (>−25 DS %), were considered for analysis. Two successive readings for the same paw, a gap of ~5 min, were maintained in between. Percentage difference score (% DS) in PWL between operated and non-operated paw, at the respective time point, was the measure of hyperalgesia.

% DS=100×(PWL for operated paw−PWL for non-operated paw)/PWL for non-operated paw The compounds that show significant percentage difference score over vehicle treated group are considered active. FIG. 2 shows the anti-hyperalgesic efficacy of Compound C and Compound D of Formula I in the neuropathic pain model.

Example 33—The Model (Streptozotocin-Induced Diabetic Neuropathy) Described Below can be Used to Evaluate Potential of Compounds of Formula 1 to Treat Peripheral Diabetic Neuropathy The study was carried following the published protocol and all treatments/measurements were done in a blinded fashion (*Current Protocols in Pharmacology* 2015, 70.1, 5-47; *Molecular Pain* 2014, 10, 1744-8069). A single dose of streptozotocin (55 mg/kg, iv) was used for induction of type-I diabetes in rats. Animals became significantly diabetic (glucose levels up to 600 mg/dl) by day-4 and remained diabetic until the end of the study. Paw withdrawal threshold (PWT) was measured on the day prior to streptozotocin-injection using manual von Frey filaments (basal values) and the animals were stratified based on their PWT values. For acute study, on day-10, animals were given vehicle, pregabalin (30 mg/kg) or Compound A of Formula I, The PWT was assessed at 1, 2, 4 and 6 h post dosing and compared to sham and diabetic control (pathological control) animals. For chronic study compound A (3 mg/kg/day) and vehicle or pregabalin dosing was continued for 5 additional days and PWT assessed on day-15 at 1, 2, 4 and 6 h after last dosing and compared to sham and diabetic control groups. Two way ANOVA statistical analysis for blood glucose and PWT, and one way ANOVA for AUC (0-6) followed by "Dunnett's Multiple Comparison Test" at 95% confidence (alpha 0.05) interval compared to diabetic control group were performed.

Figure 3:
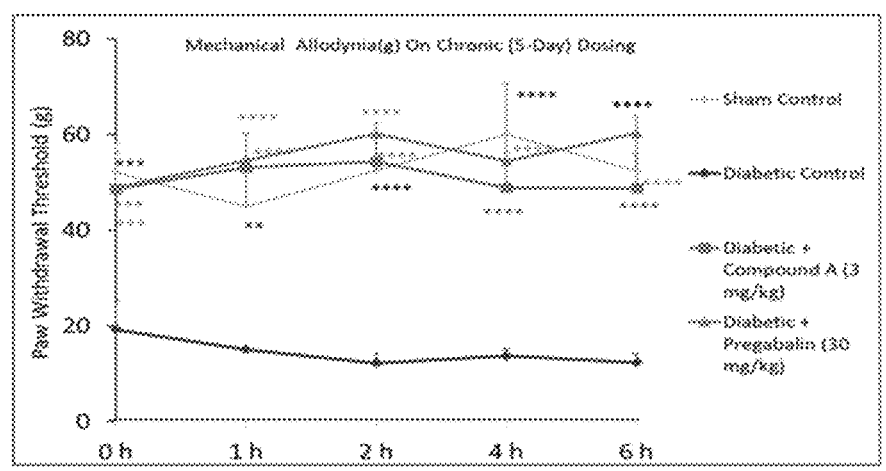
FIG. 3 shows efficacy of Compound A of Formula I in a diabetic peripheral neuropathy model.

FIG. 3 shows efficacy (pain modulation) of Compound A as compared to diabetic and sham control animals in stretptozotocin-induced diabetic peripheral neuropathy model.

Example 34—the Model (MPTP Induced Parkinsonism in Zebrafish) Described Below can be Used to Evaluate Potential of Compounds of Formula 1 to Treat Parkinson's Disease The methodology described by Bretaud et al (Neurotoxicol Teratol. 2004 November-December; 26(6), 857-64) was used to study parkinsonism in zebrafish. For MPTP (1-methyl-4-phenyl-1,2,3,6-tetrahydropyridine) induced Parkinsonism, adult zebrafish were injected with 3 μl of 60 μg/g of MPTP as intramuscular injection along the lateral muscles.

Compound B of Formula I or L-DOPA were dosed orally by mixing with the fish feed pellets. Fishes were conditioned to consume three pellets a day. To prepare feed containing 1 ng of Compound B of Formula I, stock of 1 ng/μl Compound B was diluted to 10 μl in Ringer's solution and distributed to 3 fish feed pellets ('3.3 μl per pellet). Prior to adding Compound B, fish feed pellets were dried at 37° C. for 1 hour to remove moisture. Post addition of Compound B solution and absorption by the pellet, pellets were stored at 4° C. To prepare fish feed pellets containing L-DOPA 4 μl of 1 ng/μl of L-DOPA stock solution was distributed across 3 fish feed pellets '1.3 μl/pellet. Fish were fed, three pellets a day. Concentration of compounds dosed was controlled by number of pellets and the quantity of compound per pellet. Feed pellets without drug but with vehicle were used as placebo or control.

Locomotor Activity: The observation tank was divided into four zones by drawing three vertical lines at equal distances, at a length of 6.25 cm per zone. The number of lines that adult zebrafish crossed over a period of 5 minutes was counted. Fishes were allowed to acclimatize in measurement tanks for a period of 30 minutes before readings were taken. Measurements were separated by a period of 4 hours before compound dosing or MPTP challenge.

Brain Pathology: Fish were anesthetized with 15° C. water and sacrificed by a cut between the brain and the spinal cord. Brain was dissected and portions of mid brain were removed with a pin and knife. The brain tissue was smeared on a glass slide and stained with Haematoxylin & Eosin respectively for 2 minutes each followed by water washes. Slides were viewed at 45× magnification using Labomed LX 400 microscope. The number of degenerated neurons were counted for three fields per smear. Degenerate neurons were characterized by loss of cell structure, either swollen or constricted cells, irregular shaped cell membrane, stain relatively lighter with high rate of cell lysis during smear preparation as per established protocols (Proc Natl Acad Sci USA. 2016 Apr. 12; 113 (15): E2189-98; J Cytol. 2010 July; 27(3): 81-85; J Cytol. 2011 October-December; 28(4): 147-158)

Statistical analysis: Statistical comparisons were made using GraphPad. Student's t-test with a 95% confidence interval was performed using a two-way ANOVA at an alpha=0.05 (95% confidence interval) and Tukey's multiple comparison post-testing was used to compare the means of each column. Significance is denoted with asterisks: ns not significant, *P<0.05, P<0.01, *P<0.001, ****P<0.0001.

Figure 4:
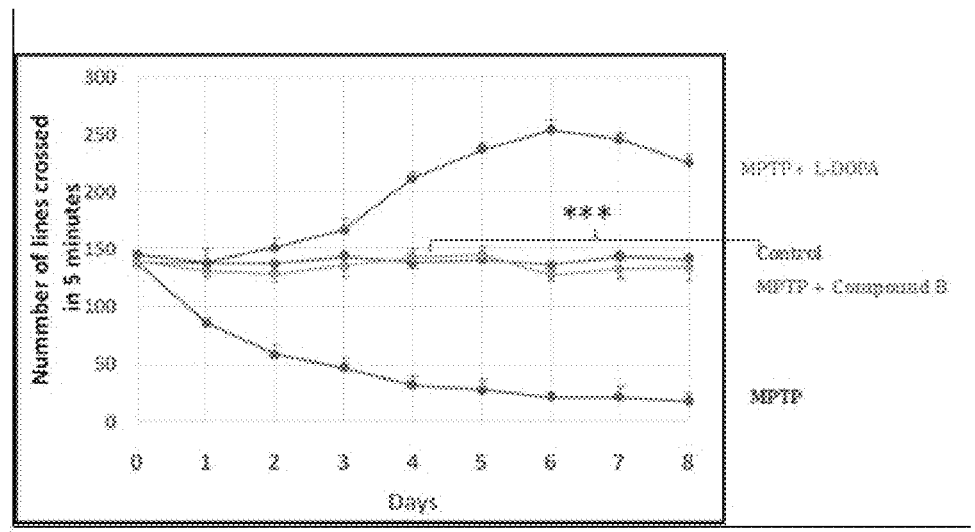
FIG. 4 shows efficacy (improvement in locomotor activity) of Compound B of Formula I in a Parkinson's disease model.

FIG. 4 shows that treatment with Compound B completely alleviated MPTP-induced changes in locomotor activity. However, continued treatment with L-DOPA (beyond day 3) resulted in heightened movement behavior which may reflect L-DOPA-induced dyskinesia as also observed in humans.

Figure 5:
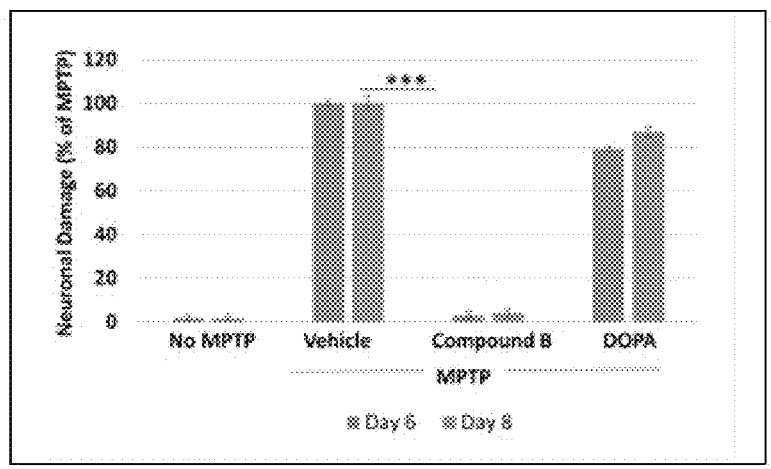
FIG. 5 shows neuroprotection of Compound B of Formula I in a Parkinson's disease model.

FIG. 5 revealed significant increase in neurodegenerative cells in MPTP treated group (Days 6 and 8 treatment) with abnormal cellular structure, disorganized cellular arrangement, easily collapsible cells under smear and lightly stained cells. In L-DOPA treated groups, brain pathology showed a field similar to MPTP treated group, i.e. neurodegeneration with altered cellular structure indicating L-DOPA did not have significant effect on reducing MPTP induced toxicity on neuronal cells. On the other hand, brain smear of Compound B treated group predominantly showed strong staining characteristics with intact cellular structure indicative of normal cells. Overall, neurodegenerative cell number was significantly decreased (>80%) in Compound B treated group compared to MPTP treated group. L-DOPA treated group had a non-significant decrease in neurodegenerative cell number on day 8 compared to MPTP group.

Example 35—The Model (MPTP Induced Parkinsonism in Mouse) Described Below can be Used to Evaluate Potential of Compounds of Formula 1 to Treat Parkinson's Disease.

Parkinson's Disease was Induced in all the Animals by Subcutaneous Injection of MPTP (20 mg/kg) for a Period 5 Days. Control Group Received No MPTP Compound B of Formula I was administered orally once daily at 15 (or 30 mg/kg) dose, 30 minutes prior to each MPTP injection, for five consecutive days. After 5-day treatment mice were subjected to behavioral (beam walk) test Beam walk test—Mice were trained before MPTP injection, to pass through a narrow beam of 100 cm length to reach an enclosed escape platform in a bright light (20 lux), which created an aversive stimulus. This boosts the mice to pass through the beam to the dark enclosed goal box. Individual mice were subjected to the test, 48 h after first MPTP injection. Time taken to cross the beam to reach enclosed escape platform, and number of foot slips were recorded. The latency to reach the platform was used as a measure of motor function and coordination, while the number of foot slip errors was used to assess balance.

Figure 6:
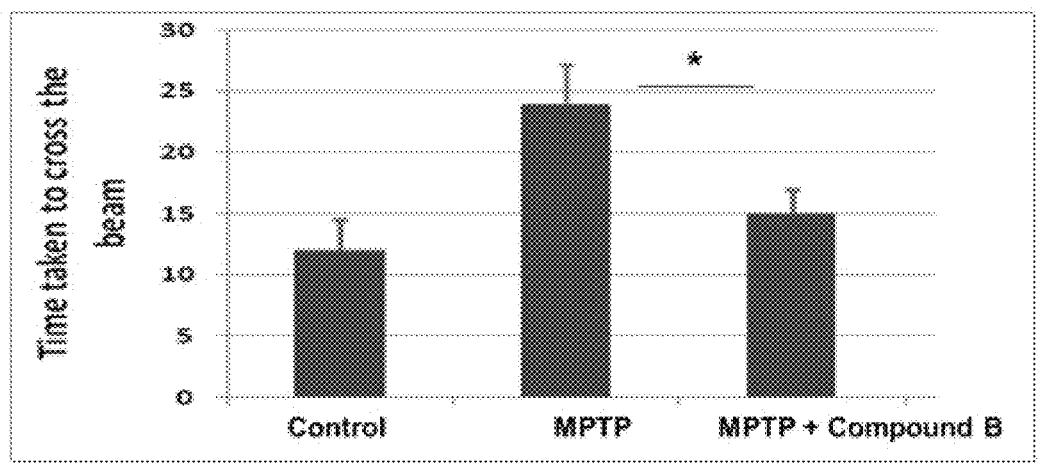
FIG. 6 shows efficacy (improvement in locomotor activity) of Compound B of Formula I in a rodent model of Parkinson's disease.

FIG. 6 shows treatment with Compound B of Formula I significantly reduced the time taken to cross the beam compared to the MPTP group animals.

Various modifications and variations of the described methods, pharmaceutical compositions, and kits of the disclosure will be apparent to those skilled in the art without departing from the scope and spirit of the disclosure. Although the disclosure has been described in connection with specific embodiments, it will be understood that it is capable of further modifications and that the disclosure as claimed should not be unduly limited to such specific embodiments. Indeed, various modifications of the described modes for carrying out the disclosure that are obvious to those skilled in the art are intended to be within the scope of the disclosure. This application is intended to cover any variations, uses, or adaptations of the disclosure following, in general, the principles of the disclosure and including such departures from the present disclosure come within known customary practice within the art to which the disclosure pertains and may be applied to the essential features herein before set forth.

What is claimed is:
1. A composition comprising at least one compound of Formula III:

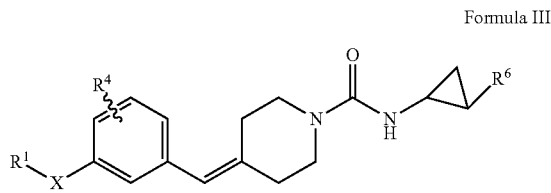

Formula III its stereoisomers or pharmaceutically acceptable salts thereof;
wherein
$R^1$ is selected from a group consisting of alkyl, hydrogen, haloalkyl, cycloalkyl, heterocycloalkyl, aryl, or heteroaryl and wherein when $R^1$ is aryl, heteroaryl or heterocycloalkyl, $R^1$ is unsubstituted or substituted with alkyl, hydroxy, halogen, haloalkyl, hydroxyalkyl, alkoxyalkyl, alkoxy, amine, $SO_2R^5$, $SO_2NHR^2$, or $COR^3$;
$R^2$ is selected from a group consisting of hydrogen, alkyl, haloalkyl, or cycloalkyl;
$R^3$ is selected from a group consisting of alkyl, cycloalkyl, hydroxy, amine, alkylamine or alkoxy;
$R^4$ is selected from a group consisting of hydrogen, alkyl, halogen, haloalkyl, hydroxy, amine, alkoxy, $SO_2R^5$, $SO_2NHR^2$, or $COR^3$;

R[5] is selected from a group consisting of alkyl, haloalkyl, cycloalkyl, aryl or amine;

R[6] is selected from a group consisting of alkyl, cycloalkyl, aryl or heteroaryl; and X is selected from O, (CH₂)p, NH and p is from 0-2.

2. A composition comprising at least one compound of Formula IV

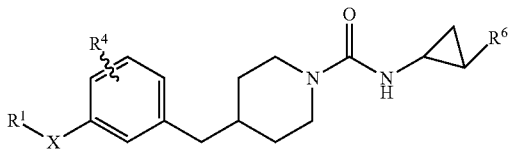

Formula IV its stereoisomers or pharmaceutically acceptable salts thereof;

wherein

R[1] is selected from a group consisting of alkyl, hydrogen, haloalkyl, cycloalkyl, heterocycloalkyl, aryl, or heteroaryl and wherein when R[1] is aryl, heteroaryl or heterocycloalkyl, R[1] is unsubstituted or substituted with alkyl, hydroxy, halogen, haloalkyl, hydroxyalkyl, alkoxyalkyl, alkoxy, amine, SO₂R[5], SO₂NHR[2], or COR[3];

R[2] is selected from a group consisting of hydrogen, alkyl, haloalkyl, or cycloalkyl;

R[3] is selected from a group consisting of alkyl, cycloalkyl, hydroxy, amine, alkylamine or alkoxy;

R[4] is selected from a group consisting of hydrogen, alkyl, halogen, haloalkyl, hydroxy, amine, alkoxy, SO₂R[5], or COR[3];

R[5] is selected from a group consisting of alkyl, haloalkyl, cycloalkyl, aryl or amine;

R[6] is selected from a group consisting of alkyl, cycloalkyl, aryl or heteroaryl, aryl or heteroaryl may optionally be substituted one or more times with groups or substituents consisting of alkyl, hydroxy, halogen, or haloalkyl; and X is selected from O, (CH₂)p, NH; wherein p is selected from 0-2, however when p=0, R[1] is not aryl.

3. A composition comprising one or more of the following compounds, its stereoisomers or pharmaceutically acceptable salts thereof;

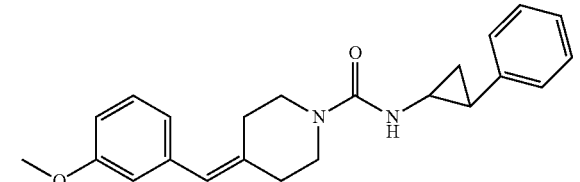

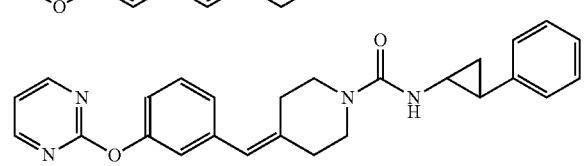

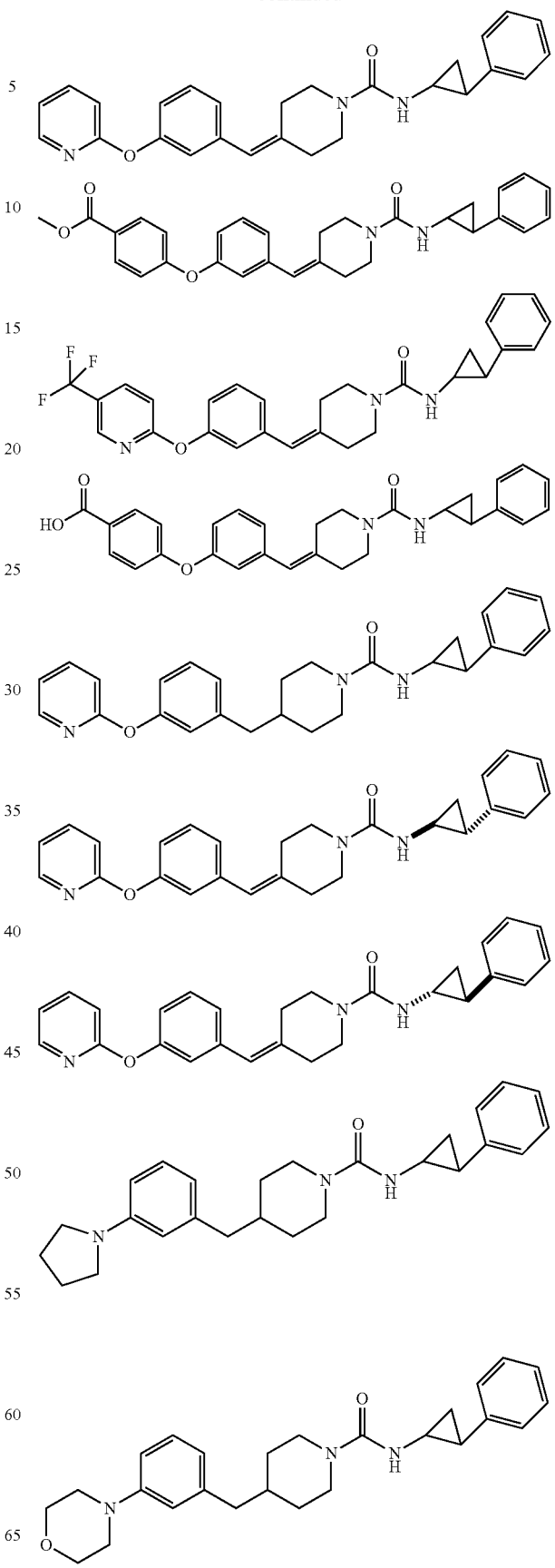

125
-continued
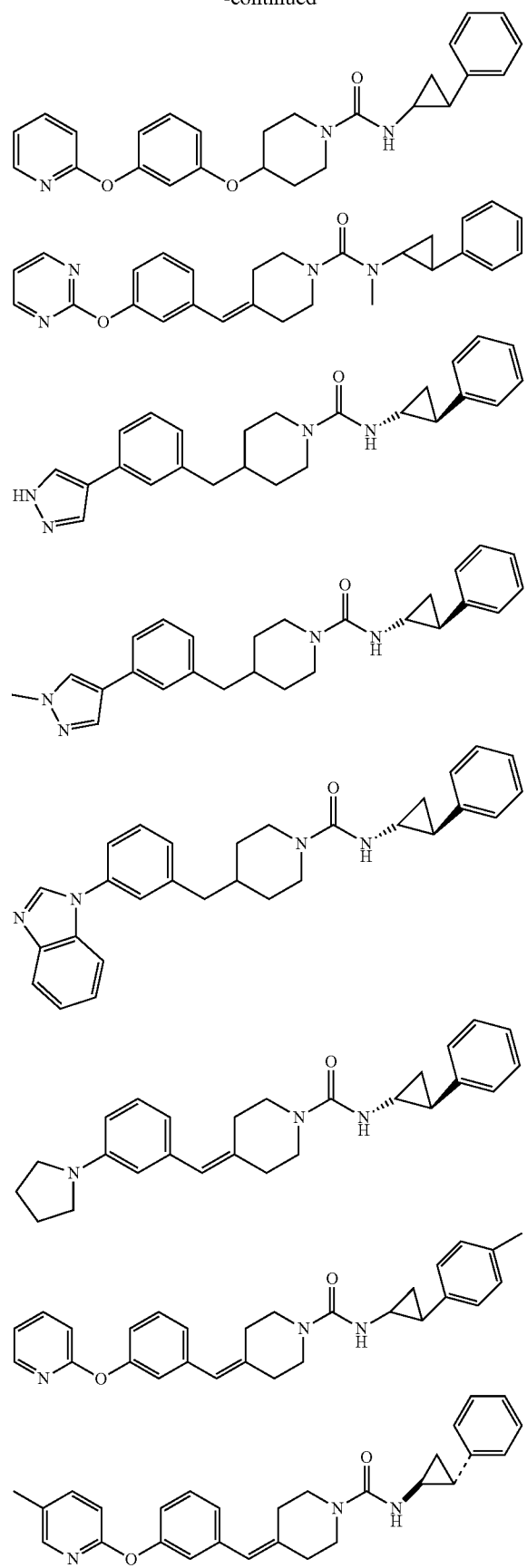
126
-continued
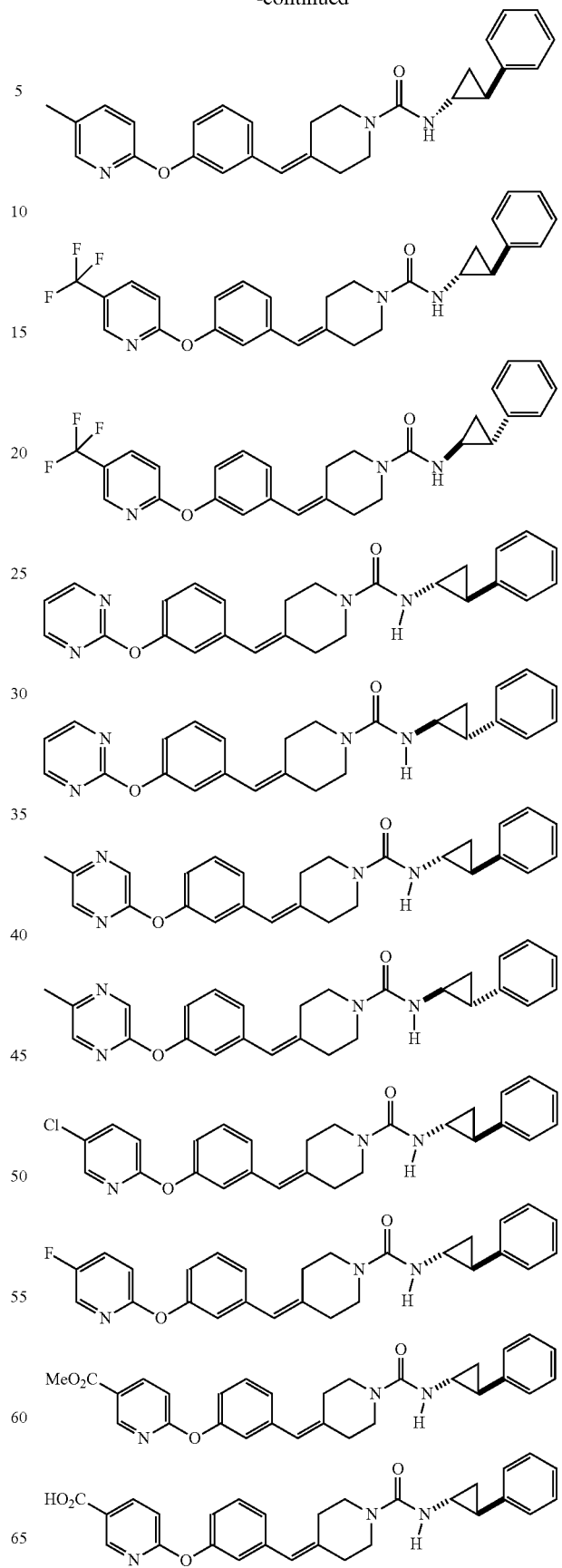

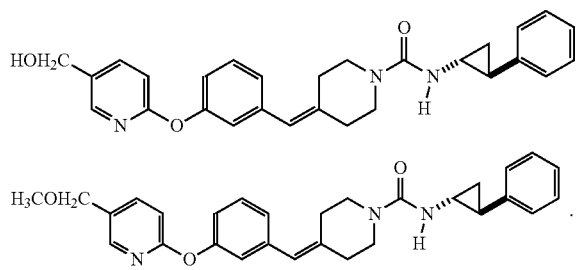

4. A pharmaceutical composition comprising a pharmaceutically acceptable carrier and at least one compound of claim 1.

5. A pharmaceutical composition comprising a pharmaceutically acceptable carrier and at least one compound of claim 2.

6. A pharmaceutical composition comprising a pharmaceutically acceptable carrier and at least one compound of claim 3.

7. A method for treatment of pain, neurodegenerative disease, or inflammatory disease in a subject, the method comprising administering to the subject a therapeutically effective amount of at least one compound of Formula III

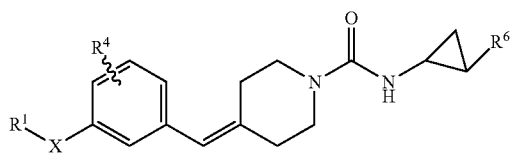

Formula III its stereoisomers or pharmaceutically acceptable salts thereof wherein $R^1$ is selected from a group consisting of alkyl, hydrogen, haloalkyl, cycloalkyl, heterocycloalkyl, aryl, or heteroaryl and wherein when $R^1$ is aryl, heteroaryl or heterocycloalkyl, $R^1$ is unsubstituted or substituted with alkyl, hydroxy, halogen, haloalkyl, hydroxyalkyl, alkoxyalkyl, alkoxy, amine, $SO_2R^5$, $SO_2NHR^2$, or $COR^3$;

$R^2$ is selected from a group consisting of hydrogen, alkyl, haloalkyl, or cycloalkyl;

$R^3$ is selected from a group consisting of alkyl, cycloalkyl, hydroxy, amine, alkylamine or alkoxy;

$R^4$ is selected from a group consisting of hydrogen, alkyl, halogen, haloalkyl, hydroxy, amine, alkoxy, $SO_2R^5$, $SO_2NHR^2$, or $COR^3$;

$R^5$ is selected from a group consisting of alkyl, haloalkyl, cycloalkyl, aryl or amine;

$R^6$ is selected from a group consisting of alkyl, cycloalkyl, aryl or heteroaryl; and X is selected from O, $(CH_2)p$, NH and p is from 0-2.

8. A method for treatment of pain, neurodegenerative disease, or inflammatory disease in a subject, the method comprising administering to the subject a therapeutically effective amount of at least one compound of Formula IV

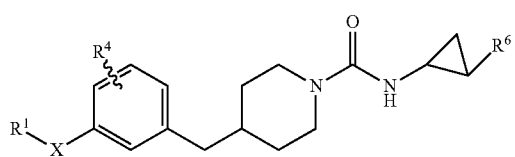

Formula IV its stereoisomers or pharmaceutically acceptable salts thereof, wherein $R^1$ is selected from a group consisting of alkyl, hydrogen, haloalkyl, cycloalkyl, heterocycloalkyl, aryl, or heteroaryl and wherein when $R^1$ is aryl, heteroaryl or heterocycloalkyl, $R^1$ is unsubstituted or substituted with alkyl, hydroxy, halogen, haloalkyl, hydroxyalkyl, alkoxyalkyl, alkoxy, amine, $SO_2R^5$, $SO_2NHR^2$, or $COR^3$;

$R^2$ is selected from a group consisting of hydrogen, alkyl, haloalkyl, or cycloalkyl;

$R^3$ is selected from a group consisting of alkyl, cycloalkyl, hydroxy, amine, alkylamine or alkoxy;

$R^4$ is selected from a group consisting of hydrogen, alkyl, halogen, haloalkyl, hydroxy, amine, alkoxy, $SO_2R^5$, or $COR^3$;

$R^5$ is selected from a group consisting of alkyl, haloalkyl, cycloalkyl, aryl or amine;

$R^6$ is selected from a group consisting of alkyl, cycloalkyl, aryl or heteroaryl, aryl or heteroaryl may optionally be substituted one or more times with groups or substituents consisting of alkyl, hydroxy, halogen, or haloalkyl; and X is selected from O, $(CH_2)p$, NH; wherein p is selected from 0-2, however when p=0, $R^1$ is not aryl.

9. A method for treatment of pain, neurodegenerative disease, or inflammatory disease in a subject, the method comprising administering to the subject a therapeutically effective amount of at least one compound selected from:

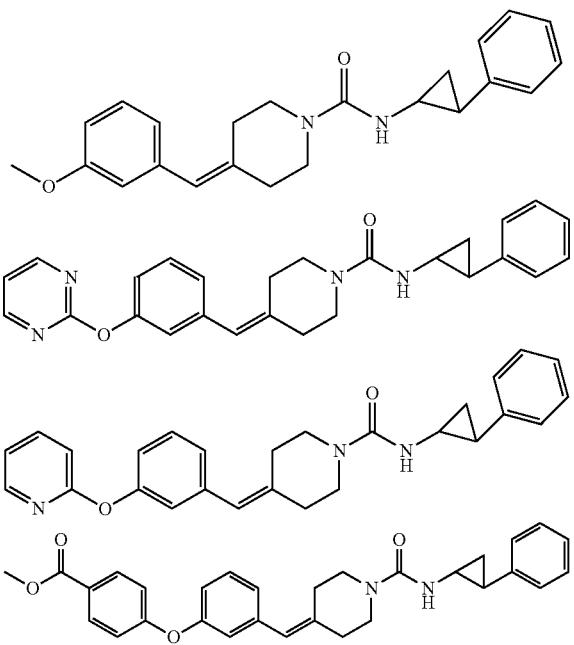

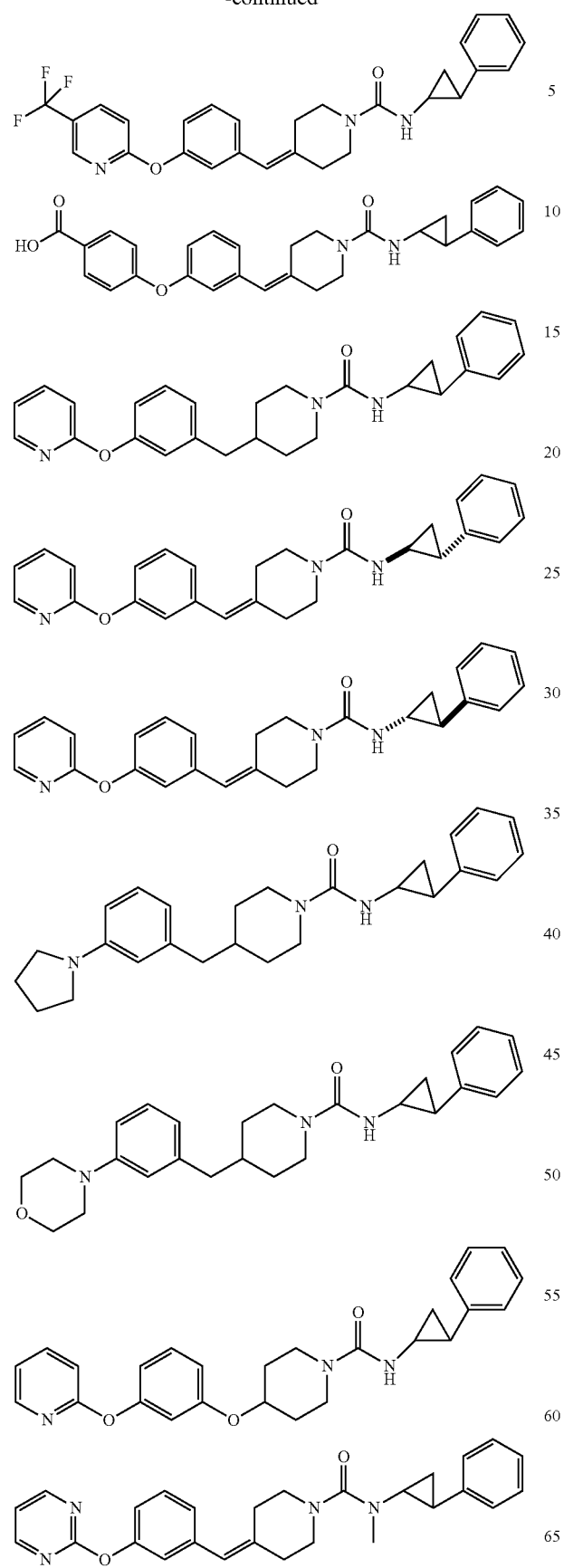
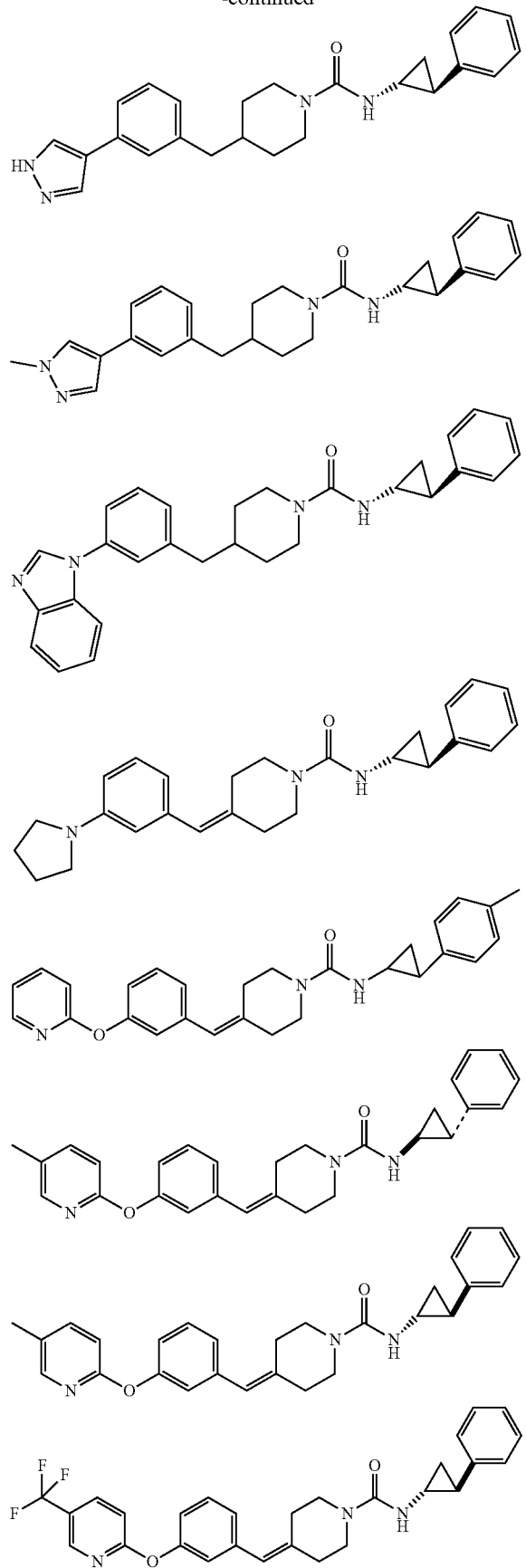

-continued

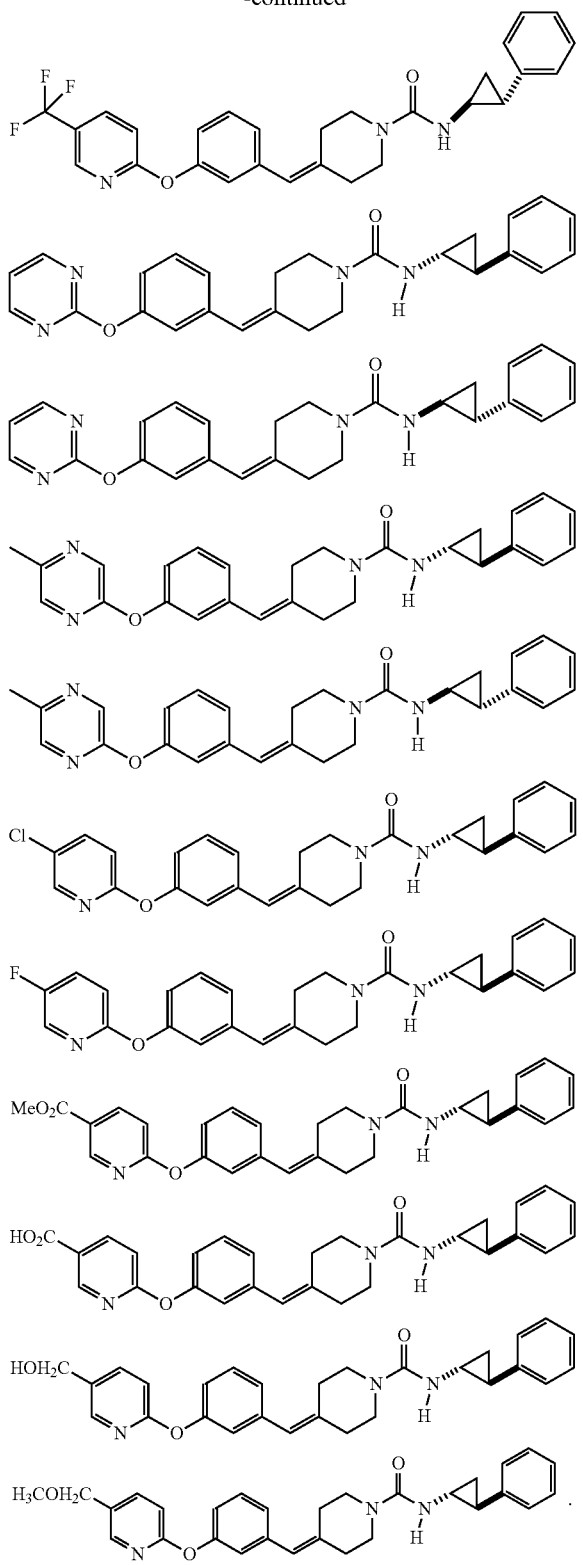

10. A method for treatment of neuropathic or inflammatory pain in a subject, the method comprising administering to the subject a therapeutically effective amount of the composition of claim 1.

11. A method for the treatment of neuropathic or inflammatory pain in a subject, the method comprising administering to the subject a therapeutically effective amount of the composition of claim 2.

12. A method for the treatment of neuropathic or inflammatory pain in a subject, the method comprising administering to the subject a therapeutically effective amount of the composition of claim 3.

13. A method for treatment of Parkinson's disease in a subject, the method comprising administering to the subject a therapeutically effective amount of the composition of claim 1.

14. A method for treatment of Parkinson's disease in a subject, the method comprising administering to the subject a therapeutically effective amount of the composition of claim 2.

15. A method for treatment of Parkinson's disease in a subject, the method comprising administering to the subject a therapeutically effective amount of the composition of claim 3.

16. A method for treatment of diabetic peripheral neuropathy in a subject, the method comprising administering to the subject a therapeutically effective amount of the composition of claim 1.

17. A method for treatment of diabetic peripheral neuropathy in a subject, the method comprising administering to the subject a therapeutically effective amount of the composition of claim 2.

18. A method for treatment of diabetic peripheral neuropathy in a subject, the method comprising administering to the subject a therapeutically effective amount of the composition of claim 3.

19. A method of claim 10, wherein the neuropathic pain is peripheral neuropathic pain.

20. A method of claim 11, wherein the neuropathic pain is peripheral neuropathic pain.

21. A method of claim 12, wherein the neuropathic pain is peripheral neuropathic pain.

22. A method of claim 10, wherein the neuropathic pain is selected from a group consisting of post-herpetic neuralgia, trigeminal neuralgia, focal peripheral nerve injury, anesthesia dolorosa central pain, spinal cord injury, multiple sclerosis, peripheral neuropathy, HIV, or chemotherapy-induced pain.

23. A method of claim 11, wherein the neuropathic pain is selected from a group consisting of post-herpetic neuralgia, trigeminal neuralgia, focal peripheral nerve injury, anesthesia dolorosa central pain, spinal cord injury, multiple sclerosis, peripheral neuropathy, HIV, or chemotherapy-induced pain.

24. A method of claim 12, wherein the neuropathic pain is selected from a group consisting of post-herpetic neuralgia, trigeminal neuralgia, focal peripheral nerve injury, anesthesia dolorosa central pain, spinal cord injury, multiple sclerosis, peripheral neuropathy, HIV, or chemotherapy-induced pain.

* * * * *